(12) United States Patent
Paul et al.

(10) Patent No.: US 6,855,528 B2
(45) Date of Patent: Feb. 15, 2005

(54) METHODS FOR IDENTIFYING INDUCERS AND INHIBITORS OF PROTEOLYTIC ANTIBODIES, COMPOSITIONS AND THEIR USES

(75) Inventors: Sudhir Paul, Houston, TX (US); Gennady Gololobov, Houston, TX (US); Larry J. Smith, 7824 Jackson St., Omaha, NE (US) 68114

(73) Assignees: Larry J. Smith, Omaha, NE (US); University of Nebraska Board of Regents, Lincoln, NE (US)

( * ) Notice: Subject to any disclaimer, the term of this patent is extended or adjusted under 35 U.S.C. 154(b) by 100 days.

(21) Appl. No.: 09/862,849

(22) Filed: May 22, 2001

(65) Prior Publication Data

US 2002/0013274 A1 Jan. 31, 2002

Related U.S. Application Data

(62) Division of application No. 09/046,373, filed on Mar. 23, 1998, now Pat. No. 6,235,714.

(51) Int. Cl.[7] ........................ C12N 9/00; A61K 38/04; A61K 38/43
(52) U.S. Cl. .................. 435/188.5; 424/94.1; 514/13
(58) Field of Search .................. 435/188.5; 424/94.1; 514/13

(56) References Cited

U.S. PATENT DOCUMENTS 5,948,658 A * 9/1999 Landry .................... 435/188.5

OTHER PUBLICATIONS

Lerner, R.A., et al. (1991) Science 252, 659–667.*
Blackburn, G.M., et al. (196) Pure & Appl. Chem. 68(11), 2009–2016.*
Paul, S., et al. (2003) J. Biol. Chem. 278(22), 20429–20435.*
Paul, S., D.J. Volle, C.M. Beach, D.R. Johnson, M.J. Powell, and R.J. Massey. Catalytic Hydrolysis of Vasoactive Intestinal Peptide by Human Autoantibody. *Science*. 1989. 244:1158–1162.
Paul, S., S. Mei, B. Mody, S.H. Eklund, C.M. Beach, R.J. Massey, and F. Hamel. Cleavage of Vasoactive Intestinal Peptide at Multiple Sites by Autoantibodies. *The Journal of Biological Chemistry*. 1991. 266:16128–16134.
Li, L., S. Paul, S. Tyutyulkova, M.D. Kazatchkine, and S. Kaveri. Catalytic Activity of Anti–Thyroglobulin Antibodies. *The Journal of Immunology*. 1995. 3328–3332.
Shuster, A.M., G.V. Gololobov, O.A. Kvashuk, A.E. Bogomolova, I.V. Smirnov, and A.G. Gabibov. DNA Hydrolyzing Autoantibodies. *Science*. 1992. 256:665–667.

Tawfik, D.S., R. Chap, B.S. Green, M. Sela, and Z. Eshhar. Unexpectedly high occurrence of catalytic antibodies in MRL/lpr and SJL mice immunized with a transition–state analog: Is there a linkage to autoimmunity? *Immunology*. 1995. 92:2145–2149.
Davies, D.R. and S. Chacko. Antibody Structure. *Acc. Chem. Res.* 1993, 26:421–427.
Sun, M., Q.S. Gao, L. Li, and S. Paul. Proteolytic Activity of an Antibody Light Chain. *The Journal of Immunology*. 1994. 5121–5126.
Gao, Q.S., M. Sun, S. Tyutyulkova, D. Webster, A. Rees, A. Iramontano, R.J. Hassey, and S. Paul. Molecular Cloning of a Proteolytic Antibody Light Chain. *The Journal of Biological Chemistry*. 1994. 269:32389–32393.
Titmas, R.C., T.S. Angeles, R. Sugasawara, N. Aman, M.J. Darsley, G. Blackburn, and M.T. Martin. Aspects of Antibody–Catalyzed Primary Amide Hydrolysis. *Applied Biochemistry and Biotechnology*. 1994. 47:277–290.
Gao, Q.S., M. Sun, A.R. Rees, and S. Paul. Site–directed Mutagenesis of Proteolytic Antibody Light Chain. *J. Mol. Bio*. 1995. 253:658–664.
Lerner, R.A., S.J. Benkovic, and P.G. Schultz. At the Crossroads of Chemistry and Immunology: Catalytic Antibodies. *Science*. 1991. 252:659–667.
Tyutyulkova, S., Q.S. Gao, A. Thompson, S. Rennard, and S. Paul. Efficient vasoactive intestinal polypeptide hydrolyzing autoantibody light chains selected by phage display. *Biochimica et Biophysica Acta*. 1996. 217–223.
Sampson, N.S. and P.A. Bartlett. Peptide Phosphonylating Agents as Irreversible Inhibitors of Serine Proteases and Models of the Tetrahedral Intermediates. *Biochemistry*. 1991. 30:2255–2262.
Baylis, E.K., C.D. Campbell, and J.G. Dingwall. Aminoalkylphosphonous Acids. Isosteres of the Protein Amino Acids. *J. Chem. Soc Perkin Trans*. 1984. 2845–2853.
Clackson, T., H.R. Hoogenboom, A. D. Griffiths, and G. Winter. Making antibody fragments using phage display libraries. *Nature*, 1991. 532:624–628.
McCafferty, J., K. J. Fitzgerald, J. Earnshaw, D.J. Chiswell, J. Link, R. Smith, and J. Kenten. Selection and Rapid Purification of Murine Antibody Fragments That Bind a Transition–State Analog by Phage Display. *Applied Biochemistry and Biotechnology*. 1994. 47:157–173.

(List continued on next page.)

*Primary Examiner*—Charles L. Patterson, Jr.
(74) *Attorney, Agent, or Firm*—Dann, Dorfman, Herrell and Skillman

(57) ABSTRACT

Covalently reactive antigen analogs are disclosed herein. The antigens of the invention may be used to stimulate production of catalytic antibodies specific for predetermined antigens assocated with particular medical disorders. The antigen analogs may also be used to permanently inactivate endogenously produced catalytic antibodies produced in certain autoimmune diseases as well as in certain lymphoproliferative disorders.

4 Claims, 16 Drawing Sheets

OTHER PUBLICATIONS

Mei, S., B. Mody, S.H. Eklund, and S. Paul. Vasoactive Intestinal Peptide Hydrolysis by Antibody Light Chains. *The Journal of Biological Chemistry*. 1991. 266:15571–15574.

Bone, R., N.S. Sampson, P.A. Bartlett, and D.A. Agard. Crystal Structures of α–Lytic Protease Complexes with Irreversibly Bound Phosphonate Esters. *Biochemistry*. 1991. 30:2263–2272.

Lax, I., R. Fischer, C. Ng, J. Serge, A. Ullrich, D. Givol, and J. Schlessinger. Noncontiguous regions in the extracellular domain of EGF receptor define ligand–binding specificity. *Cell Regulation*. 1991. 2:337–345.

Moore, J. and A. Trkola. HIV Type 1 Coreceptors, Neutralization Serotypes, and Vaccine Development. *AIDS Research and Human Retroviruses*. 1997. 13:733–736.

Thali, M., C. Furman, D.D. Ho, J. Robinson, S. Tilley, A. Pinter, and J. Sodroski. Discontinuous, Conserver Neutralization Epitopes Overlapping the CD4–Binding Region of Human Immunodeficiency Virus Type 1 gp120 Envelope Glycoprotein. *Journal of Virology*. 1992. 66:5635–5641.

Pollard, S.R., W. Meier, P. Chow, J.J. Rosa, and D.C. Wiley. CD4–Binding regions of human immunodeficiency virus envelope glycoprotein gp120 defined by proteolytic digestion. *Proc. Natl. Acad. Sci.* 1991. 88:11320–11324.

Kalaga, R., L. Li, J.R. O'Dell, and P. Sudhir. Unexpected Presence of Polyreactive Catalytic Antibodies in IgG from Unimmunized Donors and Decreased Levels in Rheumatoid Arthritis. *The Journal of Immunology*. 1995. 2695–2702.

Tramontano, A., K.D. Janda, and R.A. Lerner. Chemical reactivity at an antibody binding site elicited by mechanistic design of a synthetic antigen. *Proc. Natl. Acad. Sci. USA*. 1986. 83:6736–6740.

Bermas, B.L., M. Petri, J.A. Berzofsky, A. Waisman, G.M. Shearer, and E. Mozes. Binding of Glycoprotein 120 and Peptides from the HIV–1 Envelope by Autoantibodies in Mice with Experimentally Induced Systemic Lupus Erythematosus and in Patients with the Disease. *AIDS Research and Human Retroviruses*. 1994. 10:1071–1077.

Sudhir, P., L. Li, R. Kalaga, P. Wilkins–Stevens, F.J. Stevens, and A. Solomon. Natural Catalytic Antibodies: Peptide–hydrolyzing Activities of Bence Jones Proteins and $V_L$ Fragment. *The Journal of Biological Chemistry*. 1995. 270:15257–15261.

Pollack, S.J., P. Hsuin, and P.G. Schultz. Stereospecific Hydrolysis of Alkyl Esters by Antibodies. *J. Am. Chem. Soc.* 1989. 111:5961–5962.

Ahlers, J.D., C.D. Pendleton, N. Dunlop, A. Minassian, P.L. Nara, and J.A. Berzofsky. Construction of an HIV–1 Peptide Vaccine Containing a Multideterminant Helper Peptide Linked to a V3 Loop Peptide 18 Inducing Strong Neutralizing Antibody Responses in Mice of Multiple MHC Haplotypes after Two Immunizations. *The Journal of Immunology*. 1993. 150:5627–5665.

* cited by examiner

| Target Antigen | Disease Indications |
|---|---|
| CD4 | Rheumatoid Arthritis, Asthma, Transplantation, Autoimmune Disease |
| HER2 | Carcinoma |
| EGFR | Carcinoma |
| Macrophage Inhibitory Factor | Inflammatory and Autoimmune Disease |
| CD80 (B7-1) | Inflammatory and Autoimmune Disease, Atherosclerosis |
| CD86 (B7-2) | Inflammatory and Autoimmune Disease, Atherosclerosis |
| CD28 | Inflammatory and Autoimmune Disease, Atherosclerosis |
| CD70 | Inflammatory and Autoimmune Disease, Atherosclerosis |
| CD11b/CD18 | Arthritis, Inflammatory and Autoimmune Disease |
| CD23 | Arthritis, Inflammatory and Autoimmune Disease |
| ICAM-1 | Inflammatory and Autoimmune Disease, Rheumatoid Arthritis, Inflammatory Bowel Disease, Organ Transplant Rejection, Psoriasis, Atherosclerosis |
| VLA-4 Intrgrin Receptor | Inflammatory and Autoimmune Disease |
| TNF-alpha | Rheumatoid Arthritis, Autoimmune Disease, Neurotropic Pain, Ischemia-reperfusion Injury, Septic Shock, SIRS, ARDS, Multiple Sclerosis, AIDS |
| Complement Component C5 | Autoimmune Disease, Immunosuppression |

FIG. 19A

| Target Antigen | Disease Indications |
|---|---|
| IL-1 beta Receptor | Rheumatoid Arthritis, Autoimmune Disease, Neurotropic Pain, Ischemia-reperfusion Injury, Septic Shock, SIRS, ARDS |
| IL-1 beta | Rheumatoid Arthritis, Autoimmune Disease, Neurotropic Pain, Ischemia-reperfusion Injury, Septic Shock, SIRS, ARDS |
| GPIIb/IIIa Receptor | Anti-thrombotic, Use in combination with Angioplasty, Percutaneous Coronary Intervention, Unstable Angina, Stroke |
| Clotting Factor VII | Anti-coagulant |
| Plasminogen Activator Inhibitor (PAI-1) | Thrombolytic |
| IL-4 | Asthma |
| IL-4 Receptor | Asthma |
| IL-5 | Allergy |
| IL-5 Receptor | Allergy |
| IgE | Allergic Asthma and Allergic Rhinitis |
| Eotaxin | Allergic Inflammatory Disease, Allergic Asthma |
| Eotaxin Receptor | Allergic Inflammatory Disease, Allergic Asthma |
| PDGF | Vascular Disease, Restinosis |
| PDGF beta Receptor | Vascular Disease, Restenosis |
| alpha.v.beta.3 Integrin | Inhibit Pathologic Bone Resorption |

FIG. 19B

METHODS FOR IDENTIFYING INDUCERS AND INHIBITORS OF PROTEOLYTIC ANTIBODIES, COMPOSITIONS AND THEIR USES

This application is a divisional application of U.S. patent application Ser. No. 09/046,373, filed Mar. 23, 1998, now U.S. Pat. No. 6,235,714.

FIELD OF THE INVENTION

This invention relates to the fields of immunology, molecular biology and medicine. More specifically, the invention provides novel methods and compositions for stimulating the production of novel catalytic antibodies and inhibitors thereof. The invention also provides methods for identifying and isolating naturally occurring catalytic antibodies expressed from germline genes. Finally, the invention provides methods for synthesizing covalently reactive antigenic analogs which stimulate the production of catalytic antibodies and/or irreversibly inhibit the activity thereof.

BACKGROUND OF THE INVENTION

Several publications are referenced in this application by numerals in brackets in order to more fully describe the state of the art to which this invention pertains. The disclosure of each of these publications is incorporated by reference herein.

The observation that vasoactive intestinal peptide (VIP) is cleaved by antibodies (Abs) from asthma patients provided early evidence that Abs may possess peptidase activity [1,2] This observation has been reproduced independently by Suzuki et al [3]. Autoantibody catalysis is not restricted to catalysis of VIP. Autoantibodies in Hashimoto's thyroiditis catalyze the cleavage of thyroglobulin [4]. Further evidence for autoantibody catalysis has been provided by reports of DNase activity in Abs from lupus patients [5,6] The bias towards catalytic Ab synthesis in autoimmune disease is supported by observations that mouse strains with a genetic predisposition to autoimmune disease produce esterase Abs at higher levels when compared to control mouse strains in response to immunization with a transition state analog [7].

Like noncatalytic Abs, peptidase Abs are capable of binding Ags with high specificity mediated by contacts at residues from the VL and VH domains. The purified H and L subunits are known to be independently capable of binding antigens (Ags), albeit with lower affinity than the parent Ab. X-ray crystallography of Ab-Ag complexes have shown that the VL and VH domains are both involved in binding the Ag [8]. The precise contribution of the two V domains varies in individual Ab-Ag complexes, but the VH domain may contribute at a somewhat greater level, because CDRH3 tends to be longer and more variable in sequence compared to CDRL3.

The initial complexation of a polypeptide Ag by a peptidase Ab is followed by cleavage of one or more peptide bonds. Just prior to cleavage, contacts with the catalytic residues of the antibody are established with the peptide bond in the transition state. The ability to hydrolyze peptide bonds appears to reside in the VL domain. This conclusion is based on the cleavage of VIP by polyclonal autoantibody L chains, monoclonal L chains isolated from multiple myeloma patients and their recombinant VL domains, and recombinant L chains raised by immunization with VIP. The H chains of polyclonal and monoclonal Abs to VIP are capable of VIP binding but are devoid of the catalytic activity [9]. The VH domain can nevertheless influence the peptidase activity by "remote control", because in binding to VIP remote from the cleavage site, it can influence the conformation of the binding site as shown by the peptidase activity of $F_v$ constructs composed of the catalytic anti-VIP VL domain linked to its VH domain. The anti-VIP VH domain exerted beneficial effects and an irrelevant VH domain exerted detrimental effects on the catalytic activity, as evaluated by the values of VIP binding affinity and catalytic efficiency. The proposed existence of distinct catalytic and antigen binding subsites in catalytic Abs is consistent with data that Abs generally contain large combining sites, capable of accommodating 15–22 amino acids of polypeptide substrates [8], and that substrate regions distant from the cleavage site are recognized by the Abs. Thus, the VH domain offers a means to control the specificity of the catalytic site.

Molecular modeling of the L chain suggested that its Asp1, Ser27a and His93 are appropriately positioned to serve as the catalytic triad [10]. The hydrolysis of VIP was reduced by >90% by substitution of Ala residues for Ser27a, His93 or Asp1 by site-directed mutagenesis [12]. The catalytic activity of the wild type protein was inhibited selectively by diisopropylfluorophosphate (DFP), a serine protease inhibitor, but the residual activity of the Ser27a mutant was refractory to DFP. The $K_m$ of the wild type L chain for VIP (130 nM) was unaffected by mutations at Ser27a, His93 and Asp1. In contrast, mutagenesis at residues forming the extended active site of the L chain (Ser26, H27d/Asp28) produced increases in the $K_m$ values (by 10-fold) and increases in turnover (by 10-fold). These results can be explained as arising from diminished ground state stabilization. The consequent decrease of $\Delta G^r$cat produces an increase in turnover. Thus, two types of residues participating in catalysis by the L chain have been identified. Ser27a and His93 are essential for catalysis but not for initial high affinity complexation with the ground state of VIP. Ser26 and His27d/Asp28 participate in VIP ground state binding and limit turnover indirectly. See FIG. 1.

The VIPase L chain displayed burst kinetics in the early phase of the reaction, suggesting the formation of a covalent acyl-L chain intermediate, as occurs during peptide bond cleavage by serine proteases. The fluorescence intensity was monitored as a function of time after mixing the L chain with the substrate Pro-Phe-Arg-MCA. There was an immediate increase in fluorescence, corresponding to formation of the covalent intermediate, followed by a slower increase, corresponding to establishment of the steady rate. The number of active sites was computed from the magnitude of the burst by comparison with the fluorescence yield of standard aminomethylcoumarin. The concentration of catalytic sites was estimated at 114 nM, representing about 90% of the L chain concentration estimated by the Bradford method (125 nM).

The catalytic residues (Ser27a, His93, Asp1) in the anti-VIP VL domain are also present in its germline VL domain counterpart (GenBank accession number of the germline VL gene, Z72384). The anti-VIP VL domain contains 4 amino acid replacements compared to its germline sequence. These are His27d:Asp, Thr28e:Ser, Ile34:Asn and Gln96:Trp. The germline configuration protein of the anti-VIP L chain was constructed by introducing the required 4 mutations as described previously [12]. The purified germline protein expressed catalytic activity as detected by cleavage of the Pro-Phe-Arg-MCA substrate at about 3.5 fold lower level than the mature L chain (330±23 FU/0.4 $\mu$M L chain/20 min; substrate conc. 50 $\mu$M). The data suggest that remote effects due to the somatically mutated residues are not essential for expression of the catalytic activity.

The present invention provides novel compositions and methods for stimulating production of catalytic antibodies and fragments thereof. Catalytic antibodies with specificity for predetermined disease-associated antigens provide a valuable therapeutic tool for clinical use. Provided herein are methods for identifying, isolating and refining naturally occurring catalytic antibodies for the treatment of a variety of medical diseases and disorders, including but not limited to infectious, autoimmune and neoplastic disease. Such catalytic antibodies will also have applications in the fields of veterinary medicine, industrial and clinical research and dermatology.

SUMMARY OF THE INVENTION

According to one aspect of the invention, methods and compositions are provided herein for stimulating catalytic antibody production to predetermined target antigens, including but not limited to those involved in pathogenic and neoplastic processes. Covalently reactive antigen analogs (CRAAs) are described which stimulate the production of catalytic antibodies with therapeutic value in the treatment of a variety of medical conditions, including autoimmunity disorders, microbial diseases, lymphoproliferative disorders and cancer. The catalytic antibodies of the invention may also be used prophylatically to prevent certain medical disorders, including but not limited to septic shock, systemic inflammatory disease and acute respiratory distress syndrome.

The covalently reactive antigen analogs, (CRAAs) of the present invention contain three essential elements and have the following formula: X1-Y-E-X2. E is an electrophilic reaction center designed to react covalently with nucleophilic side chains of certain amino acids; Y is a basic residue (Arg or Lys) at the PI position (first amino acid on the N-terminal side of the reaction center); and X1 and X2 comprise three to ten flanking amino acids on the N-terminal and C-terminal side of the reaction center. The resultant CRAA represents a novel combination of individual structural elements which act in concert to (a) bind chemically reactive serine residues encoded by the germline genes for certain serine protease types of catalytic antibodies (as well as residues such as Thr and Cys that might acquire their chemical reactivity via somatic sequence diversification of the germline genes); (b) utilize ion pairing and noncovalent forces to bind structures such as positively charged Asp/Glu residues that are responsible for the basic residue cleavage specificity of the germline encoded catalytic sites; and (c) bind antibody combining sites at multiple amino acids via ion pairing and noncovalent forces.

In one aspect of the invention, CRAAs are administered to a living organism under conditions whereby the CRAAs stimulate production of specific catalytic antibodies. The catalytic antibodies are then purified. Antibodies so purified are then adminstered to a patient in need of such treatment in an amount sufficient to inactivate antigens associated with a predetermined medical disorder.

According to another aspect of the present invention, methods and compositions are disclosed for administering immunogenic amounts of CRAAs combined with an immunogenic amount of a conventional transition state analog (TSA) to further stimulate catalytic antibody production.

According to another aspect of the present invention, a method is provided for treating a pathological condition related to the presence of endogenously expressed catalytic antibodies. Examples of such abnormal pathological conditions are certain autoimmune disorders as well as lymphoproliferative disorders. The method comprises administering to a patient having such a pathological condition a pharmaceutical preparation comprising covalently reactive antigen analog capable of irreversibly binding the endogenously produced catalytic antibodies, in an amount sufficient to inhibit the activity of the antibodies, thereby alleviating the pathological condition. In this embodiment, the CRAA contains a minimal B epitope only to minimize the immunogenicity of the CRAA.

According to another aspect of this invention, a pharmaceutical preparation is provided for treating a pathological condition related to the presence of endogenously produced catalytic antibodies. This pharmaceutical preparation comprises a CRAA in a biologically compatible medium. Endogenously produced catalytic antibodies are irreversibly bound and inactivated upon exposure to the CRAA. The preparation is administered an amount sufficient to inhibit the activity of the catalytic antibodies.

In another aspect of the invention, methods for passively immunizing a patient with a catalytic antibody preparation are provided. Catalytic antibodies are infused into the patient which act to inactivate targeted disease associated antigens. In an alternative embodiment, should the patient experience unwanted side effects, the activity of the infused catalytic antibodies may be irreversibly inactiviated by administering the immunizing CRAA to said patient. Again, the immunogenicity of the CRAA in this embodiment would be reduced via the inclusion of a minimally immunogenic B cell epitope. A T cell universal epitope would be omitted in this CRAA.

In yet an alternative embodiment, the catalytic antibodies of the invention may be coadministered with antisense oligonucleotides to p53. Such combined therapy should prove efficacious in the treatment of cancer.

In yet another aspect of the invention, active immunization of patients is achieved by administering the CRAAs of the invention in a CRAA-adjuvant complex to a patient to be immunized. At least 2 subsequent booster injections of the CRAA-adjuvant complex at 4 week intervals will also be adminstered. Following this procedure, the patient' sera will be assessed for the presence of prophylactic catalytic antibodies.

The methods and CRAAs of the present invention provide notable advantages over currently available compounds and methods for stimulating catalytic antibodies specific for predetermined target antigens. Accordingly, the disclosed compounds and methods of the invention provide valuable clinical reagents for the treatment of disease.

BRIEF DESCRIPTION OF THE DRAWINGS

FIGS. 19A and 19B depict a list of antigens targeted by conventional monoclonal antibodies showing clinical promise. Such antigens are suitable targets for the catalytic antibodies of the present invention.

DETAILED DESCRIPTION OF THE INVENTION

Figure 1:
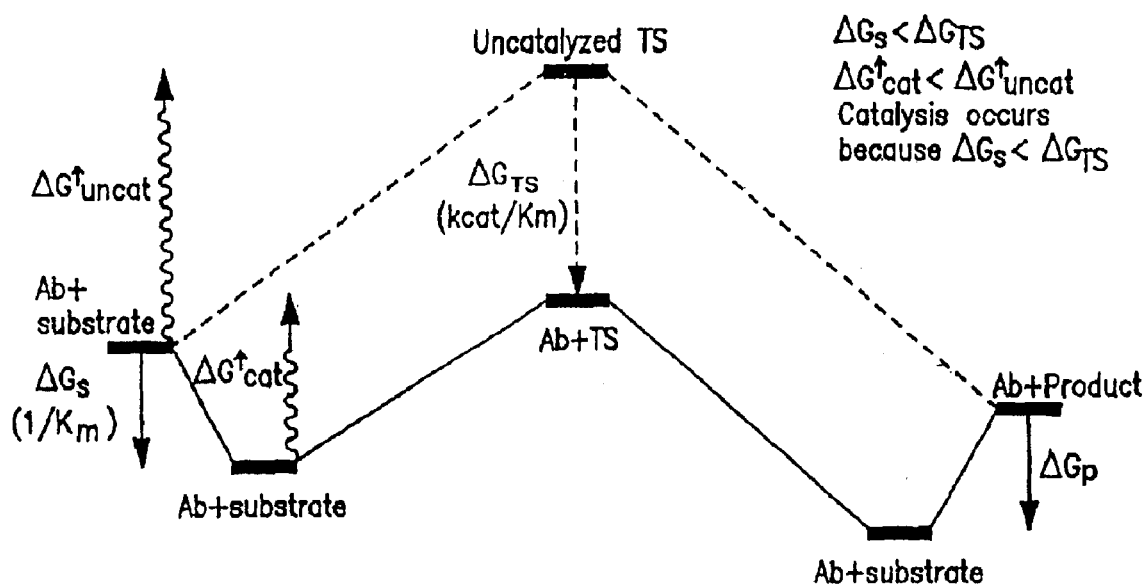
FIG. 1 is a free energy diagram for antibody catalysis involving stabilization of the substrate ground state ($\Delta G_S$) and transition state ($\Delta G_{TS}$). $\Delta G^+_{uncat}$ and $\Delta G^+_{cat}$ correspond to activation energies for the uncatalyzed and catalyzed reactions, respectively. Km is a function of the extent of ground state stabilization ($\Delta G_S$). Kcat/Km is a function of the extent of transition state stabilizatin relative to the catalyst-substrate ground state complex. $\Delta G_P$ is the product ground state.

Methods are disclosed for stimulating synthesis of catalytic antibodies of predetermined specificity by the immune system. In one embodiment of the invention compositions and methods are provided for the generation of catalytic antibodies to a peptide antigen of choice. In another embodiment, compositions and methods are provided which are useful in passive immunotherapy modalities for the treatment of cancer and other medical conditions. Catalytic antibodies for treatment of disorders in which TNFα and ILβ1 play a key role are also contemplated for use in the present invention. Such disorders include, but are not limited to, ischemia and reperfusion injury, septic shock, SIRS, acute respiratory distress syndrome, rheumatoid arthritis, inflammatory bowel disease, multiple schlerosis and neurotrophic pain.

In another embodiment of the invention, vaccination protocols are described which elicit catalytic Ab production to predetermined viral or pathogenic antigens. The covalently reactive antigen analogs disclosed preferentially stimulate the production of catalytic antibodies. Such antibodies provide superior protection against infection due to the presence of catalytic action against the target antigen which results in its permanent inactivation. Additionally, a single catalytic Ab molecule may be reused to inactivate multiple antigen molecules as compared to noncatalytic Abs which bind antigen reversibly and stoichiometrically.

Immunization with TSAs [1] has been proposed as a means to derive Abs that can bind the transition state, and thus lower the activation energy barrier for the reaction. The commonly used phosphonate analogs contain a tetrahedral phosphorous atom and a negatively charged oxygen atom attached to the phosphorous. Formation of the transition state of peptide bond cleavage is thought to involve conversion of the trigonal carbon atom at the cleavage site to the tetrahedral state, and acquisition of a negative charge by the oxygen of the carbonyl group. The conventional phosphonate TSAs may induce, therefore, the synthesis of Abs capable of binding the oxyanion structure and the tetrahedral configuration of the transition state. However, Abs to these TSAs, while capable of accelerating comparatively undemanding acyl transfer reactions, cannot effectively catalyze peptide bond cleavage. An antibody to a phosphinate TSA has recently been reported to slowly cleave a stable primary amide [11]. It is possible that the anti-phosphinate Ab may permit superior transfer of a proton to the amide nitrogen at the scissile bond, compared to the more common anti-phosphonate Abs, which might account for its better catalytic activity.

Most enzymologists hold that phosphonate TSAs fail to elicit efficient catalytic Abs because they are poor transition state mimics, and because multiple transition states are involved. Enzymes use activated amino acid sidechains to catalyze peptide bond cleavage. For instance, the Ser hydroxyl group acquires enhanced nucelophilicity and the capability to mediate covalent catalysis due to formation of an intramolecular, hydrogen bonded network of the Ser, His and Asp residues. The phosphonate analogs do not contain structural elements necessary to bind the nucleophilic reaction center. Induction of the covalent catalysis capability in Abs is therefore unattainable using conventional phosphonate TSAs. Further, these TSAs do not exploit the existence of the germline encoded, serine protease site in Abs.

Methods are disclosed for the preparation of electrophilic CRAAs which are capable of reacting with the nucleophilic serine residue of the catalytic Abs. These novel antigen analogs will be applied to select catalysts from the antibody libraries. The logical extension of this strategy is to force the utilization of the serine protease sites for the synthesis of antibodies specific for individual target antigens, such as the EGFR. This can be achieved by immunization with the aforementioned electrophilic CRAAs. Such CRAAs promote clonal selection of B cells expressing the germline encoded serine protease sites on their cell surface. Further, the specificity for EGFR, for example, will be ensured by incorporating an appropriate antigenic epitope from EGFR which will flank the covalently reactive antigen analog structure.

Catalytic Ab synthesis has been documented in autoimmune disease [2, 4]. Further, the immune system is capable of producing Abs that catalyze the cleavage of exogenous antigens, including the cleavage of HIV protein gp120. However, patients infected with the virus do not mount a catalytic Ab response to gp120. The HIV CRAAs discussed herein will force the immune systme to synthesize protective catalytic antibodies to HIV. Data are presented herein which support this approach. gp120 has been selected as the target antigen for the following reasons: (a) It is an essential constituent of HIV-1 for productive infection of host cells; (b) As a virus-surface protein, gp120 is readily accessible to Abs; and (c) Certain anti-gp120 Abs have been shown to arrest HIV infection.

The catalyst VL genes can be recruited for the synthesis of HIV-specific catalytic Abs, by immunization with the CRAAs of the present invention. The analogs are capable of binding the nucleophilic, germline encoded catalytic site, and therefore, preferentially stimulate the clonal expansion of B cells producing the catalytic Abs. When necessary, phosphonate TSAs can be combined with CRAAs to induce catalytic antibodies that contain an oxyanion hole in addition to nucleophillic chemical reactivity.

CRAAs reactive with the key structural elements of serine protease-like catalysts will be synthesized which contain a model B cell epitope of gp120 involved in CD4 binding (residues 421–436). Autoimmune and non-autoimmune mice wil be immunized with the B epitope and its CRAA using procedures well known to those of skill in the art. A T helper epitope will also be incorporated in the CRAA. Individual structural features known to contribute in serine protease catalysis, i.e., a nucleophilic serine residue, an oxyanion hole forming residues, shape complementarity with the tetrahedral geometry of the scissile bond, and recognition of flanking residues in the substrate will be recruited in the elicited antibodies by incorporating the following features in the TSAs: an electrophilic, tetrahedral phosphonate ester or a negatively charged phosphonate flanked by the B epitope residues.

The CRAAs of the invention and the resulting catalytic antibodies have at least three major applications. The first application is directed to the generation of catalytic antibodies in either humans or animals following immunization with a CRAA designed for a particular medical disorder. The catalytic antibodies so generated would then be administered to patients to inactivate targeted antigen moieties. In this scenario, should the patient experience adverse side effects, the immunizing CRAA may be administered to irreversibly inactivate the catalytic antibody. The CRAAs in this embodiment would be synthesized with a B cell epitope only in order to minimize immunogenicity.

In the second application, CRAAs may be administered to patients for the purposes of actively immunizing the patient against particular pathological to generate a state of protective immunity. These CRAAs would be administered as a CRAA-adjuvant complex.

Finally, the CRAAs of the invention may be administered to patients who are currently expressing catalytic antibodies in association with a medical disorder such as autoimmune disease or multiple myeloma. CRAAS may be designed with specifically react with the antibodies present. Inhibition of catalytic function should result in an amelioration of the disease state. Again, these CRAAs are designed to contain a minimally immunogenic B cell epitope only.

The detailed description set forth below describes preferred methods for practicing the present invention. Methods for selecting and preparing CRAAs, stimulating the production of catalytic antibodies to predetermined disease antigens are described, as well as methods for administering the CRAAs or catalytic antibodies in vivo.

I. Selection and Preparation of CRAAs

The covalently reactive antigen analogs of the invention are prepared using conventional organic synthetic schemes. The novel CRAAs of the invention contain an electrophilic center flanked by peptide residues derived from proteins associated with a particular peptide antigen to be targeted for cleavage and the intended use of the CRAA.

Selection of suitable flanking amino acid sequences depends on the particular peptide antigen targeted for cleavage. For example, viral coat proteins, certain cytokines, and tumor-associated antigens contain many different epitopes. Many of these have been mapped using conventional monoclonal Ab-based methods. This knowledge facilitates the design of efficacious covalently reactive antigen analogs useful as catalytic antibody inhibitors as well as inducers of catalytic antibodies with catalytic activities against predetermined target antigens.

The amino acids flanking the reaction center represent the sequence of the targeted epitope in defined polypeptides that play a role in disease, or to which autoantibodies are made in disease.

The structural features of the CRAAs are intended to permit specific and covalent binding to immature, germline encoded antibodies as well as mature antibodies specialized to recognize the targeted epitope. Based on the tenets of the clonal selection theory, the CRAAs are also intended to recruit the germline genes encoding the catalytic antibodies for the synthesis of mature antibodies directed towards the targeted epitope.

Polypeptides to be targeted include soluble ligands and the membrane bound receptors for these ligands.

Microbial proteins are also intended to targeted for catalysis by the antibodies of the present invention. These include but are not limited to gp120, gp160, Lex1 repressor, gag, pol, hepatitis B surface antigen, bacterial exotoxins (diptheria toxin, *C. tetani* toxin, *C. botulinum* toxin, pertussis toxin).

Neoplastic antigens will also be incorporated into therapeutically beneficial CRAAs. These include but are not limited to EGF, TGFα, p53 products, prostate specific antigen, carcinoembryonic antigen, prolactin, human chorionic gonadotropin, c-myc, c-fos, c-jun, p-glycoproteins, multidrug resistance associated proteins, metalloproteinases and angiogenesis factors.

Receptors for neoplastic antigens will also be targeted for antibody-mediated catalysis. These include EGFR, EGFR mutants, HER-2, prolactin receptors, and steroid receptors.

Inflammatory mediators are also suitable targets for catalysis. Exemplary molecules in this group include TNF, IL-1beta, IL-4 as well as their cognate receptors.

Preexisting catalytic antibodies are found in autoimmune disease and lymphoproliferative disorders. The harmful actions of these catalytic antibodies will be inhibited by administering CRAAs to patients. CRAAs designed to be weakly immunogenic will be administered which covalently interact with antibody subunits with specificity for VIP, Arg-vasopressin, thyroglobulin, thyroid peroxidase, IL-1, IL-2, interferons, proteinase-3, glutamate decarboxylase.

For maximum selectivity, the flanking peptide sequences comprise an epitope which is targeted for cleavage. For example, an epitope present in the epidermal growth factor receptor is incorporated in a CRAA of the present invention. In another embodiment of the invention, an epitope present in HIV gp120 is incorporated into a CRAA. An explary CRAA for the treatment of HIV infectin comprises both a B cell epitope and a T cell epitope to maximize the immunogenicity of the CRAA. Other CRAAs exemplified herein include those suitable for generating catalytic antibodies to TNF and IL-1β.

II. Administration of CRAAs

CRAAs as described herein are generally administered to a patient as a pharmaceutical preparation. The term "patient" as used herein refers to human or animal subjects.

The pharmaceutical preparation comprising the CRAAs of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of CRAAs in the chosen medium will depend on the hydrophobic or hydrophilic nature of the medium, as well as the other properties of the CRAA. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the CRAA to be administered, its use in the pharmaceutical preparation is contemplated.

Conventional immunization methods will applied to induce catalytic Ab synthesis. Three intraperitoneal and one intravenous injections of the immunogens (about 100 μg peptide each) will be administered. The final immunization will be carried out intravenously. RIBI will be used in the animal studies. For human use, alum will be employed as the adjuvant. Alum is approved for human use and has previously been shown to provoke Ab synthesis to a B-T epitope similar to those proposed in the present invention. RIBI is a low toxicity replacement for Freund's Complete Adjuvant, and reproducibly facilitates good Ab responses to a variety of Ags. Analysis of two adjuvants is advantageous because the quality and magnitude of Ab responses to vaccines can be influenced by adjuvants, via effects of the cytokines and TH subpopulations recruited by the adjuvants on B.

CRAAs may be administered parenterally by intravenous injection into the blood stream, or by subcutaneous, intramuscular or intraperitoneal injection. Pharmaceutical preparations for parenteral injection are commonly known in the art. If parenteral injection is selected as a method for administering the molecules of the invention, steps must be taken to ensure that sufficient amounts of the molecules reach their target cells to exert a biological effect.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation comprising the CRAA may be administered at appropriate intervals, for example, twice a day until the pathological symptoms are reduced or alleviated, after which the dosage may be reduced to a maintenance level. The appropriate interval in a particular case would normally depend on the condition and the pathogenic state sought to be treated in the patient.

III. Administration of Catalytic Antibodies

The catalytic antibodies described herein are generally administered to a patient as a pharmaceutical preparation.

The pharmaceutical preparation comprising the catalytic antibodies of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of catalytic antibodies in the chosen medium will depend on the hydrophobic or hydrophilic nature of the medium, as well as the other properties of the catalytic antibodies. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the catalytic antibody to be administered, its use in the pharmaceutical preparation is contemplated.

Conventional passive immunization methods will be employed when administering the catalytic antibodies of the invention. In a preferred embodiment, Abs will be infused intravenously into the patient. For treatment of certain medical disorders, steps must be taken to ensure that sufficient amounts of the molecules reach their target cells to exert a biological effect. The lipophilicity of the molecules, or the pharmaceutical preparation in which they are delivered may have to be increased so that the molecules can arrive at their target locations. Furthermore, the catalytic antibodies of the invention may have to be delivered in a cell-targeted carrier so that sufficient numbers of molecules will reach the target cells. Methods for increasing the lipophilicity and targeting of therapeutic molecules, which include capsulation of the catalytic antibodies of the invention into antibody studded liposomes, are known in the art.

The catalytic antibodies that are the subject of the present invention can be used as antibody fragments or whole antibodies or they can be incorporated into a recombinant molecule or conjugated to a carrier such as polyethylene glycol. In addition any such fragments or whole antibodies can be bound to carriers capable of causing the transfer of said antibodies or fragments across cell membranes as mentioned above. Carriers of this type include but are not limited to those described (Cruikshank et al. in the Journal of Acquired Immune Deficiency Syndromes and Human Retrovirology, March 1997).

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. For example, the half-life of syngeneic IgG in the human is about 20 days. Over this period, 60,480 Ag molecules will be cleaved by one molecule of an antibody with a turnover of 2.1/min (which is the turnover of a human anti-VIP L chain isolated from a phage display library [14]. It can be seen, therefore, that the peptidase antibodies can express considerably more potent antigen neutralizing activity than stoichiometric, reversibly-binding molecules. Note that the antibody light chains discussed here were selected based on their antigen-binding affinity, a procedure that favors tight binding to the antigen, but will not select catalysts with the best turnover. Antibodies produced by immunization with CRAAs and isolated by appropriate selection methods, as disclosed here, will express considerably greater turnover. Such catalytic antibodies can be used to treat disease at substantially lower doses of corresponding noncatalytic antibodies.

The pharmaceutical preparation comprising the catalytic antibodies may be administered at appropriate intervals, for example, twice a week until the pathological symptoms are reduced or alleviated, after which the dosage may be reduced to a maintenance level. The appropriate interval in a particular case would normally depend on the condition and the pathogenic state sought to be treated in the patient.

CRAAs will be selected that will generate catalytic antibodies for passive or active immunotherapy that will fulfill the standard criteria for acceptable prophylatic or therapeutic agents: (1) Cleavage of the target peptide antigen by the catalytic antibody will lead to a beneficial change in a pathological process by either functionally activating or functionally inactivating the target peptide antigen; and (2) Administration of said catalytic antibodies or the induction of their production in the body by means of immunization with a CRAA will result in a favorable therapeutic index such that the clinical benefit gained outweighs the morbidity associated with andy side-effects. Discussions of how such criteria are established for the acceptability of prophylatic or therapeutic agents are common in the art can can be found in such texts as *Guide to Clinical Trials* by Bert Spilker, Raven Press, New York, 1991.

Suitable categories of prophylatic or therapeutic target peptide antigens for the practice of the present invention include but are not limited to cytokines, growth factors, cytokine and growth factor receptors, proteins involved in the transduction of stimuli intiated by growth factor receptors, clotting factors, integrins, antigen receptors, enzymes, transcriptional regulators particularly those involved in cellular program (differentiation, proliferation and programmed cell death) control, other inducers of these cellular programs, cellular pumps capable of expelling anticancer agents, microbial and viral peptide antigens.

Conventional monoclonal antibodies that act to inhibit the function of particular target molecules are among the most common type of therapeutic agent under development for clinical use by biotechnology and pharmaceutical companies. Some of these have shown substantial clincal promise and any exposed peptide target antigens that are part of the same molecular functional unit are therefore shown to be particularly well suited as potential targets for the catalytic antibodies that are the subject of the present invention. The catalytic antibodies comtmplated in the present invention will constitute a major inprovement over such conventional monoclonals becaule of their ability to affect many target molecules vs. just one and because of the resulting dramatic decrease in the cost of treatment. The availability of peptide bonds within these targeted antigens can be determined by methods well established in the art including but not limited to a demonstration of cleavage following exposure to proteolytic enzymes and catalytic light chains capable of cleaving a range of peptide bonds.

A listing of some of the antigens targeted by conventional monoclonal antibodies showing clinical promise and the corresponding medical indications are shown in FIGS. 19A and 19B.

Thus, it is an object of the present invention to provide a covalently reactive antigen analog, and a method of producing it, which is capable of 1) provoking the generation of catalytic antibodies specific to a predetermined antigen of the invention and/or 2) irreversibly inhibiting the catalytic action of catalytic antibodies associated with autoimmune disease and certain lymphoproliferative disorders. Further objects reside in providing processes for preparing antigens and their corresponding antibodies, and in providing assays and methods of using these antibodies as beneficial therapeutic agents.

EXAMPLE IA

Catalytic Antibodies for Tumor Immunotherapy

Methods for producing catalytic antibodies (Abs) suitable for treatment of cancer are described in the present example. Such antibodies offer superior immunotherapy alternatives for cancer treatment by virtue of the catalytic function, as cleavage of the target antigen should result in its permanent inactivation. Further, a single Ab molecule may be reused to inactivate multiple antigen molecules. In comparison, non-catalytic Abs bind antigen stoichiometrically, and the binding is reversible. Upon dissociation from the complex, the antigen may recover its biological functions.

The tumor-associated antigen, epidermal growth factor receptor (EGFR), will be utilized for the synthesis of an exemplary antigen suitable for stimulating the production of antibodies with enzymatic activities. Previous work on peptidase antibodies has revealed the following: 1) certain Abs are capable of combining the ability to bind individual peptide antigens with a peptide bond cleaving activity; 2) the peptidase site is structurally similar to the active site of non-AB serine proteases. This site is located in the VL domain and is encoded by a germline V domain gene(s); and 3) the synthesis of peptidase Abs occurs at increased levels in autoimmune disease.

Figure 2:
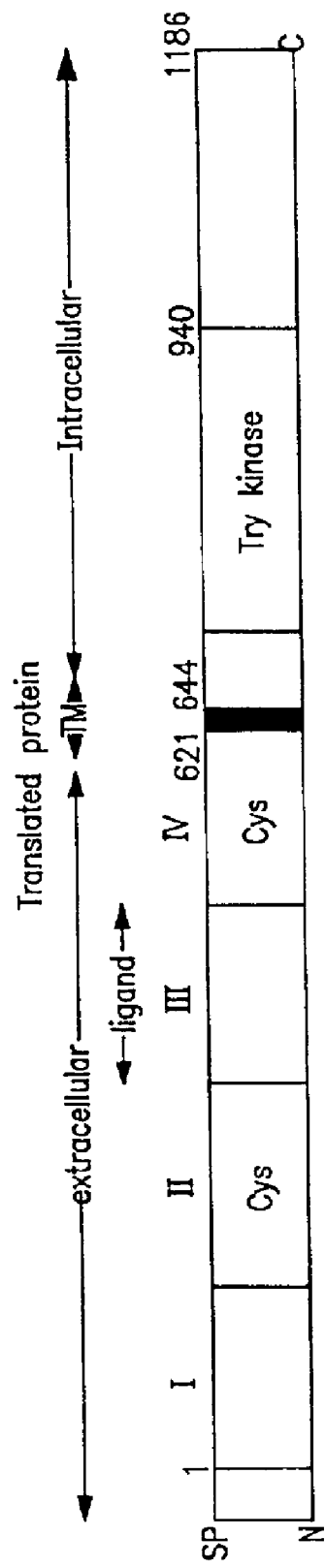
FIG. 2 is a schematic representation of the domain structure of the epidermal growth factor receptor (EGFR) protein. Ligand, ligand-binding region found mainly in domain III; TM; transmembrane domain; CYs, cysteine rich domains; and SP, signal peptide.

EGFR serves vital roles in the transduction of signals necessary for cellular differentiation and mitosis. See FIG. 2. Further, signals transduced via EGFR have been implicated in tumor invasiveness and transformation. Binding of EGF or TGFα to the EGF receptor stimulates the receptor tyrosine kinase and autophosphorylation activities. Receptor activation leads to a cascade of intracellular events which culminate in increased cell proliferation.

Overexpression of the EGFR gene has been associated with a number of neoplasms, including adenocarcinoma and squamous cell carcinoma of the lung, breast carcinoma, colon gynecological and bladder carcinoma, glioma, hepatocellular and pancreatic carcinoma and prostate carcinomas. The overexpression in some tumors has been attributed to EGFR gene amplification [15].

EGFR is a suitable tumor antigen, as it is expressed at much higher levels in tumors compared normal tissues.

Consequently, Abs to EGFR are suitable candidates for anti-tumor reagents. Many monoclonal antibodies (Mabs) to EGFR have been raised to specific epitopes of the receptor which do not compete with each other for binding EGFR [e.g., 16]. Mendelsohn and coworkers have described mouse MAbs raised using the EGF receptor protein from human A431 epidermoid carcinoma cells as the immunogen. MAbs which inhibit the binding of EGF to EGFR also inhibited the EGF-stimulated tyrosine protein kinase activity which was assayed using intact cells or solubilized membranes and an exogenous peptide substrate. Further, these MAbs inhibited the proliferation of A431 cells in tissue culture, whereas those incapable of blocking the binding of EGF to EGFR were without effect on cell proliferation. Further research showed that administration of anti-EGF receptor MAbs can inhibit tumor formation by A431 cells in athymic mice. MAbs of different isotypes have been shown to inhibit tumor growth in mice, indicating that constant domain effector functions are probably not critical in the observed antiproliferative activity. Complete inhibition of tumor growth in vivo has been observed, provided that sufficient Ab amounts were administered. The few tumors that persist continue to express EGFR, suggesting that their survival is due to inadequate exposure of the cells to the Abs [17].

Using a breast carcinoma cell line as the immunogen, Modjtahedi et al [16] generated several MAbs against EGFR, some of which blocked the binding of growth factors by EGFR and inhibited the growth of human squamous carcinoma cell lines. Several additional EGFR-specific Mabs have been prepared using purified EGF receptors or cells expressing high levels of EGFR as the immunogens [18]. Phase 1 clinical trial of anti-EGFR Abs for the treatment of malignant gliomas [19,20], head and neck cancer, and lung cancer are under way.

The data reveal that Abs capable of disrupting EGF binding to EGFR may be utilized in development of agents effective for immunotherapy of EGFR expressing tumors. An inverse correlation has been noted between EGFR expression and the levels of BCL-2, a protein that plays an important role in overriding programed cell death (apoptosis). Ligand binding by EGFR under certain conditions has been shown to protect tumor cells from c-myc induced apoptosis. Glioblastoma cells transfected with a mutant EGFR display decreased apoptosis [21]. In principle, therefore, Abs to EGFR may be capable of inducing apoptosis in tumor cells. If this possibility is valid, the likelihood of complete tumor regression via an apoptotic pathway following treatment with EGFR Abs will be strengthened.

Abs capable of cleaving EGFR comprise superior immunotherapeutic agents compared to their noncatalytic counterparts for the following reasons: (a) Cleavage of EGFR at the appropriate peptide bonds should cause permanent loss of the biological activity, whereas EGFR binding by a noncatalytic Ab can be reversible, and dissociation of the Ab will regenerate the biological functions of the EGFR; and (b) A single catalyst molecule can cleave multiple substrate molecules, whereas noncatalytic Abs can only act stoichiometrically.

Three strategies for the prepararation of catalytic Abs are disclosed herein. The first strategy capitalizes on the availability of cloned Ab light chains with peptidase activity. Previous studies have suggested that the nonspecific peptidase activity residing in the VL domain can be directed by the antigen binding specificity of the VH domain. Hybrid Fv constructs will be generated composed of an available VL domain linked to EGFR binding VH domains. Following synthesis and expression in suitable expression systems, the Fv constructs will be assessed for specific EGFR cleaving activity.

The second cloning strategy is based on the observation that certain Abs expressed in autoimmune disease utilize serine protease catalytic sites encoded by germline VL genes. Mice with an autoimmune disease background will be immunized with EGFR expressing cells. Following immunization, catalytic Fv domains will be isolated from a phage display library. Catalysts that combine the germline encoded catalytic activity with somatically acquired specificity for EGFR will selected by binding to covalently reactive antigen analogs (CRAAs) reactive with nucleophilic serine residues, followed by binding to the extracellular domain of EGFR.

The third strategy is based on the hypothesis that the immune system can be forced to utilize the germline encoded catalytic site for synthesis of Abs to EGFR. Mice will be immunized with an electrophilic CRAA of an EGFR peptide capable of preferentially stimulating catalytic Ab synthesis. The Ab catalysts so produced will be assessed for their inhibitory effects on the tumorigenicity of an EGFR-expressing human cell line in vivo using a variety of methods known to those of skill in the art, i.e., inhibition of EGF-stimulated EGFR autophosphorylation and inhibition of tumor cell growth.

Figure 3:
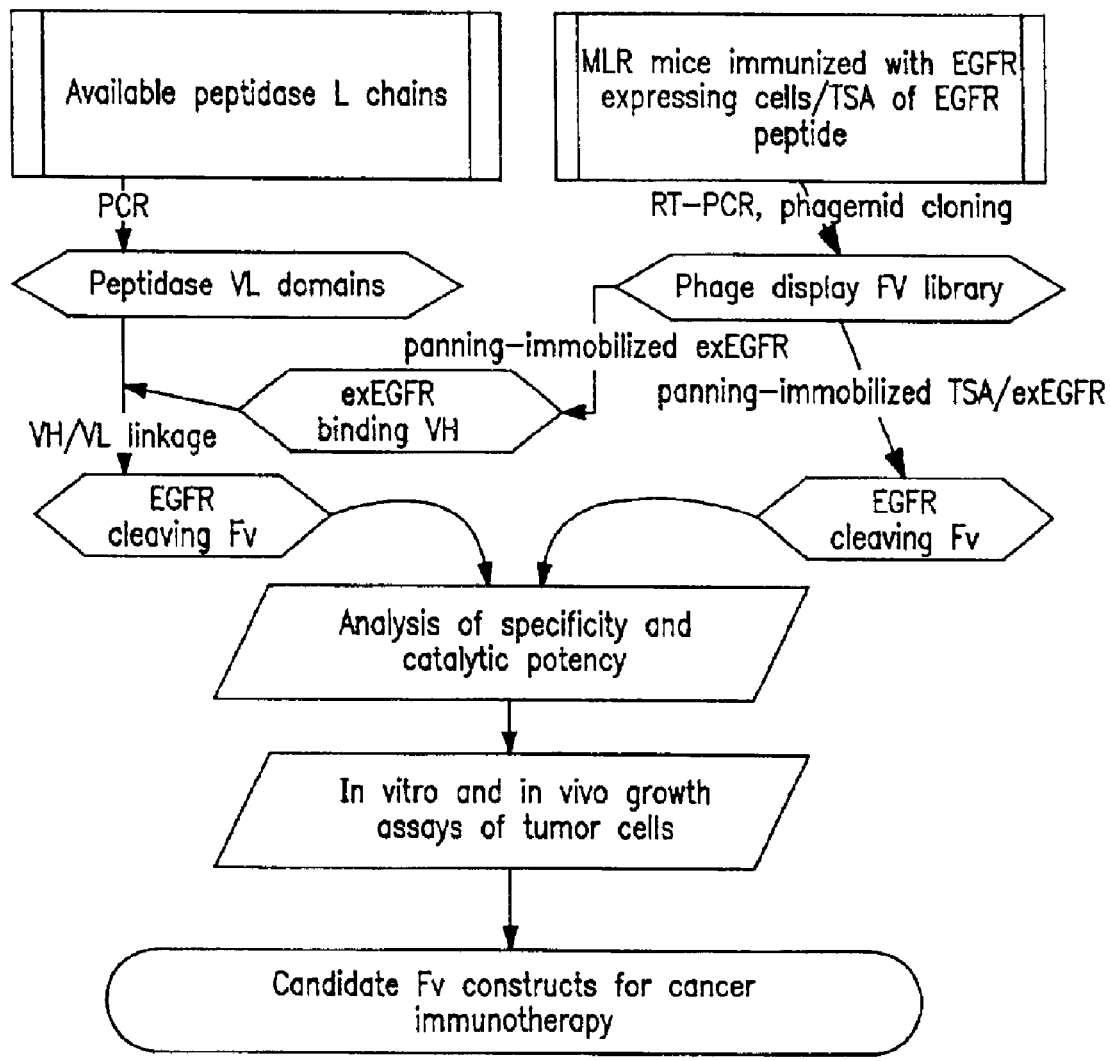
FIG. 3 is a schematic diagram of the cloning stratagies proposed for preparing anti-EGFR catalytic antibodies.

The compositions and methods disclosed herein facilitate the preparation of specific and catalytically efficient EGFR cleaving antibodies suitable for cancer immunotherapy. FIG. 3 summarizes the approach to be taken. Previous studies have established the feasibility of isolating Abs capable of catalyzing the cleavage of certain Ags, i.e., VIP, thyroglobulin and gp120. Information from these studies has been applied in the present invention resulting in the disclosed strategies for preparing catalytic Abs to EGFR.

The following materials and methods are provided to facilitate the practice of the present invention.

Materials and Methods

Immunization: Six MRL/lpr mice will be hyperimmunized with EGFR expressing cells as previously described. Briefly, about $10^7$ A431 cells will be recovered by trypsinization of tissue culture flasks, resuspended in PBS and administered in RIBI adjuvant to the mice intraperitoneally. Three booster immunizations using about $5 \times 10^6$ cells will be carried out at ten day intervals. If high level Ab titers are not reached, booster injections with the soluble extracellular domain of the epidermal growth factor receptor (exEGFR) (25 $\mu$g) will be administered. To drive the immune system to generate catalytic antibodies, six MRL/lpr mice will be hyperimmunized i.p. with the TSA-EGFR conjugated to keyhole limpet hemocyanin (KLH) (50 $\mu$g protein) in RIBI according to the above scheme. Blood will be obtained from the retro-orbital plexus at ten day intervals.

Expression and purification of exEGFR: The extracellular domain of EGFR (exEGFR, composed of residues 1–621 of EGFR) will be purified from a baculovirus expression system as previously described [22]. Expression of the exEGFR is done in Sf9 insect cells, which secrete about 2 mg/ml of the exEGFR into the culture supernatant [22]. Purification by a two step ion exchange chromatography procedure, permits recovery of the protein at about 95% homogeneity, as determined by SDS-PAGE [22].

Figure 4:
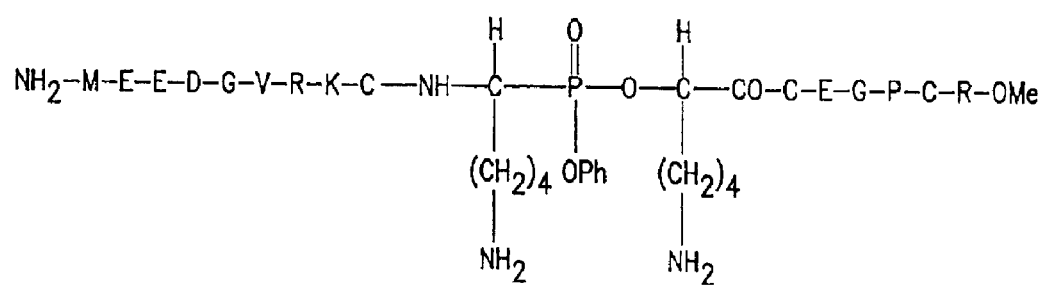
FIG. 4 depicts the structure of the CRAA-EGFR peptide.

Preparation and purification of EGFR-CRAA peptide: The CRAA is composed of three basic elements: an electrophilic phosphonate ester flanked on the N terminal side by EGFR residues 294–303 and on the C terminal side by EGFR residues 304–310. See FIG. 4. The electrophilicity resides on the phosphorous atom, and is intended to trap nucelophilic serine residues present in Abs. The basic synthesis scheme for synthesis of such CRAAs has been described [23]. Briefly, a phosphinate containing isostere of lysine (EGFR residue 303) is attached to the appropriate flanking peptide sequence. The isostere will be prepared from the diphenylmethylamine salt of hypophosphorous acid and 6-aminohexanal, followed by removal of the diphenylmethyl group in acid [24]. The required flanking peptides are prepared by conventional solid phase peptide synthesis, except that the peptide corresponding to EGFR residue 304–310 contains 2-hydroxy-6-aminohexanoic acid instead of the N terminal lysine. Side chain protected peptides will be attached to the phosphinate structure by classical solution phase peptide synthesis methods. The phosphinate structure will be converted to the phosphonate phenyl ester by oxidative coupling with phenol. The N terminus of the side chain protected CRAA-EGFR peptide will be coupled to KLH by the glutaraldehyde method. The reaction mixture will be separated by gel filtration, and residual unconjugated peptide in the lower molecular fractions will be analyzed for inorganic phosphorous after complete digestion with perchloric acid. This will permit estimation of the conjugation efficiency.

exEGFR and EGFR-CRAA ELISA: exEGFR or CRAA-EGFR (100 ng/ml) will be coated on PVC 96 well plates, excess protein binding sites blocked with 5% albumin, and binding of appropriately diluted serum Abs to the immobilized antigens will be measured. The extent of the reaction is measured by treatment with goat anti-mouse IgG tagged to peroxidase. Controls include the incubation with preimmune sera and with excess soluble competitor exEGFR. The procedure for measuring exEGFR and CRAA-EGFR binding by cloned Fv constructs is essentially as above, except that the reaction is visualized by treatment with mouse anti-c-myc Ab (the recombinant proteins contain a 10 residue c-myc tag) and anti-mouse IgG tagged to peroxidase.

Figure 5:
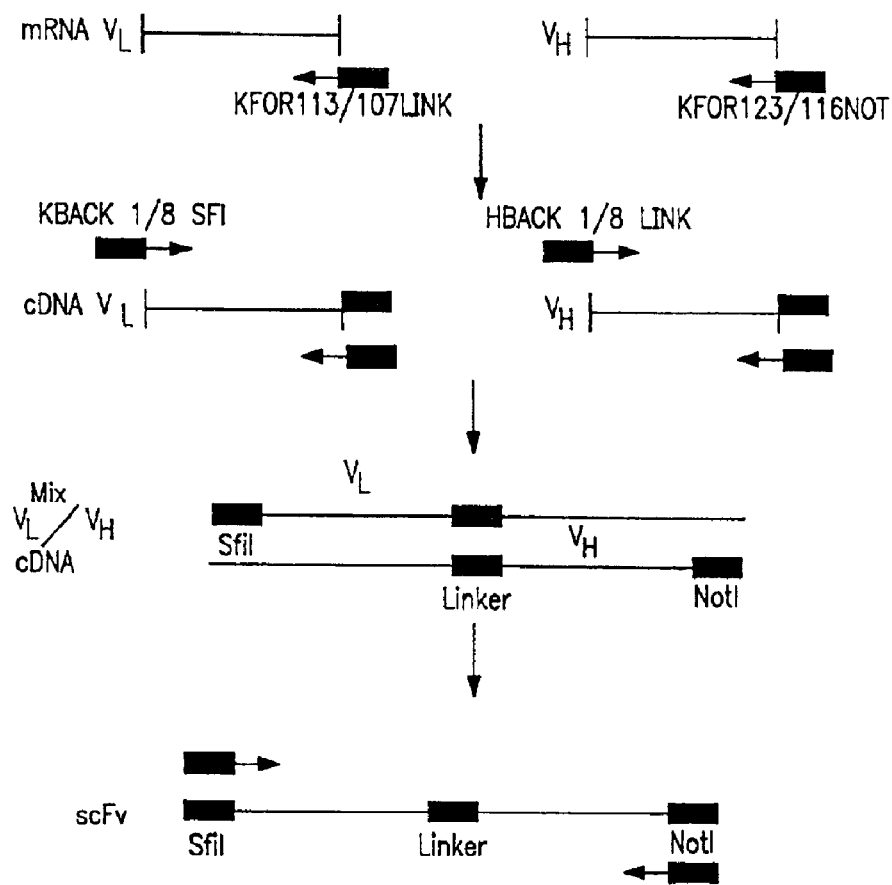
FIG. 5 is a diagram depicting Fv construction by overlap extension.

Fv preparation: The methods described in previous publications [10,14,25] with certain adaptations will be applied, as summarized below. See also FIG. 5. Construction of an Fv cDNA library will be done as follows: Total RNA is prepared by standard methods from the splenocytes of immunized mice while minimizing RNase contamination. Libraries of VL cDNA (residues 1–113) and VH cDNA (residues 1–123) will be produced from the RNA template using reverse transcriptase and appropriate VL or VH forward primers, which contain, respectively, an SfiI restriction site for cloning into the vector and an antisense sequence encoding a peptide linker. The cDNA is amplified by PCR using Taq, dNTPs and appropriate primers as shown in FIG. 5. The back primers are based on sequences coding for conserved N-terminal amino acids in the FR1 regions. Limited degeneracy has been introduced in the primers to allow amplification of closely related V-gene families (e.g., K families 2,3,6). 6 back VL primers, 8 VH back primers, 1 VL forward primers and 2 VH forward primers are needed. The forward primers are designed to anneal to constant region sequences close to the 3' end of the V domain [26]. The VH and VL back primers contain a NotI site for cloning and a sense sequence encoding the linker. The linker is a 14-residue, flexible peptide. SfiI and NotI sites are rare cutters, minimizing loss of library diversity at the restriction digestion step. Following completion of the PCR, the amplified cDNA bands of the correct size are cut from agarose gels, extracted using Geneclean II (BIO 101) and quantitated by EtBr fluorescence ($\lambda$em 590 nm, $\lambda$ex 302 nm). The VL and VH cDNA species are linked by overlap extension, i.e., annealing of linker sense and antisense sequences, and filling in of the two strands with Taq. Individual cDNA species are purified by agarose gel electrophoresis and Wizard kits (Promega) prior to performing the linkage reaction.

Cloning and phage display: The library will then be cloned into the phagemid vector pCANTABhis$_6$ [27]. The vector contains the following sequence elements: restriction sites, a signal peptide, a gene3 structural peptide, a stop codon (amber) between the insert and gene3, a c-myc peptide tag, poly(his)$_6$, an IPTG-inducible lac promoter and an ampicillin resistance gene. The amber codon permits secretion of soluble V domains or their expression as p3-fusion proteins on the phage surface, depending on the host strain (HB2151 cells recognize amber as a stop and TG1 cells recognize amber as Glu). The cDNA and the vector are digested sequentially with SfiI and NotI followed by ligation using T4 DNA ligase. Host cells are transformed by electroporation, clones are selected in kanamycin and the presence of inserts in individual colonies is confirmed by PCR using primers located in the vector upstream and downstream of the insert, yielding EtBr-stained bands at 0.7 kb. Addition of helper phage (VCSM13) permits packaging of phage particles from TG1 cell cultures. The particles in the supernatant of the culture are precipitated twice with 4% PEG, yielding phage ready for the selection procedures described below.

Selection of EGFR binding Fv: exEGFR will be coated on polystyrene plates at a concentration of about 5 $\mu$g/ml in PBS. Following removal of unbound protein and saturation of nonspecific protein binding sites, the plates are incubated with the phage preparations. Unbound phage will be removed by extensive washing and bound phage particles will be eluted using a pH 3.0 buffer.

Catalytic VL domain and hybrid Fv library: The hybrid Fv libraries will be prepared by linking a VL domain already established to possess catalytic activity (clone U24 [15]) isolated from an unimmunized mouse to VH domains from the EGFR-binding Fv library. The VL domain cDNA will be reamplified by PCR as above, except that the forward primer will contain a NotI site for direct cloning into the vector. The VH domains will be reamplified from the EGFR binding Fv cDNA library using VH primers described above, except that the forward primer contains a linker antisense sequence. VL/VH linkage will be as above.

Soluble Fv expression and purification: Phagemid DNA from selected clones is grown in HB2151 cells. Periplasmic extracts contain 2–10 mg/l of the recombinant protein. Chromatography is on Ni-Sepharose (Qiagen). Unbound proteins are removed with a 0.5 M NaCl buffer. Recombinant antibodies are eluted at pH 5 or with imidazole. A second round of metal affinity chromatography provides pure recombinant proteins, assessed by SDS-electrophoresis, isoelectric focusing, Mono-Q chromatography and N-terminal amino acid sequencing. Each batch of purified protein is analyzed by gel filtration (Superose 12 column) and by immunoadsorption with immobilized anti-c-myc Ab [14] to confirm that the catalytic activity belongs to the Ab fragments. Chromatographic procedures are conducted using a gradient FPLC system. Amino acid sequencing is done using blots of electrophoresis gels by the Protein Structure Core Facility at the University of Nebraska Medical Center.

Figures 6A, 6B:
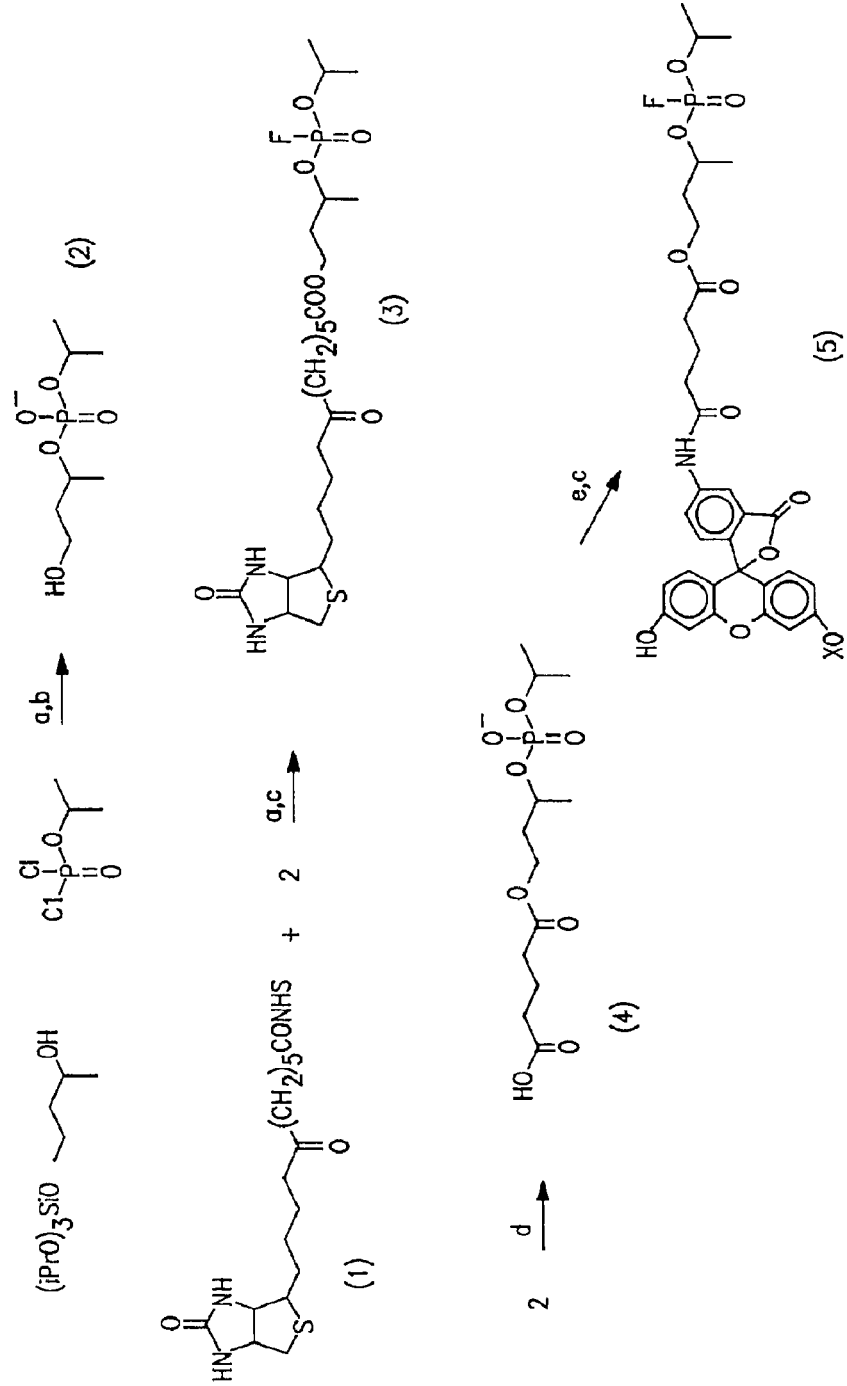
FIG. 6 shows a schematic diagram of the immobilization of a serine protease reactive fluorophosphate transition state analog. (a) triethylamine, CH2C12; (b) water, THF; (c) DAST; (d) glutaric anhydride, pyridine; (e) DCC, DMAP, triethylamine, fluorescein.

Catalyst selection reagents: Two compounds capable of covalent reactions with nucleophillic serine residues will be prepared. The first compound, a fluorophosphate (FP) bifunctional reagent, is similar to the serine protease inhibitor DFP shown in previous studies to inhibit the catalytic activities of Abs. Because of the poor stability of DFP in water, its direct attachment to a solid support for phage adsorption is impractical. A bifunctional reagent containing an FP group conjugated to an affinity tag like biotin will be employed which will permit immobilization of the conjugate on avidin coated solid phase. The FP ester will be reacted with biotin activated with N-hydroxysuccinimide (NHS-LC biotin II, Pierce Chemical Co., 1 in FIG. 6, which also introduces a long spacer to minimize steric hindrance effects. The synthesis will proceed by esterification of phosphate diester 2 with NHS-LC biotin II (1). Compound 2 will be obtained by phosphorylation of 4-triisopropylsilyloxy-2-butanol with dichloroisopropyl phosphate followed by hydrolysis and deprotection of the monochlorophosphate intermediate. Conversion to the fluorophosphate 3 will be accomplished at the final step by treatment with diethylaminosulfuryl trifluoride (DAST). Reagent 3 shall by kept in dioxane or other organic solvent to mitigate possible autoreactivity. An aliquot of the organic solution will then be transferred into an aqueous solution containing phage to give an effective concentration of 0.1 to 0.5 mM of 3. In the event that the chemical autoreactivity of reagent 3 is too severe for practical application we will consider a fluorescein tag as an alternative to biotin. Fluorescein contains a phenolic OH and a carboxylic ester which should be compatible with the fluorophosphate. Fluorescein will be acylated with the phosphate derivative 4 (obtainable by treatment of 2 with glutaric anhydride) to form an amide linkage to its aniline group. Fluorination at phosphorus to obtain 5 will be achieved by treatment with DAST. See FIG. 6.

A peptide aldehyde matrix will also be prepared as a means to trap serine protease sites. The commercially available arginal-containing ligand antipain (N—[—N-carbonyl-Arg-Val-Arg-al]-Phe) will be activated with carbodiimide and linked covalently via the carboxyl group of the Phe residue to the amino residues of AH-Sepharose 4B (Pharmacia). The synthesis methods are routine, and have been detailed by Pharmacia.

Catalytic Fv Selection: The Fv phage library will be passed through the immobilized serine protease trapping reagent described above. Unbound phage will be removed by extensive washing. Elution of bound phage will be done with 0.1 M glycine-HCl, pH 2.2, which is sufficient to disrupt biotin-avidin and fluorescein-antifluorescein interactions. Elution could also be done using 0.1–1M hydroxylamine to dissociate the phosphate-serine linkage. Elution of the peptide aldehyde matrix will be done with weakly acidic buffer (pH 4.5), which favors breakdown of the hemiacetal adduct. Phage particles recovered from the serine protease binding matrix will be amplified by growth in TG1 cells and then subjected to selection for binding to immobilized exEGFR as described above for selection of EGFR binding Fv.

Screening for catalytic activity: Fv fragments will be screened for cleavage of exEGFR, the CRAA-EGFR peptide and a nonspecific peptidase substrate, Pro-Phe-Arg-methylcoumarinamide (MCA). A protocol has been developed to rapidly purify large numbers of Ab clones based on their metal binding capability. Bacterial supernatants are incubated with Ni-Sepharose in 96-well plates fitted with a nitrocellulose filter, unbound material removed by washing with neutral pH buffer, and bound V domains eluted into a catch plate using a pH 5 buffer. A Millipore Multiscreen apparatus permits rapid processing. The eluate is neutralized, and Pro-Phe-Arg-MCA (500 µM), [$^{125}$I] exEGFR or [$^{125}$I]EGFR(tyr, 294–310) (about 30,000 cpm) is added. Hydrolysis of the peptideMCA substrate is determined using a plate reader ($\lambda$ex 360 nm, $\lambda$em 470 nm; cleavage of the amide bond linking Arg to aminomethyl-coumarin produces increased fluorescence). The peptide-MCA substrate is available commercially. The EGFR(tyr, 294–310) is a 19 residue synthetic peptide corresponding to residues 294–310 of EGFR with a tyrosine residue placed at the N terminus to permit the radiolabeling with $^{125}$I. Preparation of the $^{125}$IexEGFR and [$^{125}$I]EGFR(tyr, 294–310) is by the standard chloramine-T method. Removal of free $^{125}$I is on a disposable gel filtration column or on a reversed-phase HPLC column, respectively. exEGFR cleavage is determined by nonreducing SDS-electrophoresis (4–15% gels) using a PHAST system (Pharmacia) followed by autoradiography using Kodak XAR film and quantitative scanning of band areas using the program Image. The reaction will be evident as the depletion of the 105 kD band and appearance of smaller radioactive fragments. Care is taken to only quantitate the bands lying within the linear response range of the X ray film. Cleavage of [$^{125}$I]EGFR (tyr, 294–310) will be determined by measuring the radioactivity rendered soluble in 10% trichloroacetic acid. The TCA precipitation procedure is similar to that described previously to determine VIP cleavage [3]. The method will be validated by comparison with RP-HPLC on a C-18 column. If difficulties are encountered, electrophoresis on 25% PAGE gels can be carried out to discriminate between the intact peptide and its fragments, as described previously for VIP [28]. Controls will be eluates from bacteria transformed with vector without a cDNA insert or cDNA encoding a noncatalytic Fv. Dot-blotting with an anti-c-myc Ab as described in [25] permits quantitation of the recombinant protein.

Screening for inhibition of EGF binding: The selected clones will be screened for their effect on binding of $^{125}$I-labeled EGF to A431 cells in 96 well plates using our previously published methods [15, 18]: The cells (1×10$^5$ cells/well) will be plated in the wells and allowed to adhere to the solid phase, $^{125}$I-labeled EGF (Amersham) and the Fv solutions will be added (about 1 nM), the reaction mixture incubated for 60 min, the wells washed three times in iced binding buffer, and the wells counted for bound $^{125}$I-labeled EGFR. Controls will include binding assays conducted in the absence of Fv, and in the presence of excess competitor exEGFR.

Assessment of Catalytic Properties

An immunoblotting cleavage assay will be performed to confirm that the cleavage reaction is not due to artefacts associated with radiolabeling of exEGFR. About 1 µg purified exEGFR is treated with the catalyst for an appropriate length of time followed by SDS-PAGE. The gel is blotted onto nitrocellulose and stained with polyclonal rabbit anti-exEGFR followed by anti-rabbit IgG-peroxidase. Depletion of immunostainable intact exEGFR and appearance of immunostainable exEGFR fragments will indicate exEGFR cleavage.

Kinetics: Initial rates for the Ab-catalyzed hydrolysis of radiolabeled exEGFR mixed with increasing amounts of unlabeled exEGFR are computed based on band intensities seen by SDS-electrophoresis and autoradiography. The velocity of exEGFR cleavage is determined from the intensity of the intact substrate band, and the velocities of individual reactions, from the intensity of each product band. Kinetic constants ($K_m$, $k_{cat}$) will be calculated from the rate data fitted to the Michaelis-Menten equation {v= ($V_{max}$·[S])/($K_m$+[S])}. Kinetic studies will also be conducted using synthetic exEGFR peptides as the substrate, a peptide in which only a single peptide bond is cleaved. The use of such a substrate will eliminate complexities associated with multiple simultaneous reactions. The kinetics of hydrolysis of such a substrate will be determined as described above, except that reversed-phase HPLC will be employed to separate the products. Quantitation will be by determining the area under the product peaks observed at 214 nm.

Cleavage sites: To identify the peptide bonds cleaved by Abs, electrophoretically pure exEGFR will be incubated with the catalyst for a period sufficient to produce about 100 pmoles of product fragments, the fragments will be separated by polyacrylamide gel electrophoresis, blotted onto a PVDF membrane and the immobilized proteins sequenced by N-terminal Edman's degradation at the UNMC Protein Structure Core Facility. Controls will include exEGFR incubated with an inactive Fv and exEGFR incubated without Fv. At least 5 N-terminal residues of each fragment will be identified to permit unambiguous assignment of the cleavage sites. Tryptic mapping and FAB-Mass spectrometry to identify resultant fragments will be considered if necessary, i.e., if the N-terminus is blocked.

Substrate specificity: Along with exEGFR, cleavage of the following substrate will be tested: (a) $^{125}$I-lysozyme; (b) $^{125}$I-thyroglobulin; (c) $^{125}$I-IgG; (d) $^{125}$I-VIP; and (e) various peptide-MCA conjugates. Protocols for assaying the hydrolysis of these substrates are in place. Purified human thyroglobulin, hen lysozyme (Sigma) and human IgG from serum are labeled with $^{125}$I by the chloramine-T method and purified by gel filtration [2, 4]. Following incubation of the radiolabeled proteins with the Abs, the reaction mixtures will be electrophoresed. Autoradiography will permit products to be visualized as smaller-sized bands (mass of intact thyroglobulin (monomer), lysozyme and IgG: 330 kD, 15 kD and 150 kD, respectively). VIP cleavage is measured as the amount of radioactivity rendered soluble in TCA or by RP-HPLC separations [2]. Cleavage of substrates containing MCA linked to charged (Arg, Lys, Asp), uncharged (Leu, Ala) and bulky (Phe) amino acids is measured by fluorimetry.

Isolation of Specific EGFR Cleaving Catalysts from Mice Immunized with a Covalently Reactive Antigen Analog of an EGFR Peptide As mentioned previously, catalytic Ab synthesis is increased in autoimmune disease. To derive high efficiency catalysts, the immune system will be further challenged via the immunization with a covalently reactive antigen analog, CRAA, of an EGFR peptide (CRAA-EGFR). This antigen analog is designed to increase the recruitment of the germline V gene encoded site for the synthesis of the EGFR-specific catalytic Abs. Further, the CRAA-EGFR will also select for any serine protease-like catalytic sites formed by somatic means, i.e., V/D/J rearrangement and somatic hypermutation.

The key structural features of the CRAA-EGFR are: (a) the tetrahedral, electrophilic phosphorous atom capable of binding nucleophilic serine residues in catalytic Abs; and (b) the lysine residue on the N-terminal side of the phosphorous atom capable of binding catalytic sites specialized for cleavage on the C terminal side of basic residues; and (c) ten and seven amino acids, respectively, on the N and C terminal sides of the CRAA structure, corresponding to the sequence of residues 294–310 of EGFR.

The phosphorous atom serves as the analog of the scissile peptide bond carbon atom linking residues 303 and 304 in EGFR. In the phenylester configuration shown in FIG. 4, the phosphorous atom acquires a partial positive charge, just as the scissile bond carbon atom carries the partial positive charge required for its reaction with nucleophilic serine residues. Peptidic O-phenylphosphonates have previously been described to be capable of irreversibly inactivating various serine proteases by forming a covalent bond with the oxygen atom of the active site serine residue [29]. Sampson and Bartlett [23] have established the chemical synthesis protocol to prepare the phenyl ester at the phosphorous atom, and to attach peptide sequences flanking the phosphonate ester.

It should be noted that the CRAA-EGFR described above is distinct from previous phosphonate TSAs applied to raise esterase Abs [13]. The conventional phosphonate TSAs contain an anionic oxygen attached to the phosphorous, which can bind the oxyanion hole found in the catalysts. The phosphonate TSAs, however, do not react with nucleophilic serine residues in the catalytic site.

A basic residue is incorporated at the P1 position of the CRAA-EGFR to exploit the existence of the germline encoded, basic residue-specific catalytic site in Abs. The presence of the basic residue, along with the phosphonate phenylester structure, promotes tight binding to catalytic site, and thus promotes the ability of the CRAA-EGFR to selectively stimulate the clonal proliferation of B cells synthesizing the catalytic sites.

EGFR residues 294–310 are incorporated in the CRAA-EGFR to promote synthesis of Abs with EGFR-specific catalytic activity, as opposed to nonspecific catalytic activity. This epitope has been selected because it is a component of domain III of EGFR, which is the main contributor of the residues constituting the EGE binding site [30]. See FIG. 4. Further, insertional mutagenesis at the N terminal region of this sequence is described to result in reduced EGF binding. As discussed previously, the EGF binding site is composed of non-contiguous residues. Thus, conformational disruptions caused by the intended cleavage at position 303–304 could also indirectly result in impaired EGFR function.

Fv phage display libraries will be prepared from MRL/lpr mice hyperimmunized with the CRAA-EGFR. The presence of high affinity serum Abs capable of binding the CRAA-EGFR will be measured by ELISA to confirm that the mice mount a vigorous Ab response. Fv library preparation and selection will be essentially as described [25] except that selection of phages will be carried out using the immobilized CRAA-EGFR. Screening for catalytic activity will be done as described hereinabove. The substrate will be an 18 residue peptide containing a tyrosine residue at the N terminus followed by 17 residues corresponding to positions 294–310 of EGFR. The tyrosine residue is located distant from the intended cleavage site to minimize interference with Fv recognition. In addition, screening for exEGFR cleavage will be performed using the conformational epitope of residues 294–310 as presented in the functional EGFR protein.

The binding affinity of the catalysts for CRAA-EGFR will be determined by ELISA. Inhibition of EGFR(294–310) cleavage by increasing concentrations of the CRAA-EGFR will be determined. The CRAA-EGFR will serve as a competitive alternate substrate, with Ki values close to the Kd values estimated from the binding assay.

The product fragments generated by cleavage of EGFR (294–310) and of exEGFR will be identified, permitting deduction of the cleavage site(s). If the recruitment of the catalytic activity occurs mainly because of the phenylphosphonate ester structure in the CRAA-EGFR, both substrates ought to be cleaved mainly at the peptide bond linking residues 303 and 304 (Lys-Lys bond). As discussed above, antigen specific catalysts can be synthesized by immunization with ground state antigens. Thus, catalysts capable of cleaving EGFR(294–310) at peptide bonds other the 303–304 bond should also be identified. One possible target for cleavage is found at the Arg300-Lys301 bond, as the germline encoded activity present in the preimmune repertoire recognizes basic residues.

The methods described above provide a series of high affinity, high turnover catalytic Abs that recognize and cleave EGFR at residues 303–304, and induce the loss of the EGF binding activity. Inclusion of EGFR residues 294–310 in the immunogen is ensures recruitment of high affinity Abs for EGFR. Inclusion of the phenylphosphonate ester structure induces clonal selection of Abs with a structurally optimized serine protease catalytic site. Therefore, catalysts superior to those generated in MRL/lpr mice will be synthesized by implementing the EGFR-CRAA strategy outlined here.

Biodistribution and Anti-Tumor Effects in Vivo

To assess biodistribution and growth effects in vivo, athymic mice bearing human tumors have been used as a model to study the tumor localization and anti-tumor effects of various drugs, toxins and Abs.

The biodistribution of the six most promising catalytic Fv constructs, along with a noncatalytic Fv construct in tumor bearing mice will be compared. The ability of the $^{125}$I-radiolabeled Fv constructs to bind and cleave the target antigen will be established in preliminary studies. The tissue-to-blood and tumor-to-blood ratios of the Fv constructs will be calculated. Imaging studies will be carried out further evaluate the tumor specificity of the Fv preparations. The presence of the catalytic function in the Fv constructs might lead to their increased dissociation from the surface of tumor cells, because the product fragments of the target antigen will likely bind the catalyst weakly compared to the intact antigen. This might result in lower tumor:blood ratios for the catalysts compared to the noncatalytic Fv. On the other hand, if the rate of internalization of the Fv into tumor cells is very rapid, the catalytic function may not influence the biodistribution pattern of the Fv. Autoradiography of tumor sections will be performed to determine the extent to which the Fv constructs are internalized by the tumor cells.

Target antigen cleaving catalysts with favorable biodistribution profiles, along with a non-catalytic Fv and an irrelevant FV, will be evaluated for their ability to inhibit the growth of tumor cells in athymic mice. The time to tumor formation (latent period), the number of mice developing tumors, and the size of tumors will be noted. Tumor growth is determined by the relative rates of cell proliferation and cell death. Apoptosis and necrosis are the distinct processes in cell death. EGFR is thought to be an important regulator of apoptotic cell death. It is possible that treatment with the catalytic Fv constructs may result in complete regression of the tumor, because the cells might be freed from negative regulation of apoptosis by EGFR. Cryostat sections of the tumors recovered from the animals will be examined by immunohistochemical methods for markers of proliferation and apoptosis, i.e., ki-67, bcl2 and bax. ki-67 is a proliferation associated antigen present throughout the cell cycle and is a reliable marker for evaluating the growing fraction of a tumor cell population. The bcl-2 and bax markers will help assess whether the cells are destined to undergo death via apoptosis.

In summary, the catalytic antibodes of the present invention represent a beneficial therapeutic reagent for the treatment of neoplastic disorders.

EXAMPLE IB

Administration of Catalytic Antibodies and Antisense p53 in Combined Chemotherapy Protocol When a cell suffers damage to its genome there are mechanisms in place in the cell that will determine if the cell will attempt repair itself or if it will undergo programmed cell death. In order for proliferating cells to effectively undertake genomic repair, they must be taken out of cycle. This is achieved by means of the so-called "cell cycle checkpoints" which allow proliferating cells time to repair genomic damage rather than passing it on to daughter cells.

Figure 18:
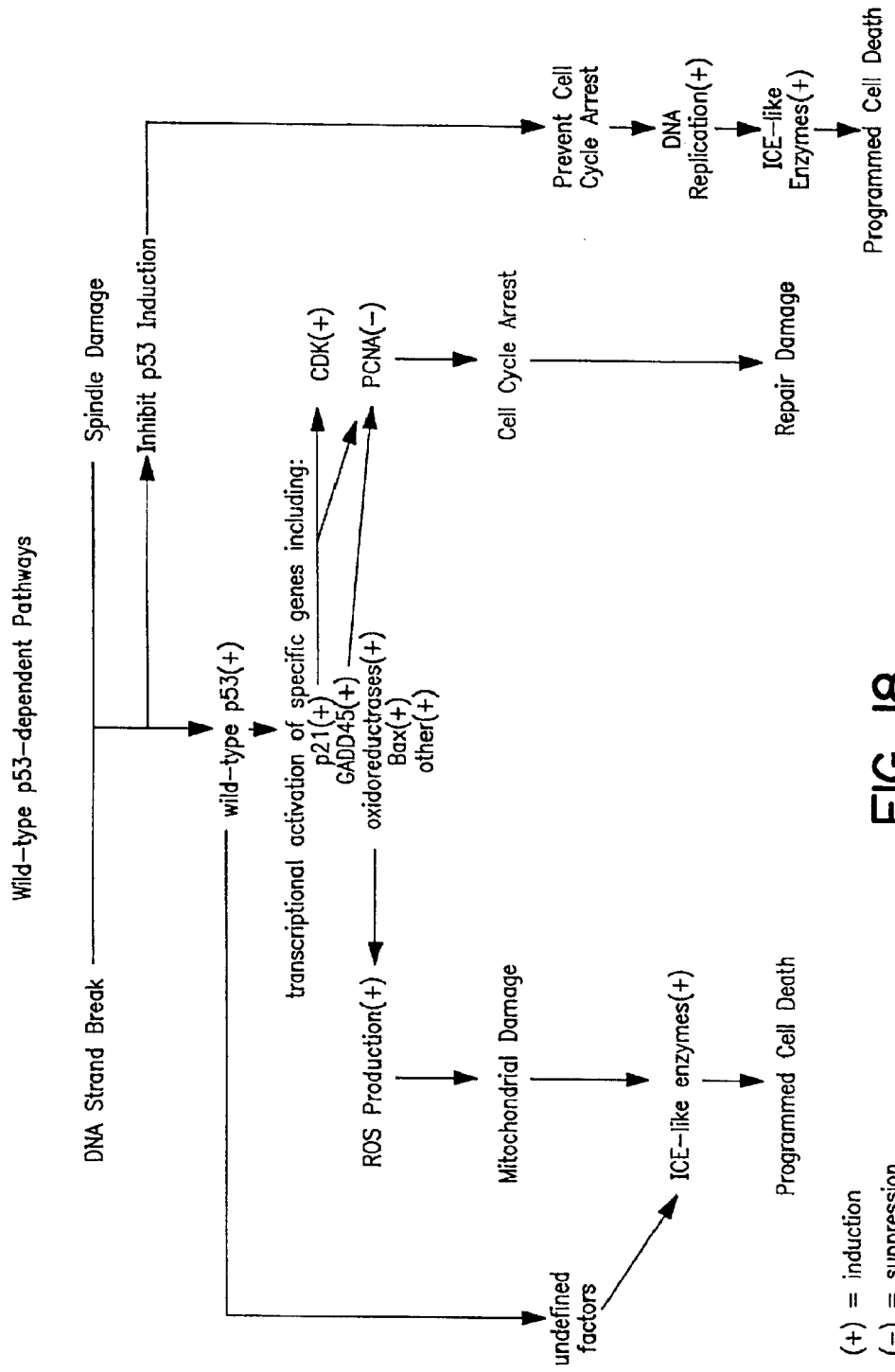
FIG. 18 is a schematic diagram of the cellular molecules which participate in p53 mediated signalling events.

FIG. 18 illustrates the central role of normal (wild-type) p53 in inducing one or the other of these two possible responses of cells to genomic damage. Damage to the genome leads to an increased expression of p53 which, in turn, sets in motion a variety of other events that produce the specific cellular response to this damage.

Based on these relationships, certain agents that inhibit p53 function, such as p53 oligos or p53 catalytic antibodies prepared according to the present invention and used incombination with a methods that provide for getting antibodies or antibody fragments accross the cell membrane, can reasonably be expected to both block programmed cell death and prevent the activation of cell cycle checkpoints depending on which event would naturally occur. Attempts to block either of these cellular responses by using inhibitors that act upstream or downstream of p53 are problematic because of the multiplicity of factors involved, FIG. 18.

These important realizations form the scientific basis for proposed therapeutic uses of p53 oligos and catalytic antibodies to treat cancer, ischemia-reperfusion injury, and septic shock/SIRS.

Description of the Cellular Mechanisms

During cell division three fundamental processes must be coordinated and any associated errors repaired: (1) the centrosomes must be duplicated and then segregated; (2) the mitotic spindle must be formed, attached to the chromosomes, and primed for elongation and sister chromatid separation at anaphase; and (3) the DNA must be replicated and the chromosomes condensed and then segregated by the mitotic spindle to opposing sides of the cell which shortly will become daughter cells.

A surveillance system is in place that interrupts cell division by means of checkpoints when it detects damage or potential damage to the genome, including any damage incurred during the natural processes just described. Hartwell and Weinhert operationally defined a cell cycle checkpoint as follows: When the occurrence of cell cycle event B is dependent upon the completion of a prior cell cycle event A, that dependence is due to a checkpoint if a loss-of-function mutation can be found that relieves the dependence.

This operational definition has been rigorously demonstrated in studies of yeast cells where three checkpoints have been described: the DNA damage, spindle and spindle pole body (centrosome equivalent) checkpoints. The DNA damage checkpoint acts at three different positions in the cell cycle to arrest proliferation when damage is detected: the G1/S and G2/M transitions, and another that monitors progression through S. Genetic studies have identified many of the checkpoint components in yeasts but the proteins involved have proven to be functionally pleiotropic, making it difficult to establish simple cause-and-effect relationships. As pointed out by Paulovich et al. (1997), for example, genes required for the DNA damage checkpoint are also involved in DNA repair, programmed cell death and transcriptional regulation. Results of yeast studies were subsequently extrapolated to mammalian cells where homologous components were found (Hartwell et al. 1994).

Many of the genes necessary for cell cycle arrest at one checkpoint are also necessary in one or both of the other two. p53, for example, has been shown to play a key role in all three (Cross et al. 1995; Fukasawa et al. 1996; Levine 1997). The critical role of p53 in instigating cell cycle arrest at the G1/S transition in response to DNA damage was first demonstrated by Kastan and his colleagues (1991) and has since been extensively researched. Kastan's group examined the human ML-1 myeloblastic leukemia cell line that appears to express wild-type p53 (exons 5 through 9 were sequenced and shown to be normal). As is true for normal cells, treatment of these leukemic cells with nonlethal doses of γ-irradiation or actinomycin D caused both G1/S and G2/M arrest. In ML-1 cells, G1/S arrest was associated with a transient 3- to 5-fold increase in p53 levels that proceeded cell cycle arrest. Caffeine treatment was found to block both induction of p53 expression and G1/S cell cycle arrest, suggesting that p53 might play role in G1/S arrest in response to DNA damage. In keeping with this hypothesis, cells lacking wild-type p53 did not show a G1/S arrest following γ-irradiation.

In a subsequent study, Kastan's group used solid tumor cell lines to strengthen their hypothesis (Kuerbitz et al. 1992). Introducing wild-type p53 expression under the control of an inducible promotor in a cancer cell line lacking p53 expression allowed cells to undergo a G1/S cell cycle arrest following γ-irradiation. It has additionally been shown that agents causing DNA strand breaks induce p53 and cycle arrest but that agents such as anti-metabolites, which are simply incorporated into DNA, do not (Nelson & Kastan 1994).

The work of Kastan's group and others have made it clear that a medically important group of agents can cause the production of reactive oxygen species (ROS) leading to the activation of p53-dependent processes by causing DNA strand breaks. These agents include a variety of anticancer treatments such as ionizing radiation and doxorubicin, as well as natural mediators including nitric oxide.

The effects of mitotic spindle inhibitors have been studied, including certain cancer chemotherapeutic agents, on cells taken from mice having a p53 genetic knockout. Following treatment, cells became tetraploid or octaploid as a result of undergoing multiple rounds of DNA synthesis without completing chromosome segregation. In contrast, normal mouse cells underwent a G2/M cell cycle arrest following treatment. In the absence of spindle inhibitors, 50% of the cells from p53 knockout mice, but not normal mice, became tetraploid by passage 7. Examination of the tissues of the p53 knockout mice also revealed the presence of tetraploid cells, demonstrating that the results obtained in in vitro studies with cells from these mice were not a culture artifact. These observations confirm earlier reports that show a correlation between loss or inactivation of p53 and tetraploidy or aneuploidy.

Similarly, Fuksaswa et al. (1996) demonstrated that cells from p53 knockout mice produce abnormal numbers of centrosomes. This appears to explain why cultured cells from p53 knockout mice become increasingly aneuploid in culture when, during the same time period, cells from mice with intact p53 remain diploid. Brown et al. (1994) found that p53 copurifies with centrosomes isolated from cultured cells, suggesting a possible direct role for p53 in regulating these organelles.

As shown in FIG. 18, p21 is a key mediator of p53-dependent cell cycle arrest in response to genomic damage. p21 binds to a number of cyclin and cyclin-dependent kinase (cdk) complexes as well as to the proliferating cell nuclear antigen (PCNA). Normal levels of p21 appear to be necessary for the formation of cyclin-cdk complexes which, in turn, are necessary for cell cycle progression (El-Deiry et al. 1993). Increased levels of p21 resulting from p53 activation, however, block cell cycle progression by interfering with the functions of these complexes and with PCNA. In at least some situations, another gene that is up-regulated by p53 in response to genomic damage, GADD45, also can institute cell cycle arrest at the G1/S transition point (Marhin et al. 1997).

Alternatively, genomic damage can lead to a p53-dependent induction of programmed cell death instead of cell cycle arrest and repair. Clarke et al. (1993), for example, have shown that thymocytes taken from mice constitutively homozygous for a deletion in the p53 gene are resistant to the induction of programmed cell death by γ-irradiation or etoposide, but not by glucocorticoid or calcium. Mice heterozygous for p53 deletion were also relatively resistant to agents that cause DNA strand breaks, but less so than the homozygots. In contrast, thymocytes from mice with intact p53 underwent programmed cell death in response to all of these treatments.

Cancer cells that do not express wild-type p53 are often found to undergo programmed cell death if expression of the protein is experimentally introduced. This has provided a model system for attempts to arrive at a mechanistic explanation of how p53 can induce programmed cell death. It must be kept in mind, however, that the use of cell lines that have eliminated wild-type p53 function and have subsequently had wild-type p53 constitutively expressed experimentally to create a model for analyzing endogenous wild-type p53 functions may result in misleading conclusions.

Johnson et al. (1996) first demonstrated that ROS can function as downstream mediators of p53-dependent programmed cell death. They produced high level human wild-type p53 expression in cultured human or rat smooth muscle cells (SMC) using adenoviral vectors carrying human p53 cDNA under the control of a strong promoter. p53 was expressed in both cell types at equivalent levels, but only in the human cells was programmed cell death induced. Within eight days of infection, essentially all of the human SMC over-expressing p53 were found to be dead. Kinetic studies documented increased levels of p53 and ROS in the SMC four hours following infection with the p53-carrying virus. Three unrelated antioxidants were shown to block ROS production but not p53 over-expression and to block the induction of programmed cell death. It was concluded that increased expression of p53 is sufficient to induce programmed cell death in at least some normal cell types, and that ROS are a downstream mediator of this induction.

Vogelstein's group (Polyak et al. 1997) used an adenoviral vector to cause the expression of wild-type p53 in human DLD-1 colon cancer cells that had inactive endogenous p53 genes. RNA was purified from these cells 16 hours after viral infection and 8 hours before evidence of programmed cell death. Analysis was conducted using the SAGE technique which allowed the quantitative evaluation of cellular mRNA populations. Approximately 8,000 transcripts were identified. Of these, 14 were markedly (greater than 10-fold) and 26 were significantly more abundant in the cells expressing p53. Thirteen of the 14 most highly induced genes were identified and several were found to encode proteins that affect the redox status of cells.

The group hypothesized that p53 might induce programmed cell death by stimulating the production of ROS. Using a fluorescent probe to measure intracellular ROS levels, the investigators found that ROS production was induced following infection with the p53-carrying virus, and that the levels of ROS continued to increase as programmed cell death progressed. Treatment of DLD-1 cells with the powerful oxidant menadione or hydrogen peroxide only induced the expression of one of the 14 genes, p21, demonstrating that this group of genes was not induced simply as a result of ROS expression. Neither were these genes induced as the result of treating the cells with indomethacin or ceramide, two agents that can induce programmed cell death in the absence of p53 expression.

Time course experiments suggested a sequence of events during which p53 transcriptionally activates redox-controlling genes, causing ROS production that results in oxidative damage to mitochondria and, in turn, cell death. Inhibition of each of these steps with specific pharmacologic agents demonstrated a cause-and-effect relationship between sequential events.

These findings suggest the following three-step model for p53-induced programmed cell death in DLD-1 cells: (1) p53 transcriptionally activates a specific subset of genes that include oxidoreductases; (2) the induced proteins collectively cause an increase in ROS levels; and (3) ROS damages mitochondria, causing leakage of calcium and other components. These components stimulate members of the ICE-like enzyme family that are consistently involved in the terminal events of programmed cell death.

There also appears to be some variability among different cell types in terms of the genes that are transcriptionally up-regulated by wild-type p53 in response to genomic damage. Two of these are Bax, a member of the BCL-2 family that has been shown to sometimes be involved in the p53-dependent induction of programmed cell death, and GADD45, the product of which binds to PCNA and thereby can cause a cell cycle checkpoint arrest. McCurrach et al. (1997), for example, found that in primary fibroblasts, Bax is one of the effectors of wild-type p53-dependent programmed cell death induced by chemotherapy. In this study, wild-type p53 was found to transcriptionally activate Bax. Neither Bax nor GADD45, however, were among the genes found to be induced by wild-type p53 in the previously discussed study by Polyak et al. (1997). The potential importance of Bax in the induction of programmed cell death in response to cellular damage caused by chemotherapy has been demonstrated in work by Strobel et al. (1996). This group transfected an expression vector carrying the Bax cDNA into the SW626 ovarian cancer cell line that lacks functional p53. Transfectants showed a mean 10-fold increase in Bax expression compared to control cells. The threshold for the induction of programmed cell death following chemotherapy treatment was substantially reduced in the Bax transfectants when the chemotherapeutic agent was paclitaxel, vincristine or doxorubicin, but not when the agent was carboplatin, etoposide or hydroxyurea.

Additional studies involving cancer cell lines that express wild-type p53 and undergo either proliferation arrest or programmed cell death following treatment with doxorubicin, show that most of the same 14 genes that were highly induced in DLD-1 cells following the introduction of p53, were up-regulated both at lower doses of the drug, which caused cell cycle arrest, and at higher doses, which caused programmed cell death (Polyak et al. 1997). The authors speculated that the critical factor in determining whether a cell undergoes cycle arrest or programmed cell death is the ability of that cell to cope with oxidative stress. In other words, cells with a low capacity to handle oxidative stress undergo programmed cell death while more resistant cells undergo cycle arrest.

The level of oxidative stress that cells are experiencing has been positively correlated with their tendency to undergo p53-dependent programmed cell death rather than cell cycle arrest and repair following genomic damage. Lotem et al. (1996) studied the effects of oxidative stress and cytokines on these phenomena in myeloid leukemia cells. Antioxidants and certain cytokines exhibited a cooperative protection of these cells against programmed cell death induced by cytotoxic compounds. Increasing oxidative stress with hydrogen peroxide treatment, however, augmented the occurrence of the cell death program and increased the level of protective cytokine treatment needed to prevent programmed cell death.

Salicylates are known to inhibit the activation of protein kinases and transcription factors involved in stress responses. Chernov and Stark (1997) found that salicylate reversibly inhibits wild-type p53 from binding to DNA and consequently inhibits the ability of p53 to induce p21 transcription and programmed cell death following treatment with toxorubicin or radiation. If the salicylate is washed out within 60 hours of the DNA damage, the inhibited p53-dependent events are able to go on to completion.

One factor that in some circumstances influences whether wild-type p53 induces cell cycle arrest or programmed cell death following genomic damage is c-myc. Saito and Ogawa (1995) studied the rat hepatocellular carcinoma cell line, FAA-HTC1, that constitutively expresses c-myc and does not express p53. c-myc expression in these cells was effectively suppressed by an antisense L CHK2HRoligonucleotide. Wild-type p53 expression was achieved by transfecting a dexamethasone-inducible expression vector carrying wild-type p53 cDNA into these cells. The results showed that wild-type p53 can act in the same cells as either an inducer of cell cycle arrest or as an inducer of programmed cell death depending on the status of c-myc. Wild-type p53 expression resulted in the induction of programmed cell death in a portion of the cells, but did not inhibit the proliferation of surviving cells. If c-myc expression was inhibited, wild-type p53 expression caused an inhibition of cell proliferation but did not induce programmed cell death. Unregulated expression of c-myc has also been shown by others to be capable of inducing programmed cell death (Evan et al. 1992; Hoang et al. 1994; Lotem & Sachs 1993).

Additional studies have shown that wild-type p53 may in some circumstances induce programmed cell death without first causing the expression of other genes. In these situations, wild-type p53-dependent programmed cell death occurs in the presence of actinomycin D or cycloheximide, which block RNA and protein synthesis respectively (Caelles et al. 1994). The introduction into Hela cells of a p53 expression vector that lacks the terminal p53 amino acid residues required for p53 binding to DNA, for example, has been shown to produce p53-dependent programmed cell death (Haupt et al. 1995). That this observation supports the non-involvement of p53 in transcription assumes without adequate justification, however, that the only way p53 can affect transcription is by directly binding to the regulatory elements of genes themselves. These and similar findings (Sabbatini et al. 1995) have been used to support the argument that p53 can induce programmed cell death without affecting transcription.

It is probable, therefore, that wild-type p53 may induce programmed cell death by means of transcriptionally activating specific sets of genes, by direct protein-protein interactions or by a combination of these methods. The induction of programmed cell death, however, does not necessarily require the expression of wild-type p53. This is clear from the observation that p53-knockout mice develop normally as well as the fact that cells lacking wild-type p53 can be induced to undergo programmed cell death (Clarke et al. 1993).

As shown in FIG. 18, the multiple pathways that can initiate programmed cell death converge to utilize a common terminal phase involving the interleukin 1-beta-converting enzyme (ICE-like) family. This enzyme family is currently known to contain 11 members and can be divided into three subfamilies: the ICE, CPP32, and Ich-1 subfamily called caspases (Boldin et al. 1996; Chinnaiyan et al. 1996; Duan et al. 1996a & 1996b; Fernandes-Alnemri et al. 1996; Lin & Benchimol 1995; Lippke et al. 1996; Muzio et al. 1996; Wang et al. 1996). Sabbatini et al. (1997), for example, specifically studied the role of ICE family enzymes in the occurrence of p53-dependent programmed cell death. They demonstrated that a peptide inhibitor of the ICE-like protease CPP32 inhibited the cell death program in baby rat kidney cell lines induced by experimentally expressing wild-type p53 in these cells.

It also appears that wild-type p53 can potentiate the ability of ICE family enzymes to cause programmed cell death (Jung & Yuan 1997). For example, inactivating wild-type p53 function in COS-1 cells keeps them from undergoing programmed cell death when they are transfected with an expression vector carrying the cDNA for an ICE-like enzyme, while transfecting normal COS-1 cells causes them to undergo the death program. Expression vectors carrying either an ICE-like enzyme or a temperature-sensitive p53 mutant were both transfected into COS-1 cells with inactive endogenous wild-type p53. At the temperature permissive for wild-type p53 function, the ability of the ICE-like enzyme to cause programmed cell death was significantly augmented. Additional experimentation showed that the ability of wild-type p53 to potentiate the induction of programmed cell death by the enzyme was mediated by Bax.

OL(1)p53 for the Treatment of Cancer

All cancer treatments in clinical use kill cancer cells by inducing programmed cell death in a dose-dependent manner. In some instances induction of this program has been shown to be wild-type p53-dependent. At lower doses, many agents that cause genomic damage effect the induction of a checkpoint in cells with wild-type p53. The checkpoint temporarily arrests cell proliferation, providing time for the damaged cells to repair.

Recent studies by investigators who have not been involved in the development of OL(1)p53 provide a rationale for why inhibiting wild-type p53 expression can enhance the killing effect of many anticancer treatments on comparable cancer cells with an intact wild-type p53-dependent cell cycle checkpoint. Evidence shows that when the cell cycle checkpoint fails to engage following therapeutic damage to the genome, cancer cells continue to replicate their DNA in the absence of mitosis leading to the induction of programmed cell death. The therapeutically important result is that, in the context of a blocked checkpoint, anticancer treatments become much more effective in killing cancer cells.

In some studies, engagement of the checkpoint was prevented by genetically knocking out the expression of wild-type p53 or one of its downstream effectors, particularly p21. Given the irreversible nature of these interruptions, it is clear that wild-type p53 is not required for the induction of programmed cell death under these circumstances. In other experiments, methylxanthine derivatives such as pentoxifylline or the protein kinase C inhibitor UCN-01 (7-hydroxystaurosporine), both of which inhibit G2 checkpoint function, were shown to synergize with agents that interrupt the wild-type p53 pathway in further boosting the sensitivity of cancer cells to anticancer agents.

Consistent with this role of wild-type p53, p53 oligos and OL(1)p53 in particular can synergistically boost the ability of genome-damaging agents to kill cancer cells. Further, at doses optimum for causing a maximal lethal effect on cancer cells, the combination of OL(1)p53 and an anticancer agent did not kill tested normal cell types.

When phosphorothioate oligos such as OL(1)p53 or natural phosphodiester oligos bind to cells, they induce the cells to increase their production of free oxygen radicals by a cyclo-oxygenase-dependent mechanism. The effect is much more pronounced in ordinary cell cultures carried out in 20% (atmospheric) oxygen than at reduced oxygen tensions. These free radicals can cause genomic damage, and this phenomenon may explain why OL(1)p53 kills cancer cells in ordinary tissue culture without the necessity of adding a compound capable of causing genomic damage, such as a cancer chemotherapeutic agent, and why OL(1)p53 does not kill cancer cells cultured under oxygen levels similar to those found in the body unless a genomic damaging agent is added. Cancer cells pretreated with oligos such as OL(1)p53 can be killed with doses of genome-damaging agents which are not cytotoxic to the cells in the absence of the p53 oligo. Presumably this synergy can be even further enhanced by G2 inhibitors, such as pentoxifylline or UCN-01, that are more effective when used to treat cancer cells with compromised wild-type p53 function than those with intact p53 function.

Since phosphorothioates are DNA analogs, it is possible that cancer chemotherapeutic agents with an affinity for DNA would bind to them. This notion was tested using OL(1)p53, which was shown to tightly bind mitoxantrone but not idarubicin or daunorubicin. The interaction between mitoxantrone and the oligo substantially reduced the toxic effects of the chemotherapeutic agent on cancer cells that did not express wild-type p53.

In another study of oligo-drug interactions, bioactive metabolites of acetaminophen known to react with sulfur groups were shown to bind to phosphorothioate oligos including OL(1)p53. This interaction may inactivate OL(1) p53 and should be determined prior to further clinical testing.

Pharmacology and toxicology studies carried out in several species, including Rhesus monkeys, demonstrate that OL(1)p53 has pharmacokinetic properties favorable for its use as a systemic therapeutic agent and that the oligo is non-toxic even at dose levels well above the expected therapeutic level. Sequencing and cell culture studies suggest that OL(1)p53 suppresses p53 expression in monkey cells as it does in human cells. The oligo, however, does not have any specific effects on cells or tissues from lower animals.

A Phase I clinical trial of OL(1)p53 as a single agent was carried out in patients with acute myelogenous leukemia or the myelodysplastic syndrome. The oligo was given by continuous infusion over 10 days, and results showed the oligo to be nontoxic over a dose range predicted to yield therapeutic levels. No complete responses were seen.

Malignant cells taken from the patients just prior to the start of OL(1)p53 administration and at various times during the infusion were put in culture under 20% oxygen. Compared to peripheral leukemic blast cells from the untreated patients, those taken after the start of OL(1)p53 infusion died more rapidly as a function of the amount of OL(1)p53 infused into the patient. Similarly, long-term bone marrow cultures set up from leukemia or myelodysplasia patients demonstrated a substantially reduced capacity to generate malignant cells as a function of the amount of OL(1)p53 infused into the donor. This suppression lasted for many months following treatment without any evidence that the effect was reversible.

The OL(1)p53 clinical trial results are consistent with laboratory data that strongly suggest that the oligo must be used in conjunction with genomic damaging anticancer agents in order to be active in patients. Interpretation of cell culture data using cells from patients in the trial is also consistent with this hypothesis. When cancer cells were placed in culture under 20% oxygen, the oligo induced these cells to produce ROS which served as the genomic damaging agent.

It follows from the above discussion that blocking p53 expression, with a p53 oligo for example, can result in the prevention of (1) cell cycle arrest, allowing time for an attempt at repair, and (2) p53-dependent programmed cell death. Since many cancer therapies cause genomic damage, they can also be expected to cause the induction of wild-type p53 in those cancer cells that express it. Indeed, x-irradiation, topoisomerase inhibitors, alkylating agents, anthracyclines, spindle poisons and certain antimetabolites are all known to produce p53-dependent cell cycle arrest (Cross et al. 1995; Kastan et al. 1991; Linke et al. 1996; Tishler et al. 1995). Inhibition of such induction of wild-type p53 should increase the toxicity of these anticancer therapies to proliferating cancer cells by allowing the damaged genome to be replicated, resulting in the production of dysfunctional cells and inducing programmed cell death as well.

A series of publications that address this issue have come from the laboratories of collaborating investigators at Johns Hopkins and the University of Pennsylvania (McDonald et al. 1996; Waldman et al. 1996 & 1997). Isogenic human colon cancer cell lines were used in these studies, differing only in their p21 status. The p21-/- cells were produced from the p21+/+ cells using homologous recombination. Normally, the induction of p53 by genomic damage leads to induction of p21 by the p53 acting as a transcription factor in directly binding to the p21 gene. Newly synthesized p21 then binds to and blocks the function of proteins required for cell cycle progression, FIG. 18.

The first of these studies (McDonald et al. 1996) sought to determine if p21-/- HCT116 human colon cancer cells had DNA repair defects when compared to p21+/+ HCT116 cells (both HCT116 clones have wild-type p53). The p21-deficient clone was found to be two to three times more sensitive to UV damage than the p21-expressing cells when judged by clonogenic survival assays. Further, p21-/- cancer cells had a two- to three-fold increased frequency of spontaneously arising 6-TG-resistant colonies indicative of hprt gene inactivation by mutation compared to cells with intact p21 function. These data suggest that the loss of p21 function is associated with reduction in the ability of cells to repair DNA damage.

To further test this concept, investigators transfected an expression vector into p21+/+ or -/- HCT116 human colon cancer cells. The vector consisted of a beta-galactosidase cDNA driven by a cytomegalovirus reporter, and was purposely damaged prior to transfection using either UV irradiation or a cis-platinum anticancer agent. HCT116 cells lacking p21 were found to be three- to five-fold less efficient at repairing the damaged expression vector compared to p21+/+ HCT116 cells. Transfection of an expression vector carrying p21 cDNA into the p21-/- HCT116 cells increased their repair capacity two- to three-fold. It was concluded that agents which inhibit p21 interaction with PCNA, and thus prevent cell cycle arrest in response to DNA damage, may have synergistic cytotoxic interactions with classical anticancer agents that cause DNA damage.

In a subsequent study, investigators examined the effects of certain genomic damaging agents on p21+/+ and -/- HCT116 cells (Waldman et al. 1996). Agents included the cancer therapeutics doxorubicin, etoposide and γ-irradiation as well as the topoisomerase-1 inhibitor camptothecan. Each was shown to be capable of completely killing cultures of the p21-/- cells within 90 hours of treatment by inducing programmed cell death at concentrations causing p21+/+ cells to undergo a prolonged cell cycle arrest but not cell death. Analysis of the p21-/- cells showed that, following treatment, the cells were briefly blocked in G2 but not G1 and then began multiple rounds of DNA synthesis in the absence of mitosis, and that the resulting hyperdiploid cells with abnormal nuclear morphology subsequently underwent programmed cell death.

A similar set of experiments was conducted using the DLD-1 human colon cancer cell line which, unlike the HCT116 line, has mutated p53 but resembles the HCT116 line in being diploid. The authors reasoned that p53 mutant cells would not express p21 following DNA damage and would be functionally equivalent to p21-/- cells. As predicted, DLD-1 cells expressed little p21 after treatment with doxorubicin or γ-irradiation, and demonstrated a checkpoint defect that resulted in the occurrence of essentially the same set of morphologic/physiologic changes as in the HCT116 line that terminate in programmed cell death.

When these experiments were conducted using aneuploid human colon cancer cell lines with mutant p53, the effects of treating two of these lines with DNA-damaging agents were found to follow the same pattern of events that lead to programmed cell death. In the third line, pre-existing aneuploidy was sufficiently pronounced to inhibit any firm conclusions about a significant increase in DNA content prior to cell death. Waldman et al. concluded that "detailed analyses demonstrated that the programmed cell death was apparently induced by an uncoupling between mitosis and S phase after DNA damage. Instead of undergoing coherent arrest, cells without the p21-dependent checkpoint continued to undergo rounds of DNA synthesis in the absence of mitosis, culminating in polyploidy and programmed cell death" (p. 1034).

However, the authors failed to comment on an important point demonstrated by their experiments. Several publications have indicated that in cells with wild-type p53, programmed cell death induced by many anticancer therapeutics is p53-dependent (Dronehower et al. 1992; Lowe et al. 1993; Symonds et al. 1994). Further, some cancer cells with wild-type p53 can be more sensitive to chemotherapy than similar cells with mutated p53 (Aas et al. 1996; Lowe et al. 1993a & 1993b). Yet the finding that three different colon cancer cell lines with mutated p53 underwent a similar series of events leading to the induction of programmed cell death, as in the HCT116 p21-/- cells, suggests that programmed cell death as a result of replicating damaged DNA in the absence of mitosis is wild-type p53-independent.

The HCT116 studies demonstrate that interruption of p53/p21-dependent cell cycle arrest can lead to a lowering of the threshold for programmed cell death induction by anticancer treatments because programmed cell death is induced in p21-/- cells at lower doses than is required for HCR116 cells that are p21+/+. Since both the p21+/+ and p21-/- HCT116 cells express wild-type p53, this induction could be p53-dependent. If based on a p53-dependent programmed cell death mechanism, the threshold level at which DNA or genomic damage induces programmed cell death might be lower in cancer cells that express wild-type p53. In the absence of wild-type p53, however, there could be a higher damage level threshold for the induction of p53-independent programmed cell death.

Because OL(1)p53 transiently inhibits the expression of p53, treating cancer cells with this oligo plus conventional therapy can cause both an interruption of cell cycle checkpoints during the time p53 is suppressed, and p53-dependent programmed cell death following the recovery of p53 expression. OL(1)p53, therefore, should be more effective at sensitizing cancer cells expressing wild-type p53 to anticancer therapies than the approaches just described involving p53 or p21 genetic knockouts.

Experiments presented in the third monograph of this series were designed to determine if inhibition of cell cycle checkpoints would increase γ-irradiation sensitivity of HCT116 human colon cancer cells grown in immunocompromised animals (Waldman et al. 1997). Xenograft tumors were established from p21+/+ and p21−/− subclones of the cell line. In the absence of treatment, p21+/+ and p21−/− tumors grew at almost identical rates. Twelve to 17 animals per group with tumors of approximately 50 mm$^2$ were then treated with either 7.5 or 15 Gy of local γ-irradiation and subsequently measured biweekly. Radiation of animals with the p21+/+ tumors resulted in no cures, and all of the p21+/+ tumors continued to grow for several days following treatment. In contrast, 18% and 38% of the p21−/− tumors (P<0.01 by chi-square test) were cured by the γ-irradiation as a function of dose where a cure was defined as the absence of detectable tumor. p21−/− tumors that were not cured showed substantial dose-dependent decreases in size following treatment.

A second objective of this study was to determine the value of clonogenic survival assays in evaluating cancer therapies influenced by the p53 and/or p21 status of target cells. It was found that the number of clones surviving γ-irradiation were few in number, but nearly equivalent when the p21+/+ and p21−/− subclones of HCT116 were compared. The low colony number was attributed to cell cycle arrest and programmed cell death respectively. In the case of p21+/+ cells, but not p21−/−, the area between surviving colonies consisted of a lawn of viable cells. Investigators pointed out that this lawn of viable p21+/+ cells functioned like a feeder cell layer such as is known to be important in supporting the growth of clonogenic cells. They further argued that the existence of this feeder layer in the treated p21+/+ tumors and the lack of such a feeder cell population in vivo could explain their animal data.

Another group also examined the effects of wild-type p53 and/or p21 disruption on the sensitivity of cancer cells to certain cancer chemotherapeutic agents and ionizing radiation (Fan et al. 1995 & 1997). MCF-7 human breast cancer cells or HCT116 colon cancer cells, both of which had wild-type p53, were either transfected with a human papilloma virus type-16 E6 gene (MCF-7/E6 or HCT116/E6) or a dominant p53 mutant (MCF-7/mu-p53) to interrupt the wild-type p53 function. Using a clonogenic survival assay, all three subclones with inhibited wild-type p53 function, as well as the HCT116 p21−/− cells, were shown to be significantly more sensitive to cisplatin and nitrogen mustard than the corresponding cells with intact wild-type p53 or p21 function.

All four of the subclones with disrupted wild-type p53 or p21 function were found to be deficient in their ability to repair transfected cisplatin-damaged CAT-reporter genes when compared to the corresponding cells with intact wild-type p53 or p21 function. Consequently, the investigators attributed the increased cisplatin sensitivity of these cells to defects in G1 checkpoint control, nucleotide excision repair, or both.

Like the Johns Hopkins group, Fan's group did not see a significant difference in the clonogenic survival assay between cells with intact wild-type p53 or p21 function and those without it when ionizing radiation was used as the genomic damaging agent. They apparently were not aware, however, of the shortcomings of this assay as illuminated by the Johns Hopkins research team.

A survey of the p53 status and radiosensitivity of twenty human squamous-cell carcinoma cell lines taken from patients with head and neck cancers was conducted by Servomaa et al. (1996). p53 mutations and/or deletions were found in 15 of the lines. The "mean inactivation dose" (AUC) was determined using a clonogenic survival assay scored four weeks after radiation treatment. The results were 1.82±0.24 Gy for the lines with mutated or absent p53 and 2.23±0.15 Gy for the lines with wild-type p53 (P<0.01). The authors concluded that the lines with no p53 expression were the most radiosensitive.

The methylxanthine derivative pentoxifylline has been found to be a G2 checkpoint inhibitor (Russell et al. 1996). It is a relatively nontoxic compound given to patients with a variety of disorders because of some of its other properties, which include the ability to increase red blood cell flexibility (Ciocon et al. 1997). Pentoxifylline exhibited synergism with cisplatin in killing cancer cell lines with interrupted wild-type p53 function or p21 deficiency without altering the sensitivity of control cells with intact wild-type p53 and p21 (Pan et al. 1995). The drug was also found to be much more effective at inhibiting the G2 checkpoint in cells that had compromised wild-type p53 function.

Russell et al. (1996) inactivated p53 function in the human A549 lung adenocarcinoma cell line by transducing the E6 gene from HPV type 16. Using a clonogenic survival assay, they found that both pentoxifylline and a novel methylxanthine, lisofylline, caused a 15-fold sensitization of the E6 transduced cancer cells to γ-irradiation when compared to controls. Both agents were shown to block the ability of radiation to induce G2 cell cycle arrest, and lisofylline was found to block G1 arrest as well.

UCN-01 (7-hydroxystaurosporine) is a protein kinase C inhibitor that can also block the G2 checkpoint. It has shown anti-neoplastic activity against human tumors grown in rodents and is currently in clinical trail for cancer treatment (Pollack et al. 1996). Wang et al. (1996) tested the ability of this agent to influence the. sensitivity to cisplatin of MCF-7 breast cancer cells with wild-type p53 or p53 inactivated by transfection of an expression vector carrying the HPV E6 gene. Drug sensitivity was measured using both clonogenic survival and MTT assays and was shown to be markedly enhanced by UCN-01 treatment in cells lacking intact wild-type p53 function when compared to cells with functional wild-type p53. As for the studies involving pentoxifylline, UCN-01 was found to be much more effective in blocking G2 arrest induced by genomic damage in cells where wild-type p53 function had been eliminated than in those with intact function.

Similarly, Shao et al. (1997) demonstrated that UCN-01 is much more effective in boosting the cytotoxic effects of genomic damaging agents on HCT116 colon and MCF-7 breast cancer cell lines lacking wild-type p53 function as a result of experimental manipulation compared to the same cells where this function is intact.

Caffeine also blocks G2 cell cycle arrest in vitro, and appears to operate by activating p34cdc2 kinase. Yao (1996a) demonstrated that caffeine treatment selectively sensitizes tumor cells deficient in wild-type p53 function to radiation-induced programmed cell death. Thus it appears that for some cancers, the use of OL(1)p53 plus a G2 checkpoint inhibitor might boost the beneficial effects of conventional anticancer therapy to a greater degree than OL(1)p53 alone.

Microtubule active agents induce a cell cycle checkpoint that typically causes a G2 arrest. Several studies have implicated wild-type p53 as playing a role in influencing the response of cells to G2 active agents (Fan et al. 1995; Powell et al. 1995; Russell et al. 1995). These findings led Tishler et al. (1995) to examine the ability of the cancer chemotherapeutic agents taxol, vinblastine and nocodazole to induce wild-type p53-dependent processes in the premalignant embryonic mouse NIH-3T3 cell line. All three microtubule active agents caused G2 cell cycle arrest and increased p53-DNA binding. Only vinblastine and nocodazole were shown to cause an increase in p21 transcription.

Wahl et al. (1996) extended these studies by looking at the effects of interrupting wild-type p53 function on the sensitivity of fibroblasts to taxol. Wild-type p53 function was disrupted in normal human fibroblasts by transfecting them with expression vectors carrying either the HPV E6 gene or the SV40 T antigen gene. Fibroblasts also were taken from normal and p53 knockout mice. Compromised p53 function in cells from either type correlated with a seven- to nine-fold increase in taxol cytotoxicity compared to controls. Taxol was shown to kill cells by inducing programmed cell death independently of their p53 status. Cells with intact p53 that survived taxol treatment showed increased levels of p21 and underwent cell cycle arrest.

In response to genomic damage, wild-type p53 induces, in addition to p21, a second gene GADD45 that also functions to induce a cell cycle checkpoint by means of its inhibiting effect on PCNA. Smith et al. (1996) blocked GADD45 expression in the RKO human colon cancer cell line that expresses wild-type p53 by transfecting it with an antisense vector. Reducing GADD45 levels sensitized the cancer cells to the killing effects of UV irradiation and to cisplatin treatment. In addition, cells in which GADD45 was suppressed showed a reduced capacity to repair DNA damage as judged by the use of UV-damaged reporter plasmids and unscheduled DNA synthesis experiments. Expression vectors carrying a variety of genes that disrupt wild-type p53 function were also transfected into the RKO cells. Suppressing p53 function had the same effect on DNA repair as suppressing GADD45 expression.

The existence of at least one additional p53-regulated gene, GADD45, that can produce generally the same inductive effects as p21 cell cycle checkpoints makes p53 a better target than p21 for blocking checkpoint induction by genomic damaging agents.

According to the present invention, inhibitors of EGFR or HER2 such as conventional monoclonal antibodies or preferably catalytic antibodies generated according to the present invention used in combination with p53 oligos such as OL(1)p53 and/or other cell cycle checkpoint inhibitors such as UCN-01, p21 oligos or p27 oligos will be particularly well suited for use incombination with conventional chemotherapy for the treatment of carcinomas that express EGFR and/or HER2.

Mendelsohn and his coworkers have shown that blocking EGFR function, for example with a monoclonal antibody, causes an increased expression of p53 and p21 or p27/KIP1 resulting in the induction of a cell cycle checkpoint (Wu et al. 1996; Peng et al., 1996). The combined use of a EGFR inhibitor with a p53, p21, or p27 inhibitor such as an oligonucleotide or catalytic antibody will prevent the cell cycle arrest and boost the anticancer effect of the EGFR inhibitor particularly when used in combination with conventional cancer therapy capable of causing genomic damage.

In addition the use of a p53 oligo, such as OL(1)p53, will assist the inhibitory effect of other EGFR inhibitors because p53 transcriptionally acitvates the EGFR gene (Ludes-Meyers et al., 1996; Sheikh et al., 1997).

(C) Combined Treatment of Patients with EGFR Catalytic Antibodies and OL(1)p53

Treatment schedule would include the following aspects: (1) A sample of the cancer will be taken to determine the mutational status of the p53 gene. (2) Patients will be infused with 0.1 mg/kg/hr of the oligo for approximately five days and will receive a bolus injection of the EGFR catalytic antibody iv at a dose in the 1–50 mg range dependig to the turnover rate of the antibody. (3) Conventional chemotherapy will be started 24 hours after beginning the oligo infusion. The chemotherapeutic agent(s) selected will be ones that do not bind to OL(1)p53 and which are capable of causing genomic damage. Suitable oligos for this use are described in U.S. Pat. No. 5,654,415, the disclosure of which is incorporated by reference herein.

EXAMPLE II

Catalytic Antibodies in Vaccination against HIV

A vaccine construct useful in the treatment of AIDS composed of a model B cell epitope and a T helper epitope derived from gp120 is described herein. CRAAs of the B cell epitope will be designed to elicit catalytic Abs. An exemplary B cell epitope is derived from the CD4 binding site, which is generally conserved in different HIV-1 strains. The CD4 binding site of gp120 is a suitable target, further, because unlike many other epitopes, it is accessible to Abs on the native viral surface [31]. It is known that the CD4 binding site is a conformational determinant.

In the present invention, preparation of a catalytic Ab that recognizes a specific portion of the CD4 binding site (as opposed to the entire CD4 binding site) is described. Additional peptide epitopes in gp120 (or other HIV proteins) that might be suitable targets for catalytic Abs will also be identified. Because cleavage of gp120 may lead to global changes in the protein conformation, accompanied by loss of biological activity, certain gp120 peptide epitopes may be appropriate targets of catalytic Abs even if they do not participate directly in HIV-1 binding to host cells or HIV-1 interactions with intracellular components. These and other targets are also contemplated to be within the scope of the present invention.

T cell help for Ab synthesis is potentially subject to restriction in different individuals due to MHC polymorphism. In the present invention, mouse strains with well-defined genetic backgrounds will be used as models for the elicitation of catalytic immunity in response to B-T epitope conjugates. A "universal" T-helper epitope recognized promiscuously by various MHC class II alleles will be utilized. Another benefit of this approach is that it is readily adaptable to human clinical trials.

Figure 7:
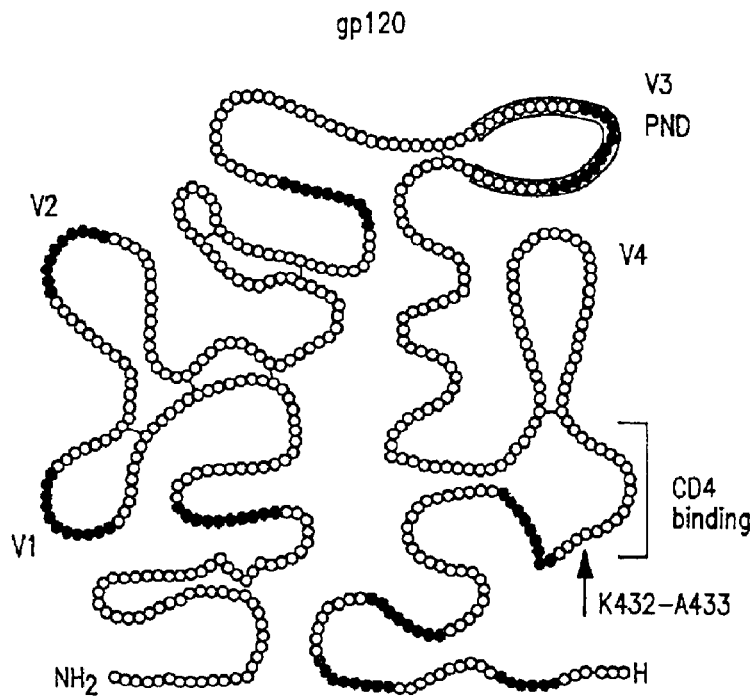
FIG. 7 shows a schematic representation of the structure of gp120. V, variable regions; PND, principal neutralizing determinant; arrow, cleavage site targeted by catalytic antibodies generated using the methods of the present invention.

The envelope glycoproteins of HIV-1 are synthesized as a single 160 kD precursor, gp160. This protein is cleaved at the Arg511-Ala512 bond by a cellular protease, producing gp120 and the integral membrane protein gp41. The biological activity of gp120 is a key ingredient in initial binding of host cells by HIV-1, propagation of the virus, and its toxic effects on uninfected neurons and other cells. Binding of a conformational epitope of gp120 to CD4 receptors on host cells is the first step in HIV-1 infection. Individual amino acids constituting this epitope appear to be located in the second (C2), third (C3), and fourth (C4) conserved gp120 segments [12]. These are gp120 residues 256, 257, 368–370, 421–427 and 457. See FIG. 7. Monoclonal antibodies that bind the CD4 binding site have been described [32]. Since the CD4 binding site is a conformational epitope, distant residues that are not themselves constituents of the epitope may be important in maintaining the ability to bind CD4.

gp120 interactions with other host cell proteins are also essential for virus propagation. For example, binding of gp120 by calmodulin may be involved in HIV-1 infectivity, as revealed by the inhibitory effect of calmodulin antagonists. Asp180 located between the V1 and V2 regions of gp120 is critical for viral replication [33]. Similarly, the V3 loop may be essential for infectivity [34]. It is clear, therefore, that structural determinants in gp120 other than those constituting the CD4 binding site are necessary for virus genome replication, coat protein synthesis, and virus particle packaging.

Trypsinization of gp120 blocks its neurotoxic effects. Treatment of HIV-1 particles with trypsin, mast cell tryptase or Factor Xa attenuates their infectivity. Cleavage of gp120 at residues 269–270 or 432–433 destroys CD4 binding capability, whereas cleavage at residues 64–65, 144–145, 166–167, 172–173 or 315–316 does not affect CD4 binding [35]. On the other hand, cleavage at the Arg315-Ala316 peptide bond located in the V3 loop of gp120 by a cellular protease is believed to be essential for productive viral infection. A dipeptidylpeptidase expressed on the host cell-surface (CD26) has been proposed as being responsible for cleavage at Arg315-Ala316. This cleavage site is located in the principal neutralizing determinant (PND), which is a component of the V3 gp120 loop to which protective Abs are readily synthesized. It has been hypothesized that Ab binding to the PND blocks the cleavage of gp120 by a host cell protease, resulting in HIV neutralization. There is no evidence that the PND plays a direct role in HIV binding by CD4, but its participation in binding by the HIV coreceptors has been suggested.

Efficient Ab synthesis by B cells is dependent in part on recruitment of T helper cells, which, once sensitized, secrete the necessary stimulatory cytokines and activate B cells by direct contact mediated through accessory molecules, such as CD4 on T helper cells and B7 on B cells. Recruitment of Ag-specific T cells occurs through recognition by the T cell receptor (TCR) of the complex of a processed Ag epitope bound to MHC class II molecules.

The peptide-based vaccines are formulated by covalently linking a T cell epitope to a B cell epitope, against which the host synthesizes Abs. The T epitope binds MHC class II molecules on the surface of antigen-presenting cells, and the MHC class II complex of the B-T epitopes is then bound by the TCR. Different individuals in an outbred species express different MHC class II alleles involved in Ag presentation to T cells (I-E and I-K loci). Ideally, a peptide vaccine should be free of MHC restrictions, i.e., a robust Ab response should be provoked regardless of the MHC class II variations involved in Ag presentation.

The interactions between MHC class II molecules, the TCR and the Ag epitope are quite promiscuous. Thus, certain peptides can serve as universal T epitopes, i.e., these peptides can bind the different MHC class II alleles efficiently. Further, there is no apparent restriction of recognition of the peptides at the level of the different types of TCRs. Such peptides are suitable T epitope components in vaccines designed to neutralize HIV through elicitation of a protective Ab response, as described in the present invention.

As mentioned previously, certain Abs both bind and cleave peptide bonds in protein antigens. Recent studies suggest that certain germline genes encoding the V domain of L chains are capable of expressing this catalytic activity. Abs and L chains with comparatively nonspecific peptidase activity (designated polyreactive activity) have been described in unimmunized humans and animals [36]. Further, the catalytic residues of a VIPase L chain identified by mutagenesis are encoded by a germline VL gene. The peptidase activity may also be improved over the course of somatic diversification of Abs which occurs following immunization with peptide antigens. Certain VIPase L chains with high levels of catalytic efficiency have been observed to be highly mutated in comparison to their germline gene counterparts [14]. Pairing of the appropriate VH domain with a catalytic VL domain is described to result in improved catalytic efficiency [28]. Further, polyclonal catalytic Abs isolated from patients with autoimmune disease display high affinities for their autoantigens [1,4,5], which is a classical sign that the Abs have beeen subjected to somatic mutations and clonal selection.

The presence of catalytic Abs in autoimmune disease may be due to a genetic predisposition towards catalyst synthesis, brought about by selective expression of particular germline V genes or by increased formation of catalytic sites during somatic sequence diversification of Ab V domains. The observation that autoimmune disease is associated with biased usage of different V-genes is well-established in the literature. Other genes relevant to Ab expression may also contribute to catalytic activity levels in autoimmune disease. The MRL/lpr mouse is known to be a good catalytic Ab producer [7]. In this mouse strain, a mutation of the Fas apoptosis gene is believed to permit proliferation of T and B cells and expression of lupus-like disease.

By incorporating appropriate structure in the immunogens capable of inducing the synthesis of Abs that combine specificity for gp120 with rapid peptide bond cleaving activity, an immunotherapeutic agent for the treatment of AIDS will be generated.

Figure 8:
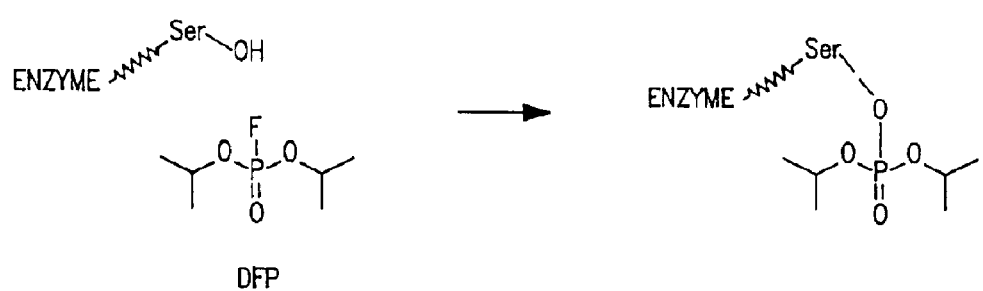
FIG. 8 is a schematic depiction of the DFP reaction with nucleophillic serine residues.
Figure 9:
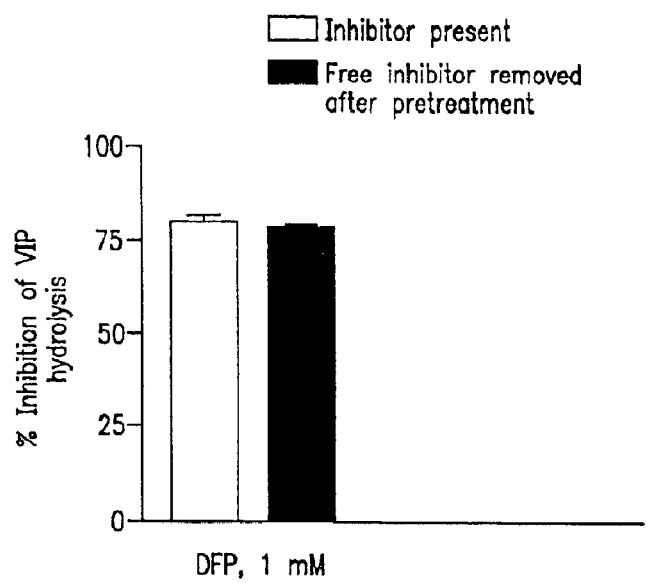
FIG. 9 is a bar graph showing irreversible inhibition of L chain peptidase activity by diisopropylfluorophosphate ester conjugated to biotin (top structure). L chain from clone U19 (1 $\mu$M) was incubated for 30 minutes with the inhibitor. Unbound inhibitors were removed by gel filtration. Peptidase activity was measured at 20 nM L chain with radiolabeled VIP substrate. Data are expressed as % inhibition relative to activity of the L chain subjected to gel filtration without inhibitor pretreatment (about 15,000 cpm).

The catalytic activity of autoantibodies to thyroglobulin and of various L chains capable of cleaving synthetic protease substrates is inhibited by diisopropylfluorophosphate (DFP), which reacts covalently with activated serine residues. See FIGS. 8 and 9.

The catalytic Abs to VIP contain a high affinity antigen binding subsite that is structurally and functionally distinct from the catalytic subsite. In the anti-VIP L chain, mutagenesis at the residues responsible for chemical catalysis (Ser27a, His93) produces reductions of turnover ($k_{cat}$) but minimal change in $K_m$, suggesting that residues responsible for transition state stabilization do not contribute in substrate ground state recognition. Mutagenesis at residues spatially distant from the catalytic subsite produced loss of binding to the substrate ground state (increased $K_m$) and also a gain in turnover, as predicted. It may be concluded, therefore, that the residues responsible for initial high affinity binding and the chemical cleavage step are not the same.

Antibodies to Transition State Analogs (TSAs) and Covalently Reactive Antigen Analogs (CRAAs):

Immunization with TSAs [37, 13, 38] has been proposed as a means to derive Abs that bind the transition state, and thus lower the activation energy barrier for the reaction. As described hereinabove, the commonly used phosphonate analogs contain a tetrahedral phosphorous atom and a negatively charged oxygen atom attached to the phosphorous. Formation of the transition state of peptide bond cleavage is thought to involve conversion of the trigonal carbon atom at the cleavage site to the tetrahedral state, and acquisition of a negative charge by the oxygen of the carbonyl group. The phosphonate TSAs may induce, therefore, the synthesis of Abs capable of binding the oxyanion structure and the tetrahedral configuration of the transition state. However, Abs to these TSAs, while capable of accelerating comparatively undemanding acyl transfer reactions, have not been reported to catalyze peptide bond cleavage. An antibody to a phosphinate TSA has recently been reported to slowly cleave a stable primary amide [11]. The anti-phosphinate Ab may permit superior transfer of a proton to the amide nitrogen at the scissile bond, compared to the more common anti-phosphonate Abs, which probably accounts for its better catalytic activity.

Figure 12A:
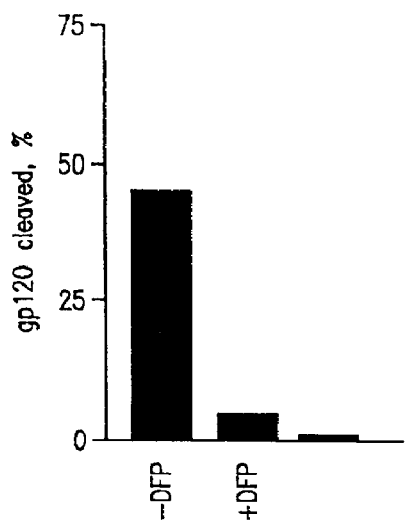
FIG. 12 is a graph showing antibody catalyzed cleavage of $^{125}$I-gp120 incubated for 1 hour with lupus IgG (50 nM) without and with DFP (10 $\mu$M). (B) $^{125}$I-gp120 from various strains incubated for 2 hours with L chain Lay2 (1 $\mu$M).
Figure 12B:
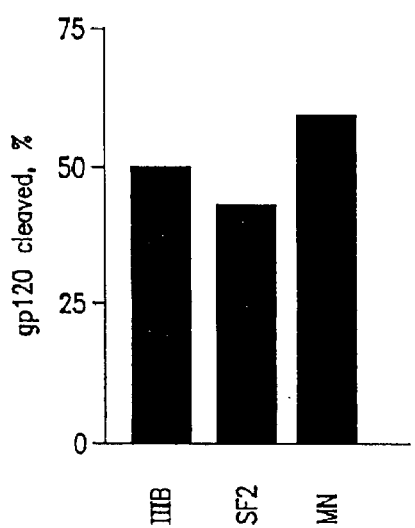

In the present example, our CRAA design is predicated on the following hypotheses: (a) as in enzymes, catalysis by Abs requires the participation of chemically activated amino acids to catalyze peptide bond cleavage. (For instance, the Ser hydroxyl group in serine proteases acquires nucleophilic character and the capability to mediate covalent catalysis due to formation of an intramolecular, hydrogen bonded network between the Ser, His and Asp residues); and (b) multiple structural elements are recognized by catalysts to achieve efficient transition state stabilization. It appears that the phosphonate TSA structure alone is an incomplete immunogen for induction of catalytic Abs, because this structure does not contain the elements needed to bind nucleophilic catalytic sites, or the sites in the catalysts responsible for S1 flanking residue recognition site. The antigen analogs of the present invention induce the synthesis of Abs with covalent catalytic capability, along with the ability to recognize basic flanking residue and the tetrahedral reaction center. Synthesis of the afore-mentioned type of catalytic Abs induced by CRAAs designed to bind the germline encoded, serine protease site in Abs is described herein. Electrophilic CRAAs capable of reacting with the nucleophilic serine residue in catalytic Abs will be prepared. These novel CRAAs will be used as immunogens, to force the utilization of the serine protease sites for the synthesis of the gp120 specific Abs. Immunization with the aforementioned CRAAs promotes clonal selection of B cells expressing the germline encoded catalytic sites. Further, the specificity for gp120 will be ensured by incorporating an appropriate antigenic epitope of gp120 on the flanks of the CRAA structure. See FIG. 10.

It should be noted that the conventional phosphonate TSA structure may also be useful, even if it is an insuffiecienct immunogen by itself. The incorporation of a basic residue at the P1 site in a phosphonate TSA might help induce catalytic Ab synthesis, because stabilization of the reaction center in the transition state can occur in conjunction with flanking residue recognition. Further, heterologous immunization, in which immunization with the phosphonate ester CRAA is followed by immunization with the phosphonate TSA, might permit development of the covalent catalytic site as well as the oxyanion stabilizing site. Ab sites that combine these functions will be catalytically more powerful than those utilizing only one of the above-mentioned mechanisms. Accordingly, methods for co-administering both TSAs and CRAAs to a patient are contemplated to be within the scope of the present invention.

Autoimmune disease is associated with the production of potent antigen-specific catalytic Abs. Abs capable of binding [39] and cleaving gp120 have been identified in lupus patients. Further, the L chains isolated from lupus-prone mice (MRL/1pr strain) cleave gp120.

IgG samples purified by affinity chromatography on protein G-Sepharose [41] from 17 HIV-1 positive patients and 10 lupus patients were analyzed for the ability to cleave $^{125}$I-gp120. Radiolabeling of electrophoretically pure gp120 (IIIB, AIDS Research and Reference Reagent Program, NIH) was by the chloramine-T method, followed by purification of $^{125}$I-gp120 by gel filtration. A single band of radiolabeled gp120 at 120 kD was observed by SDS-PAGE and autoradiography. Sixteen of 17 HIV-1 positive IgG samples were devoid of the gp120 cleaving activity, and one showed barely detectable activity. In comparison, 3 of 10 lupus IgG samples showed readily detectable gp120 cleavage. See FIG. 11. No hydrolysis of $^{125}$I-albumin by the IgG samples was evident, suggesting that the observed gp120 hydrolysis is not a nonspecific phenomenon. In separate experiments, L chains were purified from one of the gp120 cleaving lupus IgG samples and from the serum IgG of MRL/lpr mice. This was done by reduction and alkylation of the IgG and FPLC gel filtration, using protocols described previously for isolation of VIP cleaving L chains from human monoclonal and polyclonal IgG [9, 28]. $^{125}$I-gp120 cleaving activity was evident in the fractions corresponding to the L chain peak from both the the lupus patient and the MRL/lpr mice (25 kD). The identity of the L chains recovered from the FPLC column was confirmed by SDS-PAGE and immunoblotting as described previously [28]. Similar L chain fractions from HIV-1 positive IgG and BALB/c IgG did not display the gp120 cleaving activity. The specific activities of $^{125}$-gp120 cleavage by the lupus L chains, MRL/1pr L chains and trypsin were (expressed as the reduction in the intact gp120 band area in arbitrary units/nM catalyst/h incubation time), 31, 307 and 204 respectively. Note that the catalyst subpopulation probably constitutes a small fraction of the L chains, implying that the true specific activity of the catalytic L chain must be greater than the value cited above.

In the presence of a serine protease inhibitor (0.3 mM diisopropylfluorophosphate), gp120 cleavage by IgG from a lupus patient was essentially completely inhibited (FIG. 12A). In comparison, inhibitors of metalloproteases, cysteine proteases and acid proteases (EDTA, iodoacetamide, Pepstatin A) were without effect on the reaction.

Further proof for L chain catalyzed gp120 cleavage has come from identification of a monoclonal L chain with this activity. Twenty nine monoclonal L chains purified from patients with multiple myeloma, three recombinant VL domains of these L chains, a recombinant L-chain with VIP hydrolyzing activity [10] and polyclonal anti-VIP Abs[2] were screened for the ability to hydrolyze $^{125}$I-gp120. One monoclonal L-chain from a multiple myeloma patient with gp120 hydrolyzing activity was identified (Lay2). The remaining Ab samples were devoid of activity. The gp120 hydrolyzing activity coeluted from a gel filtration column with the L-chain protein peak. Nearly equivalent cleavage of gp120 by Lay2 was observed in physiological buffers and nutrient media (PBS, HBSS and RPMI1640). Four radiolabeled gp120 cleavage products of mass approximately 80 kD, a smear around 50 kD, 20 kD, and <6 kD were evident by nonreducing electrophoresis. The 80 kD band underwent further diminution in size under reducing conditions, suggesting that it contained disulfide bonded fragments. Identical product profiles were observed using $^{125}$I-gp120 preparations derived from HIV-1 strains IIIB, SF2 and MN (FIG. 12B). Like the lupus IgG, the activity of the L chain was inhibited by the serine protease inhibitor DFP, but not by inhibitors of other types of proteases.

Figure 13:
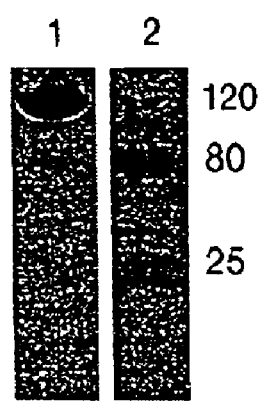
FIG. 13 is an immunoblot of a reducing SDS-gel showing hydrolysis of unlabeled gp120 (11 $\mu$M; SF2, Chiron) by L chain Lay2 (20 $\mu$M) (Lane 2).
Figure 14:
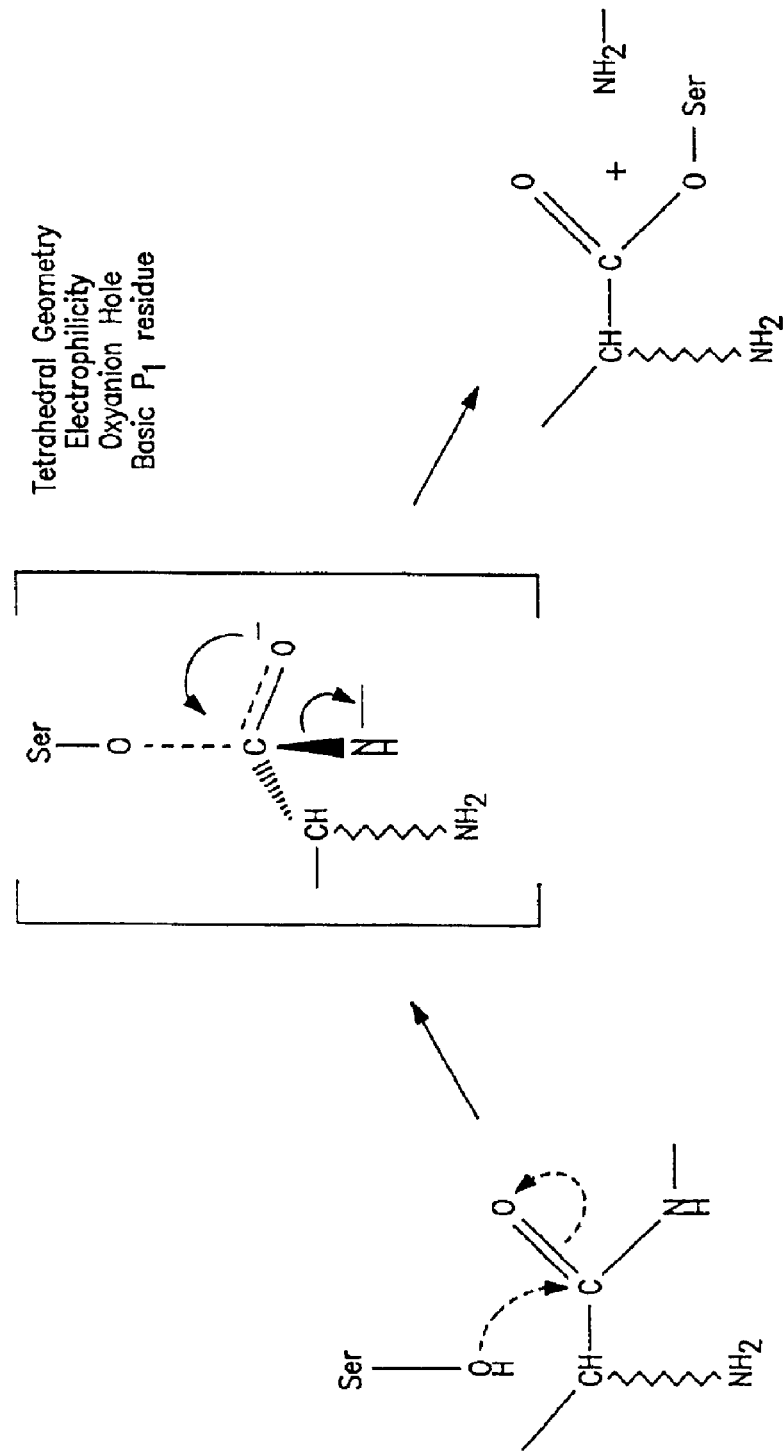
FIG. 14 is a schematic drawing of the putative transition state of acyl-enzyme formation during peptide bond cleavage by serine proteases. The acyl enzyme complex (right structure) is deacylated by an attacking water molecule.

To confirm that the cleavage reaction was not an artefact associated with the radioiodination of gp120, cleavage of the unlabeled protein was studied (FIG. 13). The cleavage products were identified by immunoblotting of reducing SDS-electrophoresis gels with an anti-gp120 antibody previously described to recognizes proteolytic breakdown products of the protein [35]. Increasing hydrolysis of gp120 was evident at increasing L chain concentrations, estimated as the reduction in intensity of the 120 kD substrate band. This was accompanied by increasing accumulation of the 80 kD and other cleavage products. The cleavage profiles of unlabeled gp120 and radiolabeled gp120 analyzed under reducing conditions were identical, except that the intensities of the individual bands were different, which is probably a reflection of the methods used for detection of the two types of substrates (immunoblotting versus $^{125}$I-labeling at Tyr residues followed by autoradiography).

The initial rates of the cleavage reaction measured at 20 nM L chain and increasing gp120 concentrations (10–300 nM) were saturable (apparent $K_m$ value 30 nM; Vmax0.06 nmol gp120/nmol Lay2/h). The nM Km value suggests comparatively high affinity binding. Trypsin-catalyzed gp120 cleavage analyzed in parallel was nonsaturable at concentrations up to 1 $\mu$M, suggesting low affinity recognition. VIP inhibited the cleavage of $^{125}$I-gp120 by the L chain ($K_i$ of VIP, 620 nM). The Lay2 L chain also hydrolyzed radiolabeled VIP with a $K_m$ of 144 nM [40]. Thus, VIP appears to bind the L chain about 5–21 fold less strongly than gp120. Two short regions of homology have been identified between gp120 and VIP, which might underlie reactivity of both polypeptides with the catalyst.

Figure 10:
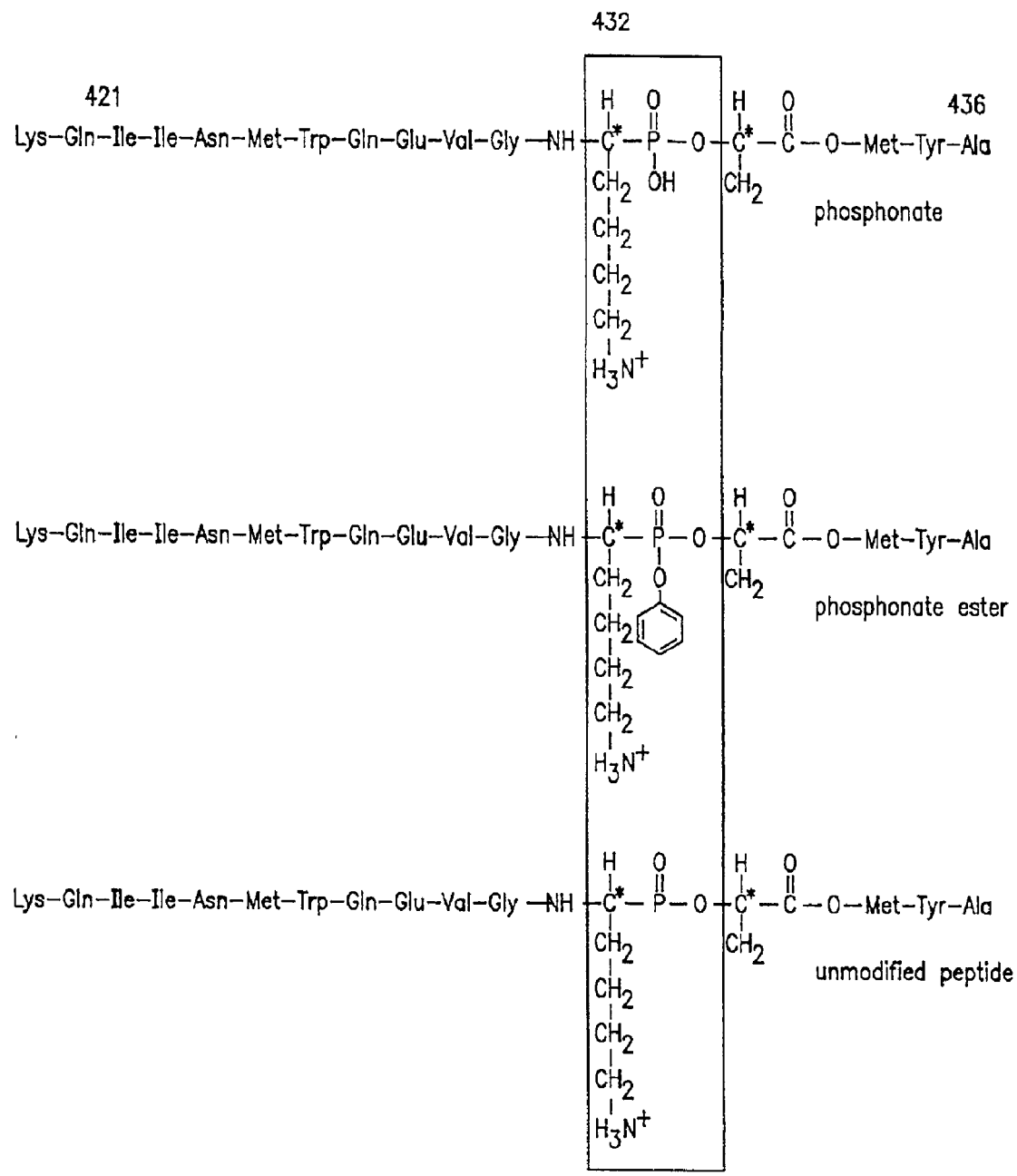
FIG. 10 depicts exemplary immunogen structures contemplated for use in the present invention. The box shows the structure around the targeted cleavage site (Lys432-Ala433). Flanking residues are indentical in the three immunogens. Amino acid numbers are those in full-lenghth gp120.
Figure 11:
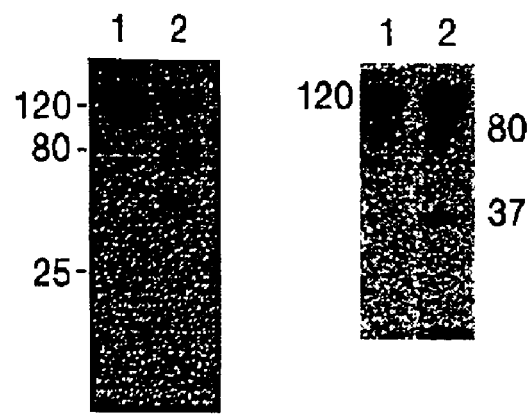
FIG. 11 is an autoradiogram of a non-reducing gel showing the hydrolysis of $^{125}$I-gp120 (100 nM) incubated with 50 nM IgG from a lupus patient (lane 2, left panel) and 11 nM L chains from MRL/lpr mice (lane 2, right panel). Lane 1 in the left and right panel show equivalent amounts of the substrate incubated with noncatalytic IgG from an HIV-1 positive subject and L chains from BALB/c mice. Incubation, 2 hours at 37° C.

Methods are provided for the synthesis of peptide analog formulations that elicit the synthesis of specific and efficient catalytic Abs capable of protecting against HIV infection. Earlier studies have suggested that polyreactive catalytic activity of germline encoded Abs can be recruited and improved by immunization of mice with the serine-reactive CRAA of a gp120 peptide. The elicitation of a catalytic Ab response should provide superior protection against HIV-1 infection compared to a noncatalytic Ab response. The following synthetic immunogens will be prepared and assessed:

A) synthetic immunogens
  a) the phosphonate transition state analog (TSA) of a B cell epitope of gp120 (residues 421–436) conjugated to a T-helper epitope from tetanus toxoid (residues 830–844) [designated B-T epitope];
  (b) the phosphonate ester CRAA of the B-T epitope; and
  (c) the unmodified peptide form of the B-T epitope.
(B) Immunize non-autoimmune mice (strain B10.BR) and autoimmune mice (MRL/lpr) with the three immunogens from (A) and study the following activities of IgG purified from the sera:
  (a) binding and cleavage of the phosphonate B-T epitope, the phosponate ester B-T epitope and the unmodified B-T epitope;
  (b) binding and cleavage of monomer full-length gp120; and
  (c) binding and cleavage of native cell-surface-bound gp120.

Immunogens

The prototype vaccine capable of eliciting catalytic antibodies to HIV contains: 1) an epitope to which B cells can make high affinity antibodies (B epitope); 2) an epitope that is bound by MHC class II antigens and presented to T cells (T epitope); and 3) a structural mimic of the transition state formed during peptide bond cleavage, which is intended to provoke the synthesis of antibodies capable of stabilizing the transition state, and thus catalyzing the cleavage reaction.

B Epitope component: Loss of infectivity following cleavage of gp120 can be achieved by directing the catalyst to cleave a peptide bond located in an epitope of gp120that plays an important role in the infection process. Note that cleavage of gp120 at a bond distant from the biologically important determinants may also lead to loss of gp120 function, because the conformation of the gp120 fragments may be altered "globally" relative to the parent protein. The probability of neutralizing viral infectivity can be increased by directing the Ab to recognize an epitope that is a known target of neutralizing Abs. Cleavage of the CD4 binding site is an attractive mechanism to achieve HIV neutralization for the following reasons: CD4-gp120 binding is an essential step in HIV entry into host cells; cleavage of the CD4 binding at the 432–433 bond by trypsin is known to block the ability of gp120 to bind CD4; Abs to the CD4 binding site are known to inhibit HIV infection; the CD4 binding site on native gp120 expressed on the HIV surface is exposed to the environment (as opposed to several other epitopes of monomeric gp120 that are buried in native gp120 oligomers) [32]; and, the CD4 binding site is quite conserved in different subtypes of HIV-1. The linear peptide sequence composed of gp120 residues 421–436 has been selected as the B epitope component of the immunogen in the present project (KQIINMWQEVGKAMYA; FIG. 10). Mutagenesis studies have shown that this region of gp120 make important contributions in CD4 binding.

Transition state analog component and covalently reactive antigen analog component: Catalysis occurs when the transition state is stabilized more than the ground state. In the present invention the antigen analogs act to recruit catalytic function while retaining the ability of Abs to bind the ground state of the antigen. The latter property is necessary to obtain gp120-specific catalysts, as opposed to Abs that cleave various polypeptides non-specifically. Inclusion of the gp120 peptide sequences flanking the targeted peptide bond will confer specificity for gp120. The key structural features responsible for stabilization of the transition state of peptide bond cleavage by serine protease-like catalytic Abs are shown in FIG. 14 and may include: (a) The tetrahedral, electrophilic carbon atom formed in the transition state at the scissile peptide bond, capable of binding nucleophilic serine residues in the catalyt; (b) The oxyanionic structure formed at this carbon, which can be stabilized by ion pairing with residues like Asn, Gln or Arg in the catalyst (the so-called oxyanion hole); and (c) The basic residue on the N-terminal side of the scissile peptide bond, recognition of which may occur by ion pairing with acidic residues such as Asp or Glu located within or close to the catalytic site in the Abs. Note that the positively charged side chain of the flanking residue, although not directly involved in bond making and breaking processes during catalysis, can occupy a different spatial position in the transition state than in the ground state. This is possible because the partial double bond character of the scissile peptide bond will be lost upon formation of the transition state, permitting rotation around this bond, and consequent changes in the positions of remote groups. The feasibility of such remote spatial changes in the transition state has been deduced by computational modeling of a peptide substrate in the sp2 (ground state) and sp3 (transition state) configurations at the scissile bonds.

A TSA and a CRAA which comprise phosphonate analog and a phosphonate ester analog, respectively, will be assessed. In both cases, the tetrahedral phosphonate atom serves as the analog of the scissile peptide bond carbon atom linking residues 432 and 433 in gp120. In the phenylester configuration shown in FIG. 10, the phosphorous atom acquires a partial positive charge, just as the scissile bond carbon atom carries the partial positive charge required for its reaction with nucleophilic serine residues. Peptidic O-phenylphosphonates have previously been described to be capable of irreversibly inactivating various serine proteases by forming a covalent bond with the oxygen atom of the active site serine residue [29]. Sampson and Bartlett and others [23, 24] have established the chemical synthesis needed to prepare the phenyl ester at the phosphorous atom, and to attach peptide sequences flanking the phosphonate ester.

Twelve and four amino acids are present, respectively, on the N and C terminal sides of the TSA/CRAA structure, corresponding to the sequence of residues 421–436 of gp120. A basic residue has been incorporated at the P1 position of the CRAA-gp120 to exploit the existence of the germline encoded, basic residue-specific catalytic site in Abs. The presence of the basic residue, along with the phosphonate phenylester structure, promotes tight binding to catalytic site, and thus promotes the ability of the CRAA-gp120 to selectively stimulate the clonal proliferation of B cells synthesizing the catalytic sites.

It should be noted that the above phosphonate ester CRAA of the B epitope is structurally distinct from previous phosphonate TSAs applied to raise esterase Abs [13, 38]. The conventional phosphonate TSAs contain an anionic oxygen attached to the phosphorous, which can bind the oxyanion hole found in the catalysts. The phosphonate TSAs, however, can not react with nucleophilic serine residues in the catalytic site. A phosphonate TSAs of the Phe-Ile peptide bond reportedly did not induce the formation of amidase catalytic Ab formation [41].

The phosphonate ester analog described above will be compared to a phosphonate TSA of the B epitope for the following reasons: (a) the immunogen described in the afore-mentioned study did not contain a basic residue at the P1 position, which would work against recruitment of the germline catalysts for synthesis of peptidase Abs; and (b) while immunization with a phosphonate analog alone may be insufficient to provoke peptidase Ab synthesis, heterologous immunization with the phosphonate and phosphonate ester analogs may lead to a good peptidase Ab response, because the heterologous immunization can be anticipated to select for the oxyanion hole (phosphonate immunization) as well as the nuqleophilic serine residues (phosphonate ester immunization). Such a coimmunization using the gp120 phosphonate and phosphonate ester immunogens is contemplated to be within the scope of the present invention.

T epitope component: To recruit T cell help for synthesis of anti-gp120 Abs, a fifteen amino acid peptide (QYIKANSKFIGITEL) corresponding to residues 830–844 of tetanus toxin will be placed on the N terminal side of the B epitope. The presence of the T epitope in the vaccine construct eliminates the need to conjugate the B epitope to a large carrier protein. Several previous studies have shown that comparatively short linear peptides that include a T and a B epitope are capable of provoking efficient Ab synthesis to the B epitope [42]. The tetanus toxin T epitope to be employed in the present invention is known to serve as a T epitope in hosts expressing diverse class II alleles, and has been characterized, therefore, as a "universal" T epitope [43]. Further, a gp120 B epitope linked to this T epitope is described to induce anti-gp120 Ab synthesis. The "universality" of the T epitope, although deduced from human studies, probably extends to the mouse, because class II restrictions tend to be conserved phylogenetically. Regardless of the possible differences on this point between man and mouse, the mouse strains to be utilized in the present invention have been matched for class II alleles involved in recruitment of T cell help for Ab synthesis ($A^k E^k$ haplotype), eliminating concern that differential T helper recruitment might contribute to variations in catalytic Ab responses.

Assembly of immunogens: Synthesis of the 31 residue ground state B-T construct (designated unmodified B-T epitope) composed of tetanus toxin residues 830–844 at the N terminus and gp120 residues 421–436 at the C terminus will be done by conventional solid phase synthesis on an Applied Biosystems synthesizer. Mass spectrometry and $^1$H and $^{13}$CNMR will be done to confirm the structures.

The TSA and CRAA of the B-T epitope will contain the phosphonate and the phosphonate ester structures at the targeted cleavage site. These are novel reagents, but their synthesis should not present problems. Standard organic chemistry techniques utilized previously for synthesis of TSAs and other types of enzyme inhibitors [23,24].

A brief overview of the synthetic scheme is as follows. The phosphinate isostere of lysine will be prepared from the diphenylmethlyamine salt of hypophosporus acid and 6-benzylcarbamatohexanal, followed by removal of the diphenylmethyl group in acid. The required flanking peptides (tetanus toxoid residues 830–844 extended with gp120 residues 421–431; gp120 residues 432–436) are prepared by conventional solid phase synthesis, except that the peptide corresponding to the C terminal fragment contains 2-hydroxy-6-carbobenzyloxyaminohexanoic acid instead of the N terminal lysine. Other basic side chains are protected with the carbobenzyloxy group and acidic side chains are protected with a benzyl ester group. Protected peptides will be attached to the phosphinate lysine isostere by classical solution phase peptide synthesis methods. The final peptide phosphonate phenyl ester structure will be prepared by oxidative coupling of the phosphinate with phenol. This same synthesis scheme will be used used for preparation of the phosphonic acid by converting the phosphinate to the phosphonic acid monoester by treatment with bis (trimethylsilyl)acetamide in acetonitrile followed by aqueous triethylamine, carbon tetrachloride, and lithium exchange on AG-X-50 ion exchange resin [23; scheme h and I]. Mass spectrometry and NMR will be done to confirm the structures.

Immunization of Mice

Two strains of mice will be studied for Ab responses to 4 immunogen constructs, BR10.BR and MRL/lpr. Immunizations will be done with:

a. B-T epitope (residues 421–436 of gp120 linked to residues 830–844 of tetanus toxin).
b. Phosphonate analog of the B-T epitope at residue Lys432. (TSA)
c. Phosphonate ester analog of the B-T epitope at residue Lys432. (CRAA)
d. Phosphonate ester analog followed by phosphonate analog the B-T epitope (TSA+CRAA; heterologous immunization).

Conventional immunization methods will applied to induce Ab synthesis. Three intraperitoneal and one intravenous injection of the immunogens (about 100 μg peptide each) will be administered. The final immunization will be carried out intravenously. Two adjuvants will be tested: RIBI and alum. Alum is approved for human use and has previously been shown to provoke Ab synthesis to a B-T epitope similar to those proposed in the present invention. RIBI is a low toxicity replacement for Freund's Complete Adjuvant, and reproducibly facilitates good Ab responses to a variety of Ags. Sera will be prepared from retroorbital plexus bleeds obtained from the mice at five time points over the course of the immunization schedule. Splenocytes will be harvested and processed for preparation of Fv phage display libraries for structure-function studies. Analysis of two adjuvants is advantageous because the quality and magnitude of Ab responses to vaccines can be influenced by adjuvants, via effects of the cytokines and TH subpopulations recruited by the adjuvants on B cell development and clonal selection [44]. Thus, a total of 16 groups of mice will be studied (4 immunogens×2 mouse strains×2 adjuvants), each composed of 5 animals.

Low affinity, antigen-nonspecific peptidase antibodies are already present in preimmune repertoire. Provided that the germline gene encoding the nonspecific peptidase activity is recruited for the Ab synthesis, immunization with the CRAAs will result in synthesis of gp120-specific catalytic Abs. Humans and mice with autoimmune disease are prolific producers of Ag-specific catalytic Abs, suggesting that the diseased immune system efficiently recruits the germline gene encoding the catalytic site, and permits maturation of the catalytic sites to become specific for individual Ags over the course of the immune response. The MRL/lpr mouse strain is genetically prone to autoimmune disease, and has previously been observed to be capable of high level catalytic antibody production. Further, the L chains from the serum of preimmune MRL mice express gp120 cleaving activity. Thus, a subset of antibodies formed by immunization of MRL/lpr mice with the disclosed immunogens can be anticipated to express gp120-specific catalytic activity. It is relevant that gp120-binding Abs found in lupus patients are directed, in part, to the gp120 B epitope included in the disclosed immunogens [39]. The BR10.BR mouse strain is not prone to autoimmune disease. The results from this strain will reflect the ability of the disclosed immunogens to stimulate catalytic immunity to gp120 in the healthy immune system. B10.BR mice and MRL/lpr mice have identical haplotypes at the class II loci responsible for T cell restriction of Ab synthesis ($A^kE^k$), ensuring that any differences in catalytic Ab synthesis between the two strains will not be due to the class II restriction.

Ab Binding Activity

Abs synthesized in response to the CRAAs should bind the transition state of the peptide bond cleavage reaction better than the ground state, permitting catalysis to occur. The strength of the binding of the Abs to the CRAAs/TSAs will serve as an predictor of the Ab catalytic activity. Further, if the B epitope in the immunogen exists in approximately the same conformation in the immunogen and the full-length gp120, the Abs will also bind the full-length protein. Finally, if the epitope is exposed as in the native gp120 known to exist in the form of oligomers on the viral surface, the Abs should also bind the oligomeric gp120 structure.

Unmodified B-T epitope and TSA B-T epitope and CRAA B-T epitope: The binding of the three forms of the B-T epitope, i.e., the unmodified, phosphonate, and the phosphonate ester form, will be compared by ELISA. Apparent values of binding strength will be assessed by competition assays (as IC50 values), using ELISA plates coated with the unmodified B-T epitope (about 50 $\mu$g/ml) as the solid phase and the unmodified, phosphonate and phosphonate ester B-T epitope as the soluble competitor. The binding will be measured using peroxidase coupled anti-mouse IgG followed by addition of the substrates (o-phenylene diamine and hydrogen peroxide). Since polyclonal preparations are to be studied, the binding curves may deviate from simple sigmoidal binding isotherms. The IC50 values for the individual ligands will serve, nevertheless, as valid indicators of the average binding affinity of the Abs.

The following relationship could be applied to predict the catalytic rate acceleration: $Ki/Kd=k_{cat}/k_{uncat}$, where Ki and Kd are the equilibrium dissociation constants of the TSA and the unmodified B-T epitope, respectively, and $k_{cat}$ and $k_{uncat}$ are the first order rate constants for the catalyzed and uncatalyzed reactions, respectively. IC50 values could be substituted in this equation to predict the rate acceleration, but the predicted value will be an average of the activity of several Abs, because the IgG samples to be studied are mixtures of different Abs. The binding assays will be conducted at 4° C. in the presence of diisopropylfluorophosphate (DFP) to minimize interference with measurement of the binding parameters due to peptide cleavage. DFP, a known serine protease inhibitor, has been observed in previous studies to uniformly inhibit the catalytic activity of Abs. Reduction of the reaction temperature will reduce the rate of the catalytic reaction. Note that Km values estimated from catalysis assays will help confirm the validity of the IC50 as an indicator of binding strength.

Solution phase assays will be conducted to confirm that avidity effects due to the antigen "carpeting" on the solid phase do not lead to misleading binding estimates. The solution phase assays will be carried out using the $^{125}$I-radiolabeled B-T epitope. Radiolabeling of the peptide will be done using the chloramine-T method as described previously [2]. [The B-T epitope contains one Tyr, corresponding to gp120 residue 435]. Ab-Ag complexes will be trapped using protein G-Sepharose and the binding determined by counting the radioactivity in a γ-spectrometer. As before, the binding will be studied at various concentrations of the TSA/CRAA competitors, permitting estimation of the binding strength of the unmodified epitope and its TSA/CRAA.

Purified gp120 and cell-surface expressed gp120: Ab binding by purified gp120 and cell-surface gp120 will be measured to determine whether the targeted B epitope is accessible to the Abs in the full-length oligomeric form of the protein. Recombinant gp120 expressed in a mammalian cell line will be employed to assure that the glycosylation pattern of the protein is similar to that in HIV-infected cells. Competitive ELISA using gp120 coated on a solid phase will be performed to determine the apparent binding strengths of the Abs. Competitor ligands to be studied are the full-length gp120 and the three B-T epitopes to which the Abs are elicited (phosphonate TSA, phosphonate ester CRAA and the unmodified B-T epitope). The relative reactivity of the synthetic immunogens and the full-length gp120 will be estimated from the IC50 values (apparent Ki) of the competitor ligands. Near equivalent IC50 values for the full-length gp120and the unmodified B-T epitope will indicate that the targeted B epitope exists in a near-equivalent conformation ln the two molecules. Observations indicating stronger binding of the Abs to the phosphonate or the phosphonate ester of the B-T epitope compared to full-length gp120 will indicate that the Abs may display catalytic activity. As described above, solution phase assays using radiolabeled gp120 will be carried out to confirm the absence of ELISA artefacts, such as increased binding avidity due to the ligand immobilization.

HIV-1 infected cells of the H9 T cell line express gp120 on their surface. The majority of cell-surface gp120 mimics the form of adherent virus particles. The cell-surface gp120 is thought to exist in an oligomeric state similar to the aggregation status of the gp120 on the surface of the virions. Ab reactions with the cell-surface expressed gp120, thus, have been held to indicate the ability of the Abs to recognize virion-bound gp120.

In the present invention, H9 cells obtained from the NIH AIDS Repository will be grown in RPMI/10% FCS in 5% $CO_2$. The cells ($10^6$/ml) are infected with the culture supernatant containing HIV-1 strain MN (AIDS Repository) for 2 hours at 37° C. Following washing, the cells are cultured for about 1 week. Binding of various concentrations of IgG (1 nM-1 $\mu$M) will be determined by incubation with an appropriate number of the intact cells for 4–6 h at 4° C. in round-bottomed 96 well plates in the presence of 1 mM DFP, followed by washing of the cells to remove unbound Ab, incubation with rabbit antimouse IgG conjugated to peroxidase, development of the reaction with hydrogen peroxide and o-phenylenediamine, and quantitation of the optical density at 490 nm using an ELISA reader. Controls will include the preimmune IgG and an Ab known to be reactive with cell-surface gp120 (available from the NIH AIDS repository). Ab binding to the cells can also be studied by flow cytometry, using a fluorescent second Ab for detection of the bound anti-gp120 Ab as described [45]. This procedure permits determination of apparent Ab affinity by estimation of Ab association and dissociation rates.

Competition experiments will be carried out in which the B-T epitope constructs or soluble full-length gp120 will be permitted to act as competing ligands for Ab binding to the cells. As in the competition studies described in the preceding paragraph, the IC50 values of the B-T epitopes will estimate the relative strengths of the Ab binding to the B epitope. To minimize gp120 cleavage by the Abs, the incubations will be conducted at 4° C. Diisopropylfluorophosphate, which is an effective inhibitor of Ab catalysis, can also be included in the incubations. Cell viability will be estimated at the end of the binding reaction by trypan blue exclusion tests, to confirm that the inhibitor (and other experimental conditions) does not disrupt cellular integrity, which could potentially perturb the oligomeric structure of the gp120.

Screening for Catalytic Activity:

IgG purified from sera by affinity chromatography on protein G-Sepharose will be screened for catalytic activity using the unmodified B-T epitope as the substrate. Initial screening assays will be carried out at 10 $\mu$M substrate and 0.25 $\mu$M IgG concentrations with incubations times of 1–2 hours. Even with an apparent turnover as low as 0.1/min, the products should accumulate to concentrations of about 3 $\mu$M (30% of initial substrate concentration). The reaction mixtures will be analyzed by reversed-phase HPLC with detection at 214 nm (trifluoracetic acid/acetronitrile gradient). Product concentrations will be computed from areas under the product peaks. Controls will include preimmunization IgG.

All IgG samples will also be screened for cleavage of full-length gp120. $^{125}$I-gp120 will be the substrate. Radiolableing of gp120 (recombinant MN expressed in CHO cells) is by the chloramine-T method followed by resolutive FPLC to obtain electrophoretically homogeneous $^{125}$I-gp120. SDS-electrophoresis and autoradiography will be applied to visualize product bands. Procedures permitting rapid sample handling have been described. About 50 IgG samples can be screened for the activity per day. Unlabeled gp120 will be used as substrate to confirm that the cleavage reaction is not an artefact associated with the radiolabeling procedure. Immunoblotting of SDS-PAGE gels of the reaction mixtures with an anti-gp120 Ab capable of recognizing various proteolytic fragments of gp120 will be applied for this purpose.

Purity of the IgG used as catalyst will be established by SDS-PAGE. Retention of the catalytic activity in the Fab fractions and IgG prepared by gel filtration under denaturing conditions (6 M guanidinium chloride) will confirm that the catalytic activity is due to Abs as previously described [36].

The assays will be done in the absence and presence of human serum to assess whether protease inhibitors found in serum influence catalytic Ab activity. In preliminary studies, serum has been found to be without effect on gp120 or thyroglobulin cleavage by Abs isolated from lupus serum. Based on these results, serum inhibitor-resistant Abs should also be present in mice.

Cleavage site specificity: The product fragments generated by cleavage of the unmodified B-T epitope and of full-length gp120 will be identified, permitting deduction of the cleavage site(s). The B-T epitope fragments separated by HPLC will be subjected to N-terminal amino acid sequencing and FAB-mass spectrometry to identify the cleavage site(s), as previously described (1,2). In the case of the full-length gp120 substrate, the reaction products will be separated by SDS-electrophoresis, blotted onto PVDF and the blotted polypeptides subjected to N-terminal sequencing, permitting identification of the cleavage sites by comparison with the sequence of gp120. Controls will include IgG from preimmune mice.

Trypsin will be included as a positive control. Trypsin can be expected to cleave the B-T epitope at multiple peptide bonds that are flanked by a Lys or Arg residue, i.e., at residues 421–422 and 432–433 in the B epitope and at residues 833–834 and 837–838 in the T epitope. In comparison, recruitment of the catalytic activity in Abs due to the presence of the phosphonate or phenylphosphonate ester structure, should cleave the the B-T epitope mainly at the Lys432-Ala433 peptide bond by IgG. It is possible that an alternative result may be observed. Ag-specific catalysts can be synthesized by immunization with ground state antigens. Thus, catalysts capable of cleaving the substrates at peptide bonds other the 432–433 bond may be found, because the germline encoded activity present in the preimmune repertoire may recognize basic residues without regard to the overall structure of the antigen epitope [36, 40]. The extent to which the cleavage reaction occurs preferentially at residues 432–433 will indicate the importance of the phosphonate/phenylphosphonate ester structure in recruiting the catalytic site. Similarly, the extent to which the cleavage of full-length gp120 is confined to peptide bonds located within residues 421–436 will indicate the importance of this peptide epitope in recruiting catalytic activity that is specific for gp120.

Substrate specificity These studies will be performed to assess the therapeutic use of the antibody catalysts. Cleavage of various peptide and protein substrates will be studied. Several radiolabeled polypeptides are available to study the substrate-specificity profile: (a) $^{125}$I-albumin; (b) $^{125}$I-thyroglobulin; (C) $^{125}$I-VIP; and, (d) $^{125}$I-IgG. Hydrolysis of the proteins is indicated by appearance of lower mass product bands visualized by electrophoresis and autoradiography. VIP hydrolysis is measured by precipitation of the intact peptide with trichloroacetic acid or by reversed-phase HPLC [2]. A larger panel of randomly selected polypeptides (n>10; commercially available polypeptides, e.g., casein, collagen, etc.) will also be examined by inhibition assays, i.e., their ability to inhibit 125I-gp120 hydrolysis by the catalyst. Inhibition of the reaction is indicated by reduced depletion of the 120 kD gp120 band.

Kinetics: Kinetic studies will be done to determine the apparent rate constant and catalytic efficiency ($k_{cat}/K_m$). The unmodified B-T epitope and full-length gp120 will be used as substrates. The kinetic constants will be determined from assays conducted at varying concentrations of the substrates. If the the sera contain catalytic Abs mixed with noncatalytic Abs capable of binding the epitope, the binders may protect the epitope from cleavage by the catalyzers. To differentiate between these two pools, the serum IgG will be adsorbed onto an immobilized inhibitor that can binds the catalytic Abs but not the noncatalytic Abs. Such inhibitors are available. Because such inhibitors do not contain a gp120 epitope, they will not bind noncatalytic Abs induced by immunization with the gp120 B-T epitope. Biotin will be attached to the inhibitor to permit immobilization using avidin coated plates. Following incubation of the serum IgG from immune mice with excess immobilized inhibitor, the supernatant will be analyzed by ELISA for binding to the unmodified B-T epitope. An absence of binding will suggest that the noncatalytic Abs to the epitope are not present in significant amounts. Further, the bound Abs may be elutable with hydroxylamine, pH 9 or greater, which may cleave the covalent bond between the Abs and the inhibitor. The eluted Abs, which will be deficient in noncatalytic Abs to the B-T epitope, can then be analyzed for kinetic parameters.

Nanomolar or lower Km values will indicate high affinity antigen binding activity. Observations of equivalent Km and kcat values for the two substrates will suggest that residues 421–436 located in the synthetic immunogen adopt a conformation similar to that in gp120. Concerning values of the apparent rate constant, the IgG preparations should display more rapid turnover than that observed previously using polyclonal Ab preparations, because the immunogens of the invention are expressly designed to promote the recruitment and improvement of catalytic sites over the course of the immunization procedure.

The inhibition of IgG catalyzed cleavage of the unmodified B-T epitope by the phosphonate and phosphonate ester of the epitope will also be assessed. Reduced hydrolysis will indicate that the phosphonate and phosphonate ester peptides are competitive inhibitors of the binding of the B-T epitope and/or serve as alternate substrates. When inhibition is seen, the $K_i$ value will be measured to assess the relative reactivity of the IgG with the B-T epitope and its TSA/CRAAs. To determine whether the TSA/CRAAs are used as substrates, their cleavage by the IgG will be studied by RP-HPLC separation of product peptides and identification of the product peptides by amino acid sequencing. If the catalysts are capable of cleaving multiple peptide bonds promiscuously, the TSA/CRAA peptides may be cleaved by the catalysts. On the other hand, if the Abs cleave exclusively at the Lys432-Ala433 bond, the TSA/CRAAs will not serve as substrates because they contain noncleavable analogs of the peptide bond at this position.

Cleavage of cell-surface expressed gp120: To confirm that the catalytic antibody activity is directed to the biologically relevant form of the gp120, i.e., virion bound oligomeric gp120. Biosynthetically radiolabeled gp120 expressed on the cell surface will serve as the substrate. gp120 radiolabeling will be done by growing HIV-infected H9 cells in $^{35}S$-labeled methionine (in Met-deficient medium). The cells will be treated with varying concentrations of the IgG fractions from preimmune and immune mice. Cell extracts will be prepared using a mild detergent (0.1% Triton-X-100), which should be sufficient to release the radiolabeled gp120 into the supernatant. The gp120 (and its fragments) will be immunoprecipitated from the cell extracts using an available rabbit anti-gp120 Ab, which is known to bind various tryptic fragments of the protein [35]. SDS-electrophoresis will be employed to separate the reaction products. Disappearance of the intact gp120 band and appearance of lower mass fragments will indicate the cleavage of cell-surface bound gp120. Controls will include immunoprecipitation of the cell extracts with nonimmune rabbit IgG, in which case no radioactivity should be precipitated. Immunoblotting of the gels with anti-gp120 Abs will be carried out to confirm that the immunoprecipitated material represents gp120 fragments.

Confirmatory experiments that the Abs recognize the conformation of gp120 expressed on the surface of HIV-1 will also be performed. Sucrose density gradient purified MN-virus preparations as the substrate (available from Advanced Biotechnologies) will be used. Following incubation of the virus with the Abs, gp120 cleavage will be determined as described for cell-surface expressed gp120, i.e., detergent extraction, electrophoresis and immunoblotting with the anti-gp120 Ab known to bind gp120 cleavage fragments.

Immunization with the B-T epitope immunogens will elicit Abs that bind full-length soluble and cell-surface expressed gp120, because the targeted epitope in gp120 is a part of the CD4 binding site, which can be assumed to be exposed on the protein surface (as opposed to being buried in the interior of the protein). Moreover, the targeted epitope is conserved in different HIV strains. Thus, synthesis of broadly reactive Abs is expected.

Preimmune IgG from non-autoimmune mice will be devoid of the ability to catalyze the cleavage of the targeted epitope in gp120. Similarly, IgG from non-autoimmune mice immunized with the unmodified B-T epitope will express little or no gp120 cleaving activity.

Preimmune IgG from autoimmune mice may display low-level cleavage of gp120, but the activity will not be highly specific for gp120. Immunization of the autoimmune mice with the unmodified B-T epitope will render the catalytic activity specific for gp120, but improvements in catalytic turnover are not predicted from the structure of the immunogen. In comparison, the B-T epitope TSA and CRAA are designed to provoke the synthesis of Abs that combine the ability to bind the ground state of gp120 as well as the transition state of the peptide bond cleavage reaction. Thus, the TSA and CRAA immunizations are predicted to elicit the synthesis of Abs that display bind gp120 with high affinity (low values of apparent Km and Kd) and display rapid turnover (apparent kcat). Further, immunization of the autoimmune mice with the analogs of the B-T epitope will direct the promiscuous catalytic activity found in the preimmune state to one specialized to recognize the targeted gp120 epitope (residues 421–436).

Immunization of B10.BR mice (non-autoimmune mice) with the TSAs and CRAAs will overwhelm the suppressor mechanisms that limit catalytic Ab synthesis in the non-autoimmune state. This test is relevant to development of an HIV vaccine, because the goal is to develop vaccines that protect against the infection, regardless of the autoimmune or non-autoimmune status of the host.

The phosphonate ester of the B-T epitope will elicit more potent catalysts than the phosphonate B-T epitope, because the former immunogen will promote clonal expansion of B cells synthesizing Abs containing nucleophilic Ser/Thr residues, which is a feature of the pre-existing catalytic sites encoded by germline VL gene(s). The phosphonate B-T epitope, on the other hand, is designed to recruit Abs that contain an oxyanion hole (such as Asn255 in subtilisin) to stabilize the developing negative charge on the carbonyl oxygen in the transition state. No evidence is available that proves that oxyanion stabilization is responsible for catalysis by the germline encoded catalysts. Note, however, that V region somatic diversification mechanisms (hypermutation, V-J/V-D-J recombination and VL/VH pairing diversity) are powerful mechanisms capable of evolving catalytic sites de novo. Development of Abs that combine the germline nucleophilic site and a somatically developed oxyanion hole is quite feasible. Such nucleophilic, oxyanion stabilizing sites are responsible for efficient catalysis by non-Ab serine proteases. The proposed heterologous immunizations, in which Ab synthesis will be induced by sequential immunization with the phosphonate ester B-T epitope and phosphonate B-T epitope will provoke the synthesis of high turnover, gp120-specific catalysts. The heterologous immunization will also recruit the Ab germline gene(s) encoding nucleophilic sites due to the covalent, electrophilic reactivity of the phosphonate ester, followed by somatic development of an oxyanion stabilizing structure over the course of the immune response.

Comparison of HIV-1 Neutralizing Activity of Anti-gp120 Antibodies Elicited by the Unmodified B-T Epitope with the Neutralizing Activities of Abs Elicited by the Phosphonate B-T Epitope TSA and the Phosphonate Ester B-T Epitope CRAA.

Binding of gp120 to CD4 initiates infection of cells by HIV-1. Cleavage of gp120 in at the 432–433 bond will efficiently block HIV-1 binding by cells, because the cleavage site is located in the CD4 binding region of gp120, and cleavage of this bond by trypsin has previously been shown to inhibit solution phase gp120 binding by CD4 [35].

Abs: Purified IgG samples from mice at various time over the course of the immunization with the control B-T epitope construct (unmodified peptide), the phosphonate B-T epitope (TSA), the phosphonate ester B-T epitope (CRAA), and the combination of the phosphonate and phosphonate ester B-T epitope (TSA+CRAA) will be compared. Hyperimmune IgG from all of these immunizations should be capable of high affinity gp120 binding. The catalytic activity is anticipated to be present in the IgG from the TSA/CRAA immunizations from both mouse strains.

HIV-1 neutralization: Initially, blinded IgG samples from all of the mice at various stages of immunization will be screened in a well-characterized, quantitative, T-cell line assay using a standard laboratory strain (HIV-1 MN). Further studies will be done using hyperimmune IgG obtained towards the end of the immunization schedule. Controls will include cells incubated with IgG without HIV-1 to rule out the possibility of a nonspecific toxic effect of the IgG. These IgG samples will be analyzed using blood-derived PHA-activated lymphocytes as one cell type and blood-derived macrophages as the second cell type. A single dual-tropic primary isolate HIV-1 ADA will be the virus isolate used in the primary cell assay. The reason for using both cell types is to avoid missing any neutralizing/inactivating activity which may reside in a unique epitope specific to the different cell and virus types. It is apparent from earlier work that a number of factors are responsible for the profound differences in the neutralization of laboratory strains from field isolates. Those Ab samples exhibiting neutralizing activity will be directly compared for their potency to both V3 and CD4-inhibiting human monoclonals and well characterized HIV-1 positive human polyclonal sera. In addition, these antibodies will be further evaluated for their stage of, mechanism(s) of action, reversibility as well as their breadth of neutralizing activity over a wide range of antigenic subtypes/clades in multiple primary cell types.

The IgG to be tested will include the noncatalytic anti-gp120 (from non-autoimmune mice immunized with the unmodified B-T epitope) and catalytic anti-gp120 IgG preparations (e.g., from mice immunized with the TSA/CRAAs of the B-T epitope). Because the targeted B epitope in gp120 is essential for CD4 binding, even noncatalytic Abs in IgG preparations of the invention can be anticipated to inhibit HIV-1 neutralization. Assuming that sufficient titers of the Abs are elicited, hyperimmune IgG from each of the experimental groups of mice may inhibit the HIV-1 infectivity.

Homogeneous preparations of catalytic and one noncatalytic Fv constructs will be compared for HIV-1 neutralization activity. This will confirm the results obtained from the polyclonal IgG studies. Further, because the Fv constructs lack the Fc domain, phenomena like complement binding and Fc receptor binding will be eliminated. The absence of enhanced HIV-1 infectivity due to such phenomena will be thus be confirmed using the Fv constructs.

The major attraction of catalytic Abs is their greater and irreversible antigen neutralizing capability compared to non-catalytic Abs. In the present invention, the catalytic IgG samples should display potent HIV-1 neutralization, at concentrations several orders of magnitude lower than the noncatalytic IgG samples. The epitope targeted by the catalyst is a constituent of the CD4 binding site of gp120. Further, cleavage of the targeted bond (Lys432-Ala433) by trypsin has been found to block gp120 binding to CD4. The CD4 binding site tends to be conserved across different strain and subtypes of HIV-1. Thus, the anti-gp120 catalysts of the present invention represent a beneficial therapeutic tool for the treatment of infectious disorders, such as HIV infection.

EXAMPLE III

Use of CRAAs and Catalytic Antibodies in Ischemia-Reperfusion Injury and Septic Shock/SIRS Ischemia-reperfusion injury occurs when blood supply to a tissue is interrupted for a prolonged period (ischemia) and then restored (reperfusion). This type of injury affects both heart attack and stroke patients following treatment to restore blood flow to the damaged tissue. Both ischemia and particularly reperfusion are associated with release into this tissue of certain factors that cause an inflammatory response and injury by inducing programmed cell death.

Septic shock and systemic inflammatory response syndrome (SIRS) are terms for a frequently fatal syndrome that includes hemodynamic changes, inflammation and ultimately the failure of major organs in a predictable order beginning with the lungs. The septic shock syndrome was originally associated only with gram-negative bacterial infections and the effects of endotoxin, but subsequently a variety of other medical problems, such as extensive tissue damage resulting from an accident, were found to initiate the same syndrome, which in the absence of infection is termed SIRS [46]. The multiple organ failure seen in both syndromes is closely associated with and may largely be caused by the occurrence of programmed cell death.

Ischmia-Reperfusion Injury

The four major soluble factors that induce programmed cell death in this disorder are reactive oxygen species (ROS)

and nitric oxide (→peroxynitrite→hydroxyl ROS) which induce and are induced by interleukin-1 beta (IL-1) and tumor necrosis factor alpha (TNF).

Considering the involvement of programmed cell death in ischemia-reperfusion injury and septic shock/SIRS, the fact that the soluble factors just mentioned play a prominent role in both underscores the similarities in pathophysiology between the medical emergencies.

The novel CRAAs of the invention may be used to advantage to develop catalytic antibodies which cleave IL-1 and TNF for the treatment of ischemia-reperfusion injury, septic shock/SIRS and acute respiratory distress syndrome (ARDS) as well as for other inflammatory disorders such as rheumatoid arthritis and for the treatment of neuropathic pain.

Ischemia-Reperfusion Injury

Early return of blood flow to ischemic tissues is critical in halting the progression of cellular injury that results from an interrupted oxygen and nutrient supply. Paradoxically, the reinstitution of blood flow to ischemic tissues is associated with further tissue damage. It has been shown experimentally, for example, that four hours of intestinal ischemia is substantially less damaging than three hours of ischemia plus one hour of reperfusion [47, 48]. The importance of the reperfusion phase to overall tissue damage has been illustrated in numerous studies showing that therapeutic interventions initiated during the ischemic phase are only as effective as those initiated at the onset of reperfusion [49, 50, 51, 52]. Ischemia-reperfusion injured tissues rapidly show zones of necrotic cell death surrounded by areas of cells undergoing programmed cell death [53, 54, 55].

It is well established that ischemic tissues must be exposed to molecular oxygen upon reperfusion to exhibit injury [56–61].

Several mechanisms have been postulated to explain the pathogenesis of ischemia-reperfusion injury but most attention has focused on ROS. ROS refers to any compound derived from molecular oxygen that has a negative charge including superoxide, hydrogen peroxide and the hydroxyl radical which are reduced by one, two and three electrons respectively.

Numerous lines of evidence have implicated ROS in ischemia-reperfusion injury including the following: 1) The production of ROS in ischemic tissues has been detected by electronic spin resonance and spin trapping [62, 63] as well as by nitroblue tetrazolium reduction, chemiluminescence, and salicylate trapping. 2) Exposure of tissues to ROS in the absence of ischemia-reperfusion injury produces pathologic changes similar to ischimia-reperfusion injury itself [64, 65, 66, 67]. 3) Treatment with agents that scavenge ROS or limit ROS production significantly reduce ischemia-reperfusion injury damage [68, 69].

One of the initial effects of ischemia is ATP depletion in the affected tissue, which in turn makes cell membranes permeable to ions, and calcium sequestration inefficent. The resultant increase in cytosolic calcium promotes activation of calcium-dependent phospholipase and proteolytic enzymes, and an important result is the conversion of xanthine dehydrogenase into xanthine oxidase [70]. Xanthine oxidase is found in parenchymal and endothelial cells, and produces ROS superoxide and, directly or indirectly, hydrogen peroxide. That the inhibition of xanthine oxidase reduces the damage caused by ischemia-reperfusion injury supports the notion that ROS production by this enzyme contributes to pathogenesis.

Reduction in phosphatidylethanolamine, breakdown of phospholipids, and liberation of free fatty acids occurs in ischemic tissues. With the onset of reperfusion there is rapid utilization of free fatty acids, particularly arachidonic acid, which stimulates the lipoxygenase and cyclo-oxygenase pathways resulting in the production of ROS. Cyclo-oxygenase inhibitors have been shown to be beneficial in reducing tissue damage due to ischemia-reperfusion injury.

Nitric oxide is a highly reactive species continually released by the endothelium [71]. It maintains the microcirculation in a state of active vasodilation and vascular impermeability and prevents platelet and leukocyte adherence to the endothelium. It is enzymatically synthesized by a consitutively active endothelial synthase from L-arginine and its production can be inhibited by L-arginine analogues such as $N^3$-nitro-L-argine methyl ester (L-NAME). Inhibition of nitric oxide production in the coronary vasculature with inhibitors such as L-NAME can cause myocardial ischemia by vasoconstriction [72]. There is a substantial body of evidence, however, that nitric oxide synthesisinhibitors can substantially reduce the level of tissue damage associated with ischemia-reperfusion injury [73, 74].

Inducible forms of nitric oxide synthase are responsible for increased levels of this molecule during ischemia-reperfusion injury. Inducers include inflammatory cytokines, neuroexcitatory amino acids, and flow-related vasodilation during postischemic hyperthermia. Noiri et al. [75] demonstrated that an antisense oligo targeting transcripts of inducible nitric oxide synthase genes can reduce the expression of these genes. Given systemically, this oligo was taken up by the kidney and significantly reduced renal failure caused by the experimental production of renal ischemia in rats.

Nitric oxide can combine with the superoxide anion to produce the toxic free-radical peroxynitrite, leading to the production of the hydroxyl radical, a ROS thought to be a major causal factor in ischemia-reperfusion injury [74]. Reduction of molecular oxygen to produce superoxide occurs in all aerobically respiring cells in the mitochondria transport system.

Nitric oxide has also been shown to induce programmed cell death in a number of physiologic and experimental situations. Activation of high-level nitric oxide production helps form the first line of defence against invading pathogens and tumor cells.

Release of ROS in areas of ischemia-reperfusion injury attracts inflammatory leukocytes, which in turn can cause tissue injury by means of a cytotoxic arsenal that includes the release of additional ROS. Numerous studies have shown: 1) that leukocytes accumulate in areas of ischemia-reperfusion injury, and 2) that depletion of circulating neutrophils or use of agents that prevent neutrophil activation can sometimes reduce tissue damage associated with ischemia-reperfusion injury.

The terminal phases of programmed cell death involve a set of enzymes belonging to the ICE family. Peptides capable of inhibiting some of these enzymes have been shown to reduce ischemic brain damage resulting from transient middle cerebral artery occlusion in rodents and significantly improve resulting behavioral deficits [76]. The latter observation demonstrates that functional recovery of ischemic neural tissue can follow treatments that prevent the cell death program from going on to completion. Presumably, the degree of functional recovery would be even greater in instances where ischemia is followed by reperfusion injury.

Numerous studies have demonstrated that programmed cell death is a ubiquitous feature of tissue damaged by ischemia-reperfusion injury [53, 54, 55].

Induction of inducible nitric oxide synthase levels has been positively correlated with programmed cell death in rat hearts by Szabolcs et al. [77]. Cardiac tissue was transplanted from Lewis to Wistar-Furth rats as a model of cardiac allograft rejection, while Lewis to Lewis transplants served as a control. The number of cardiac myocytes undergoing programmed cell death increased sharply from day 3 to day 5 following transplantation. At day 5, allografts showed a significantly greater increase in the myocytes, endothelium and macrophages undergoing programmed cell death when compared to syngenic grafts. Expression of inducible nitric oxide synthase mRNA, protein and enzymatic activity was shown to increase in parallel in time and extent with programmed cell death in the cardiac myocytes. Immunohistochemical staining demonstrated that areas of increased inducible nitric oxide also expressed nitrotyrosine, indicative of peroxynitrite formation.

Numerous lines of evidence support the conclusion that interleukin-1 beta (IL-1) and tumor necrosis factor alpha (TNF) play important roles in the evolution of ischemia-reperfusion injury.

The production of both proinflammatory cytokines has been shown to be associated with cell activation of the monocyte/macrophage series, which can occur as the result of xanthine-oxidase-derived oxygen radical activity.

IL-1 was discovered in the 1940s and was initially shown to produce fever when injected into animals. In the early 1970s, IL-1 was found to have a variety of other biological effects when injected into animals including neutrophilia, heightened antimicrobial responses, increased synthesis of hepatic acute phase reactants, and induction of colony stimulating factors. It was also found to boost T-cell response to mitogens in culture and to function as an adjuvant.

Cloning studies have demonstrated that IL-1 is a three-member family consisting of IL-1 alpha, IL-1 beta and IL-1ra. The first two are agonists and the last a receptor antagonist. IL-1 alpha is localized on cell membranes while IL-1 beta is released as a cytokine and is the form simply referred to in this text. It is synthesized as a precursor that must be cleaved before it can become active. The most specific of these enzymes is interleukin-1beta-converting enzyme (ICE) which is closely related to the family of enzymes active in the final phases of programmed cell death.

IL-1 expression has been demonstrated in areas subjected to ischemia-reperfusion injury in the retina, liver, skeletal muscle and intestine. Both IL-1 and TNF expression were similarly demonstrated in the brain and heart. In the rodent model used by Hara et al. [76], IL-1 expression reached its peak 30–60 minutes after reversal of experimental occlusion of the middle cerebral artery and decreased thereafter.

Treatment of rat cardiac myocytes with IL-1 induces nitric oxide synthase transcription and increased expression of the enzyme by a protein kinase A-dependent pathway. IL-1 was also shown to induce this enzyme in brain endothelial cells. Similarly IL-1 and TNF were shown to induce heart and hepatic nitric oxide synthase. As discussed above, ROS cause genomic damage that induces p53 expression which can result in programmed cell death.

IL-1 also induces the expression of other proinflammatory cytokines such as IL-6. In some instances induction is mediated by the transcription factor NF-KB which can also mediate the effects of TNF. The frequently observed synergy between IL-1 and TNF as well as IL-1 and IL-6 may be explained in part on the basis of significantly overlapping signal transduction pathways in cell populations responsive to all three cytokines.

IL-1ra treatment of rats undergoing hepatic ischemia-reperfusion injury has been found to reduce TNF production, tissue injury and mortality [78]. Ischemia was induced in rat livers by clamping the vessels of the left and middle lobes for 90 minutes. In one set of experiments, IL-1ra was given systemically five minutes before ischemia was induced, and TNF levels were determined in the blood and liver at various time points after reperfusion had begun. In control animals, TNF levels in both tissues were found to increase over time as the reperfusion continued, with the experiment being terminated 4½ hours from the initiation of ischemia. In contrast, IL-1ra treatment caused a decrease in TNF levels in the two tissues. Histologic examination demonstrated that IL-1ra treatment was associated with substantially less liver damage compared to controls.

In a second set of experiments, the unaffected right lateral and caudate lobes of the liver were removed after the period of ischemia was completed. Eighty percent of control animals died compared to 30% of those treated with IL-1ra.

In similar studies, it was demonstrated that IL-1ra treatment and naturally occuring IL-1ra protect rat brain tissue from ischemia-reperfusion injury-induced damage.

The role of TNF in ischemia-reperfusion injury of the brain was examined. In one set of experiments, variable doses of TNF were administered intracerebroventricularly to rats 24 hours before occluding the middle cerebral artery for 80 or 160 minutes (transient) or until termination of the experiment 24 hours later (permanent). In some groups TNF neutralizing antibody was given 30 minutes before the TNF injection. Administration of exogenous TNF produced a significant dose-dependent increase (32%) in the infact size caused by permanent occlusion. The high dose of TNF (25 pmol) caused an increase in the infact size in both transient occlusion groups of 100% and 34% respectively. All of these effects of exogenous TNF were abrogated in the animal that received pretreatment with the TNF antibody.

In yet another set of experiments, the effects of blocking endogenous TNF was evaluated by blocking TNF function with either a neutralizing antibody or a soluble TNF receptor (sTNF-RI) given 30 minutes before or 3 or 6 hours after permanent occlusion. Blocking TNF function before or after occlusion resulted in an up to 26% reduction in infact size depending on the inhibitor dose.

TNF has been shown to partially mediate liver damage associated with the reperfusion phase of ischemia-reperfusion injury. Hepatic TNF production was responsible for neutrophil sequestration and activation in the affected area, leading to the release of ROS. Passive immunization with neutralizing TNF antibodies could significantly inhibit these pathogenic effects. It has also been shown that TNF administered to cultured hepatocytes enhances the cytotoxicity of ROS given at the same time. Similarly, neutralizing TNF antibodies were shown to reduce cardiovascular effects and improve survival rate after acute ischemia-reperfusion injury was induced by a 45-minute occlusion of the superior mesenteric artery in a rat model.

Septic Shock/SIRS

Leaving etiology aside, the basic pathophysiologic events that occur in ischemia-reperfusion injury and septic shock/SIRS are very similar, but in the former the pathology is localized while in the latter it is systemic and can terminate in multiple organ failure beginning with the lungs. Key elements in both groups of disorders are ROS, nitric oxide, IL-1, TNF, and programmed cell death.

Most of the experimental studies in this field involve septic shock because of the ease with which the syndrome can be induced using bacteria or bacterial products. The pathophysiologic changes uncovered in these studies associated with septic shock/SIRS in patients demonstrate that the syndrome is driven by a cascade of proinflammatory mediators. It is generally agreed that this cascade is initiated by IL-1 and TNF which are initially released from macrophages and other inflammatory cells. IL-1 is also produced by a wide variety of other cell types and most of the cells in the body have receptors for IL-1. IL-1 production has been shown to be stimulated by ROS and TNF and both of these cytokines promote ROS production. In septic shock, IL-1 and TNF production results from the action of endotoxin and other bacteria products. The high expression of these two factors along with ROS leads to the excessive production of a wide variety of secondary mediators including IL-6, IL-8, gamma-interferon, prostaglandin $I_2$, thromboxane $A_2$, prostaglandin $E_2$, transforming growth factor beta, platelet activating factor, bradykinin, angiotensin, and vasoactive intestinal peptide. These factors contribute to the pathological cardiovascular, hemodynamic and coagulation and other changes associated with this syndrome.

TNF was the first cytokine to be linked to the septic shock/SIR syndrome, when it was demonstrated that its overproduction is an antecedent to shock and death. Soon after IL-1 was shown to be similarly toxic and was synergistic when given with TNF. As a result otherwise nonlethal amounts of TNF and IL-1 when combined, produced lethal shock in animals.

Following an inflammatory insult, TNF is the first cytokine to appear in the circulation followed by IL-1. In volunteers injected with endotoxin, for example, TNF levels peak 60–90 minutes after the insult and return to baseline within three hours. IL-1 levels plateau 3–4 hours after treatment. These general observations and the finding that TNF can induce IL-1 production have contributed to the notion that TNF is the initial cytokine that begins the septic shock/SIR syndrome whereas IL-1 is more involved with its continuation.

Measurement of serum IL-6 levels, which is induced by both TNF and IL-1, has been suggested as a better measure of TNF and IL-1 production than a direct measurement of these cytokines. IL-6 levels in the circulation often directly correlate with the severity of disease in patients with trauma, sepsis and septic shock/SIRS. Unlike IL-1 and TNF, however, IL-6 administration does not induce inflammation or septic shock/SIRS and inhibitors of IL-6 do not prevent the lethal effects of this syndrome.

A large body of additional evidence supports the notion these mediators play a critical role in the pathogenesis of this syndrome. Casey et al. [77], for example, examined the correlation between the various factors involved in septic shock and the outcome for 97 patients, 57 of which either had full blown septic shock or were hypotensive which is an early indicator of impending septic shock/SIRS. The survival rate for this group of patients was 54%. The strongest positive correlation was between plasma IL-6 levels and mortality and the second strongest was with the IL-1 levels. IL-1 is usually undetectable in normal subjects (<40 pg/ml). There was no correlation between TNF, and endotoxin levels and death. The lack of correlation with TNF was ascribed to the fact this cytokine is only produced in the earliest stages of the factor cascade and it has a short half-life. Elevated TNF levels, however, did correlate with the presence of gram positive sepsis.

The proinflammatory cytokines involved in septic shock/SIRS, particulary TNF, activate the coagulation and complement cascades which causes neutrophil activation with the release of ROS. Nitric oxide synthase is induced by IL-1 and TNF in both endothelial cells and inflammatory cells. Activated neutrophils consume oxygen in the so called respiratory burst forming the super oxide ion that reacts with nitric oxide to from peroxynitrite that decomposes to from the hightly toxic hydroxyl ROS. ROS, especially superoxide, generate chemotactic factors when they react with a plasma precursor in a self-amplifying process.

Patients with septic shock/SIRS have responded favorably to treatment with anti-oxidants confirming the importance of ROS in the pathogenesis of this syndrome. A marked reduction in mortality rate, for example, has been seen in patents with the sepsis-related acute respiratory distress syndrome (ARDS) following treatment with a four anti-oxidant combination treatment. ARDS refers to the lung-failure related pathophysiology that is the first of the multiple organ failures that characterisze the terminal phase of septic shock/SIRS. Similarly, in another study patients with ARDS given the antioxidant n-acetyl cysteine showed improved lung and cardiac function including changes in pulmonary vascular resistance, cardiac output and oxygen delivery.

The mechanistic understanding of septic shock/SIRS that has developed based on these and a large body of additional data strongly suggests that this syndrome could be prevented by agents that block TNF and IL-1 production. IL-1 neutralizing antibodies have been shown to ameliorate the septic shock syndrome in animal models. Recombinant IL-1ra administration, however, has been the most frequently used approach for blocking IL-1 function in animal models of septic shock/SIRS [78].

Simultaneous treatment of rabbits, for example, with adequate amounts of IL-1ra followed by normally lethal quantities of endotoxin result in only mild and transient hypotension and decreased neutrophil infiltration into tissues. IL-1ra has also been demonstrated to prevent the death of rats infected with *K. pneumoniae* and from *E. coli* peritonitis.

The ability of IL-1ra infusion to attenuate subsequent lethal *E. coli* septic shock in baboons has been studied. When given in excess in the range of $10^3$ to $10^4$ fold with respect to IL-1 levels, IL-1ra prevented a sustained IL-1 response, although no effect on the initial production of the cytokine was seen, resulting in a 100% survival rate at 24 hours vs. 43% in placebo treated controls.

Many reports have provided evidence that TNF neutralizing antibodies and soluble TNF receptors can protect animals from otherwise lethal injections of bacterial toxins, such as endotoxin, that can induce septic shock. To be beneficial, however, these treatments have to be given before or during the infusion of endotoxin or bacteria.

The role of TNF in the initiation of septic shock has also been investigated using TNF-1 receptor knockout mice. These mice were shown to not respond to doses of TNF that produces a lethal septic shock syndrome in normal mice. The knockouts also did not respond to normally lethal doses of endoxin if they were pretreated with D-galactosamine and agent that sensitizes animals to the toxin by blocking its metabolism by the liver. There were no differences between the normal mice and the knockouts in terms of the plasma levels of TNF induced by endotoxin. Following a sublethal challenge with endotoxin, the levels of IL-6 released in to the circulation were found to be dramatically less in the knockout mice compared to controls. Finally, macrophages from knockout mice have been shown to be severely limited in their capacity to produce nitric oxide by the inducible nitric oxide synthase pathway. In contrast, mice with an IL-6 deletion showed no such deficit.

As many as six TNF antagonists under development by five different companies for the treatment of septic shock have been in Phase II–III clinical trials at one time. Four of these inhibitors were neutralizing antibodies and two were soluble recombinant TNF receptors. None of these products has has distinguished itself as a viable treatment for this syndrome. TNF antagonists including neutralizing antibodies, however, are not intrinsically without efficacy in patients because they have subsequently shown substantial promise in clinical trials for the treatment of rheumtoid arthritis.

Clearly, attempts over the last ten years to develop new treatments for septic shock/SIRS have resulted in many disappointments. Pruitt et al. [78] have summarized a number of the reasons put forth by numerous investigators for why the cytokine inhibitor trials have failed. Perhaps the single greatest obstacle to success relates to the cost of the existing cytokine inhibitors. Their high price precludes them from being used prophylactically. For example, as pointed out by Pruitt et al. [78], to sustain a therapeutic plasma concentration of 10–15 micrograms/ml, IL-1ra has to be given at concentrations of 1.5–2.0 mg/kg/hr of about 2.5 grams per day for as long as the patient is septic.

Consequently, patients who receive IL-1 or TNF inhibitors are already symptomatic. Yet our understanding of the pathogenesis of this syndrome strongly suggests that IL-1 and particularly TNF function must be blocked at the very initiation of the cascade of excessive proinflammatory cytokine release that has a major role in driving the syndrome forward. Again, animal studies have convincingly shown that to be effective IL-1 and TNF must be given prior to or simultaneously with the inflammatory insult that engenders the septic shock/SIR syndrome.

In the Synergen Inc. Phase II trial, for example, IL-1ra was given 9 hours on average after a patient was judged a suitable candidate for study [79]. As a result, numerous patients entered into the trial had developed a septic response 24 or more hours before the initiation of the IL-1ra infusion. Thus for many patients the proinflammatory cascade is well advanced by the time the attempt to block IL-1 function was begun.

Positive responses in the IL-1ra clinical trials may have also been obscured by the use of the 28 day all-cause mortality criterion. A re-evaluation of the Phase II and first Phase III trial data reveals that the major benefits obtained from the IL-1ra infusion occurred 3–7 days after treatment [78]. Survival curves were subsequently essentially parallel. This finding could reflect the very short half-life of IL-1ra. The beta-phase half-life of IL-1ra in septic primates, for example, is approximately 21 minutes. Similarly, the half-lives of IL-1 and TNF are measured in minutes to hours. It is not surprising, therefore, that mortality after the first week following IL-1ra infusion is irrelevant to assessing the value of the therapy.

Yet another problem with the IL-1ra clinical trials, which is generally applicable to systemically administered inhibitors of IL-1 or TNF, comes from the practice of determining the dose of the cytokine inhibitor based on the plasma concentration of the cytokine. The reason is that local tissue concentration of these cytokines can be much higher than what is present in plasma. In patients with ARDS, for example, IL-1 concentrations in the lungs have been shown to be as high as 15 ng/ml while the plasma concentrations are under 100 pg/ml.

Thus the septic shock/SIRS data and current understanding of the syndrome supports the development of novel therapies which can (1) block IL-1 and TNF and be sufficiently inexpensive to be given prophylactically to at risk patients; and (2) prevent the programmed cell death that is a major contributing factor to the organ failure that causes the many deaths associated with this syndrome.

Figure 15:
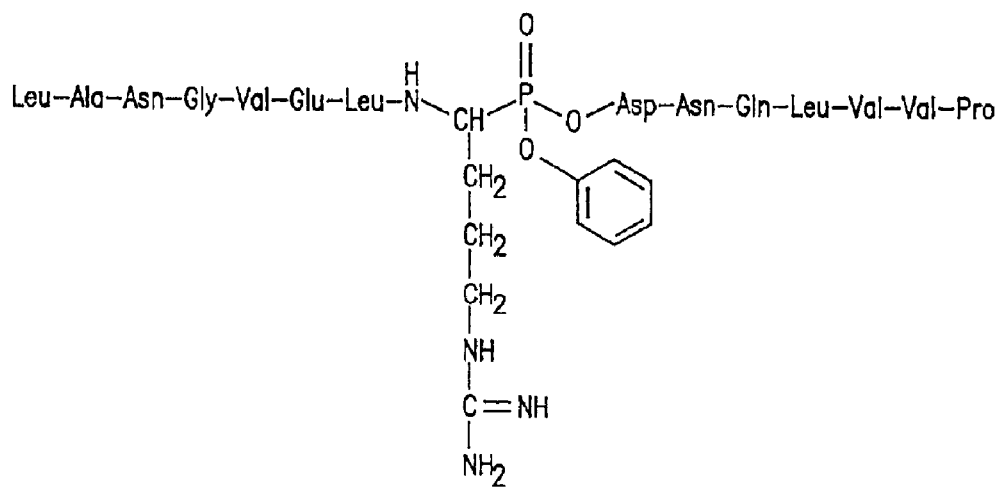
FIG. 15 is an exemplary CRAA designed to elicit catalytic antibodies to TNFα.
Figure 16:
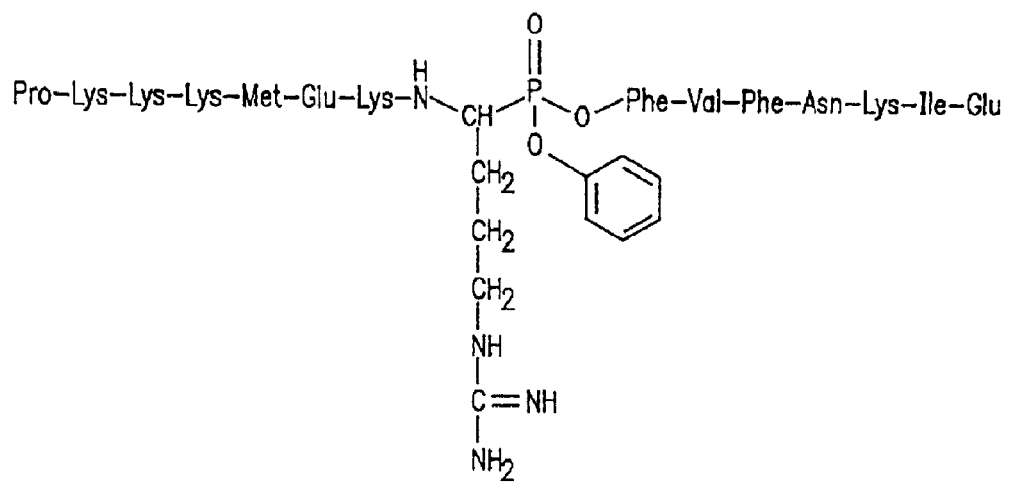
FIG. 16 is an exemplary CRAA designed to elicit catalytic antibodies to IL-1β.
Figure 17:
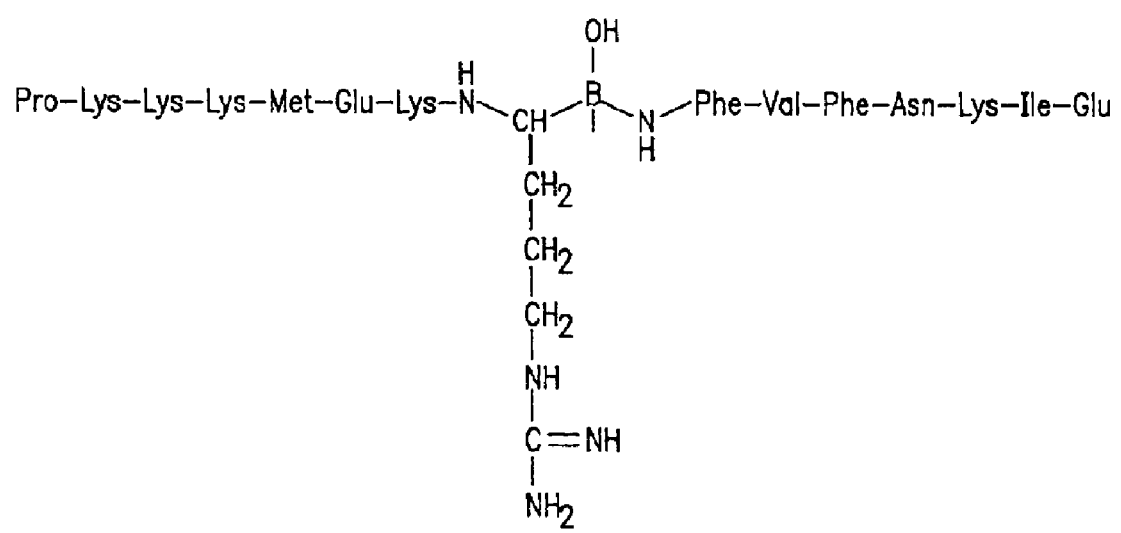
FIG. 17 is an exemplary CRAA designed to elicit catalytic antibodies to IL1-β. In this CRAA the electrophillic reaction center comprises a boronate molecule.

Accordingly, CRAAs are described herein which will stimulate the immune production of catalytic antibodies specfic for TNF and IL-1. These antibodies may be administered using protocols already developed for immunotherapies based on the administration of other known monoclonal antibodies. As the antibodies of the present invention act catalytically, the dosage will be much lower than antibodies with bind reversibly and stoichiometrically. Accordingly, the cost of prophylactic treatment for patients at risk for the syndrome will be greatly reduced. An exemplary CRAA for eliciting catalytic antibodies to TNFA is shown in FIG. 15. Exemplary CRAAs for eliciting catalytic antibodies to IL1β are shown in FIGS. 16 and 17. A boronate electrophillic center is shown in FIG. 17.

EXAMPLE IV

Passive Immunization with the Catalytic Antibodies of the Present Invention

There are many areas in medicine where monoclonal antibody administration is providing clinical benefit. In the field of organ transplantation, a MoAb (OKT3) which binds to the T cell receptor has been employed to deplete T cells in vivo. Additionally, MoAbs are being used to treate graft v. host disease with some success. A clinical trial has been established which is assessing the ability of anti-CD4 moAB to deplete a subset of T cells in the treatment of multiple schlerosis.

Accordingly, methods of administration of monoclonal antibodies are well known to clinicians of ordinary skill in the art. An exemplary method and dosage schedule are provided in a phase III, randomized, controlled study of chemotherapy alone or in combination with a recombinant moAB to the oncogene HER2.

All patients randomized to the recombinant humanized MoAb Her2 arm of the study will receive treatment as a 4 mg/kg I.V. loading dose on Day 0 (the first day of the MoAb HER2 infusion, or the day of randomization for patients in the control group), then weekly as a dose of 2 mg/kg I.V. through out the course of the study. All patients will be monitored during each study visit by a clinical assessment, a symptom directed physical examination (if appropriate) and laboratory tests. Routine tumor evaluations will be conducted for all patients at prescribed intervals during the study. All adverse events will be recorded.

The administration of the catalytic antibodies of the present invention will be done as described above for the HER2 monoclonal antibody. As in the HER2 study, following infusion, patients will be assessed to determine the efficacy of the administered catalytic antibody.

Should the catalytic antibodies administered as above give rise to undesirable side effects in the patient, the immunizing CRAAs will be administered to covalently inhibit the action of the catalytic antibodies.

EXAMPLE V

Active Immunization Using the CRAAS of the Present Invention

Active immunization will be done using previously developed methods with vaccines designed to elicit protective antibody responses against the desired antigens [82, 83]. For example, the CRAAs mixed with a suitable adjuvant formulation such as alum can be admimistered intramuscularly at a dose optimized for maximum antibody synthesis (100–1000 μg/kg body weight), and two or three booster injectijns can be administed at 4 week intervals, until the catalytic antibody concentration in the serum reaches plateau levels. The protective immunity so generated is anticipated to last for several years, because vaccination will result in formation of specific, long lived memory cells that can be stimulated to produce antibodies upon exposure to the offending organism or cancer cell. Descriptions and methods to determine the catalytic antibody concentrations are set forth in Examples I and II. Because antibody synthetic response to most antigens are T cell dependent, an appropriate T cell epitope can be incorporated into the immunogen by peptide synthesis, as described in the case of the gp120, Example II. Alternatively, a carrier such as keyhole limpet hemocyanin can be conjugated to the CRAA via coupling through lys side chain amino groups or Cys side chain sulfahydryl groups to maximize the antibody response if necessary.

References

1. Paul, S., Volle, D. J., Beach, C. M., Johnson, D. R., Powell, M. J. and Massey, R. J. Catalytic hydrolysis of vasoactive intestinal peptide by human autoantibody. *Science* 244:1158–1162, 1989.
2. Paul, S., Sun, M., Mody, R., Eklund, S. H., Beach, C. M., Massey, R. J. and Hamel, F. Cleavage of vasoactive intestinal peptide at multiple sites by autoantibodies. *J. Biol. Chem.* 256:16128–16134, 1991.
3. Suzuki, H., Imanishi, H., Nakai, T. and Konishi, Y. K. Human autoantibodies that catalyze the hydrolysis of vasoactive intestinal polypeptide. *Biochem. (Life Sci. Adv.)* 11:173–177, 1992.
4. Li, L., Kaveri, S., Tyutyulkova, S., Kazatchkine, M. and Paul, S. Catalytic activity of anti-thyroglobulin antibodies. *J. Immunol.* 154:3328–3332, 1995.
5. Shuster, A. M., Gololobov, G. V., Kvashuk, O. A., Bogomolova, A. E., Smirnov, I. V. and Gabibov, A. G. DNA hydrolyzing autoantibodies. *Science* 256:665–667, 1992.
6. Gololobov, G. V., Chernova, E. A., Schourov, D. V., Smirnov, I. V., Kudelina, I. A. and Gabibov, A. G. Cleavage of supercoiled plasmid DNA by autoantibody Fab fragment: Application of the flow linear dichroism technique. *Proc. Natl. Acad. Sci. USA* 92:254–257, 1995.
7. Tawfik, D., Chap, R., Green, B., Sela, M. and Eshhar, Z. Unexpectedly high occurrence of catalytic antibodies in MRL/lpr and SJL mice immunized with a transition state analog. Is there a linkage to autoimmunity? *Proc. Natl. Acad. Sci. USA* 92:2145–2149, 1995.
8. Davies, D. R. and Chacko, S. Antibody Structure. *Acc. Chem. Res.* 26:421–427, 1993.
9. Sun, M., Gao, Q-S., Li, L. and Paul, S. Proteolytic activity of an antibody light chain. *J. Iminunol.* 153:5121–5126, 1994.
10. Gao, Q-S., Sun, M., Tyutyulkova, S., Webster, D., Rees, A., Tramontano, A., Massey, R. and Paul, S. Molecular cloning of a proteolytic antibody light chain. J. Biol. Chem. 269:32389–32393, 1994.
11. Titmas, R. C., Angeles, T. S., Sugasawara, R., Aman, N., Darsley, M. J., Blackburn, G. and Martin, M. T. Aspects of antibody-catalyzed primary amide hydrolysis. *Appl. Biochem. Biotechnol.* 47:277–290, 1994.
12. Gao, Q.-S., Sun, M., Rees, A. and Paul, S. Site-directed mutagenesis of proteolytic antibody light chain. J. Mol. Biol. 253:658–664, 1995.
13. Lerner, R. A., Benkovic, S. J. and Schultz, P. G. At the crossroads of chemistry and immunology: Catalytic antibodies. *Science* 252:659–667, 1991.
14. Tyulkova, S., Gao, Q-S., Thompson, A., Rennard, A. and Paul, S. light chains selected from an asthma patient by phage display. *Biochem. Biophys. Acta.* 1316:217–223, 1996.
15. Batra, S. K., Rasheed, A., Bigner, S. H. and Bigner, D. D. Oncogenes and anti-oncogenes in human central nervous system tumors. *Lab. Invest.* 71:621–637, 1994.
16. Modjtahei, H., Ecc les, S. A., Box, G., Styles, J. and Dean, J. Antitumor activity of combinations of antibodies directed against different epitopes on the extracellular domain of the human EGF receptor. *Cell Biophys.* 22:129–146, 1993.
17. Modjtahedi, H., Eccles, S., Sandle, J., Box, G., Titley, J. and Dean, C. Differentiation or immune destruction: two pathways for therapy of squamous cell carcinomas with antibodies to the epidermal growth factor receptor. *Cancer Res.* 54:1695–1701, 1994.
18. Wikstrand, C. J., Hale, L. P., Batra, S. K., Hill, M. L., Humphrey, P. A., Kurpad, S. N., McLendon, R. E., Moscatello, D., Pegram, C. N., Reist, C. J., Traweek, S. T., Wong, A. J., Zalutsky, M. R. and Bigner, D. D. Monoclonal antibodies against EGFRvIII are tumor specific and react with breast and lung carcinomas and malignant gliomas. *Cancer Res.* 55:3140–3148, 1995.
19. Faillot, T., Magdelenat, H., Mady, E., Stasiecki, P., Fohanno, D., Gropp, P., Poisson, M. and Delattre, J. Y. A phase I study of an anti-epidermal growth factor receptor monoclonal antibody for the treatment of malignant gliomas. *Neurosurgery* 39:478–83, 1996.
20. Stragliotto, G., Vega, F., Stasiecki, P., Gropp, P., Poisson, M. and Delattre, J. Y. Multiple infusions of anti-epidermal growth factor receptor (EGFR) monoclonal antibody (EMD 55,900) in patients with recurrent malignant gliomas. *Eur. J. Cancer* 32A:636–40, 1996.
21. Nagane, M., Coufal, F., Lin, H., Bogler, O., Cavenee, W. K. and Huang, H. H. A common mutant epidermal growth factor receptor confers enhanced tumorigenicity on human glioblastoma cells by increasing proliferation and reducing apoptosis. *Cancer Res.* 56:5079–5086, 1996.
22. Brown, P. M., Debanne, M. T., Grothe, S., Bergsma, D., Caron, M., Kay, C. and O'Connor-McCourt, M. D. The extracellular domain of the epidermal growth factor receptor. Studies on the affinity and stoichiometry of binding, receptor dimerization and a binding-domain mutant. *Eur. J. Biochem.* 225:223–233, 1994.
23. Sampson, N. S. and Barton, P. A. Peptidic Phophonylating agents as irreversible inhibitors of serine proteases and models of the tetrahedral intermediates. *Biochemistry* 30:22255–2263, 1991.
24. Baylis, E. K., Campbell, C. D., and Dingwall, J. G. 1-aminoalkylphoshonous acids. Part 1. Isosteres of the protein amino acids *J. Chem. Soc. Perkin Trans.* Part I: 2845–2853, 1984
25. Tyutyulkova, S., Gao, Q-S. and Paul, S. Selection of human immunoglobulin light chains from a phage display library. *Antibody Engineering Protocols.* Ed., Paul S. (Methods in Molecular Biology Series, Humana Press, Totowa, N.J.) 51:377–394,1995.
26. Clackson, T., Hoogenboom, H. R., Griffiths, A. D. and Winter, G. Making antibody fragments using phage display libraries. *Nature* 352:624–628, 1991.
27. McAfferty, J., Fitzgerald, K. J., Earnshaw, J., Chiswell, J., Chiswell, D. J., Link, J., Smith, R. Kenten, J. Selection and rapid purification of murine antibody fragments that bind a transition state analog yb phage display. Appl. Biochem. Biotechnol. 47:157–174, 1994.
28. Sun, M., Mody, B., Eklund, S. H. and Paul, S. VIP hydrolysis by antibody light chains. *J. Biol. Chem.* 266:15571–15574, 1991.

29. Bone, R., Sampson, N. S., Bartlett, P. A. and Agard, D. A. Crystal structures of a-lytic proteaase complexes with irreversibly bound phophonate esters. *Biochemistry* 30:2263–2272, 1991.
30. Lax, I., Fischer, R., Ng, C., Segre, J., Ullrich, A., Givol, D. and Schlessinger, J. Noncontiguous regions in the extracellular domain of EGF receptor define ligand-binding specificity. *Cell Regul.* 2:337–345, 1991.
31. Moore, J. and Trkola, A. HIV type 1 coreceptors, neutralization serotypes, and vaccine development. *AIDS Res. Hum. Retroviruses* 13:733–736, 1997
32. Thali, M., Furman, C., Ho, D., Robinson, J., Tilley, S., Pinter, A. and Sodroski, J. Discontinuous, conserved neutralization epitopes overlapping the CD4-binding region of human immunodeficiency virus type 1 gp120 envelope glycoprotein. *J. Virol.* 66:5635–5641, 1992.
33. Wang, W-K., Essex, M. and Lee, T-H. The highly conserved aspartic acid residue between hypervariable regions 1 and 2 of human immunodeficiency virus type 1 gp120 is important for early stages of virus replication. *J. Virol.* 69:538–542, 1995.
34. Ivanoff, L. A., Dubay, J. W., Morris, J. F., Roberts, S. J., Gutshall, L., Sternberg, E. J., Hunter, E., Matthews, T. J. and Petteway, S. R. J. V3 loop region of the HIV-1 gp120 envelope protein is essential for virus infectivity. *Virology* 187:423–432, 1992.
35. Pollard, S., Meier, W., Chow, P., Rosa, J. and Wiley, D. CD4-binding regions of human immunodeficiency virus envelope glycoprotein gp120 defined by proteolytic digestion. *Proc. Natl. Acad. Sci. USA* 88:11320–11324, 1991.
36. Kalaga, R., Li, L., O'Dell, J. and Paul, S. Unexpected presence of polyreactive catalytic antibodies in IgG from unimmunized donors and decreased levels in rheumatoid arthritis. *J. Immunol.* 155:2695–2702, 1995.
37. Watanabe-Fukunaga, R., Brannan, C. I., Copeland, N. G., Jenkins, N. A. and Nagata, S., Lymphoproliferation disorder in mice explained by defects in Fas antigen that mediates apoptosis. *Nature* 356:314–317, 1992.
38. Tramontano, A., Janda, K. D. and Lerner, R. A. Chemical reactivity at an antibody binding site elicited by mechanistic design of a synthetic antigen. *Proc. Natl. Acad. Sci. USA* 83:6736–6740, 1986.
39. Bermas, B. L., Petri, M., Berzofsky, J. A., Waisman, A., Shearer, G. M. and Mozes, E. Binding of glycoproteinl20 and peptides from the HIV-1 envelope by autoantibodies in mice with experimentally induced systemic lupus erythematosus and in patients with the disease. *AIDS Res. Hum. Retrovir.* 10:1071–1077, 1994.
40. Paul, S., Li, L., Kalaga, R., Wilkins-Stevens, P., Stevens, F. J. and Solomon, A. Natural catalytic antibodies: Peptide hydrolyzing activities of Bence Jones proteins and $V_L$ fragment. *J. Biol. Chem.* 270:15257–15261, 1995.
41. Pollack, S. J., Hsiun, P. and Schultz, P. G. Sterospecific hydrolysis of alkyl esters by antibodies. *J. Am. Chem. Soc.* 111:5962–5964, 1989.
42. Ahlers, J. D., Pendleton, C. D., Dunlop, N., Minassian, A., Nara, P. L. and Berzofsky, J. A. Construction of an HIV-1 peptide vaccine containing a multideterminant helper peptide linked to a V3 loop peptide 18 inducing strong neutralizing antibody responses in mice of multiple MHC haplotypes after two immunizations. *J. Immunol.* 150:5647–5665, 1993.
43. Panina-Bordignon, P., Tan, A., Termijtelen, A., Demotz, S., Corradin, G. and Lanzavecchia, A. Universally immunogenic T cell epitopes: promiscuous binding to human MHC class II and promiscuous recognition by T cells. *Eur. J. Immunol.* 19:2237–2242, 1989.
44. Ahlers, J. D., Dunlop, N. Alling, D. W., Nara, P. L. and Berzofsky, J. A. Cytokine-in-adjuvant steering of the immune response phenotype to HIV-1 vaccine constructs. *J. Immunol.* 158:3947–3958, 1997.
45. Sattentau, Q. J. and Moore, J. P. Human Immunodeficiency Virus Type 1 Neutralization Is Determined by Epitope Exposure on the gp120 Oligomer. *J. Exp. Med.* 182:185–196, 1995.
46. Bone R., Balk R., Cerr F (1992). Definitions for sepsis and organ failure and guidelines for the use of innovative therapies in sepsis. The ACCP/SCCM consensus conference committee. American college of chest physicians/society of critical care medicine. *Crit Care Med* 20, 864–874.
47. Parks D & Granger D. (1986a). Contributions of ischemia and reperfusion to mucosal lesion formation. *Am J Physiol* 250, G749–G753.
48. Parks D. & Granger D. (1986b). Xanthine oxidase: biochemistry, distribution, and physiology. *Acta Physiol Scand* 548, 87–100.
49. Carden D., Smith J. & Korthuis R. (1990). Neutrophil-mediated microvascular dysfunction in postischemic canine skeletal muscle: role of granulocyte adherence. *Circ Res* 66, 1436–1444.
50. Grisham M. Hernandex L. & Granger D., (1989). Adenosine inhibits ischemia-reperfusion induced leukocyte adherence and extravasation. *Am J Physiol* 257, H1334–H1339.
51. Jerome S., Smith C. & Korthuis R. (1993). CD18dependent adherence reactions play an important role in the development of the no-reflow phenomenon. *Am J Physiol* 263, H1637–H1642.
52. Morris J., Haglund U. & Bulkley G. (1987). The protection from postischemic injury by xanthine oxidase inhibition: blockade of free radical generation or purine salvage. *Gastroen*, 92 1542–1547.
53. Charriaut-Marlangue E., Margaill I., Represa A., Popovici T., Plotkine M. & Ben-Ari (1996). Apoptosis and necrosis after reversible focal ischemia: an in situ DNA fragmentation analysis. *J Cereb Blood Flow Metab* 16:186, 33–41.
54. Johnson E., Greenlund L., Akins P. & Hsu C. (1995). Neuronal apoptosis: current understanding of moleular mechanisms and potential role in ischemia brain injury. *J Neurotrauma* 12, 843–852.
55. Li Y., Chopp M., Jiang N., Yao F. & Zaloga E. (1995) Temporal profile of in situ DNA fragmentation after transient middle cerebral artery occlusion in the rat. *Cereb Blood Flow Metab* 15, 389–397.
56. Hearse D. (1977). Reperfusion of ischemic myocardium. *J Mol Cell Cardio* 9, 605–615.
57. Hearse D., Humphrey R. & Chain E. (1973). Abrupt reoxygenation of the anoxic potassium arrested rat heart: a study of myocardial enzyme release. *J Mol Cell Cardio* 5, 395–407.
58. Korthuis R., Smith J. & Carden D. (1989). Hypoxic reperfusion attneuates postischemic microvascular injury. *Am J Physio* 256, H315–H319.
59. Perry M. & Wadhaw S. (1988). Gradual reintroduction of oxygen reduces reperfusion injury in cat stomach. *Am J Physiol* 254, 366–372.
60. Walker P., Lindsay T., Labbe R., Mickle D. & Romaschine A. (1987). Salvage of skeletal muscle with free radical scavengers. *J Vasc Surg* 6, 68–75.
61. Wright J., Fox D., Kerr J., Valeri C. & Hobson R. (1988). Rate of reperfusion blood flow modulates reperfusion injury in skeletal muscle. *J Surg Res* 44, 754–759.

62. Bolli F., Jeroudi M., Patel B., DuBose C., Lai E. (1989). Direct evidence that oxygen-derived free radicals contribute to post ischemic myocardial dysfunction in the intact dog. *Proc Natl Acad Sci USA* 86, 4695–4699.
63. Bolli R., Patel B., Jeroudi M., Lai E., & McKay P. (1988). Demonstration of free radical generation in stunned myocardium of intact dogs with the use of the spin trap a-phenyl-N-tert-butyl nitrone. *J Clin Invest* 82, 476–485.
64. Burton K. (1988). Evidence of direct toxic effects of free radicals on the myocardium. *Free Rad Bio Med* 4, 15–24.
65. Gupta M. & Singhal P. (1989). Time course of structure, function, and metabolic changes due to an exogenous source of oxygen metabolites in the rat heart. *Can J Physiol Pharmcol* 67, 1549–1559.
66. Parks D., Shah A. & Granger D. (1984). Oxygen radicals: effects on intestinal vascular permeability. *Am J Physiol* 247, G167–G170.
67. Przyklenk K., Whittaker P. & Kloner R. (1990). In vivo infusion of oxygen free radical substrates causes myocardial systolic, but not diastolic, dysfunction. *Am Heart J* 119, 807–815.
68. Downey J. (1990). Free radicals and their involvement during long term myocardial ischemia and reperfusion. *Annu Rev Physiol* 52, 487–504.
69. Granger D. (1988). Role of xanthine oxidase and granulocytes in ischemia-reperfusion injury. *Am J Physiol* 255, H1269–H1275.
70. Chien K & Han A. (1984). Accumulation of unesterified arachidonic acid in ischemic canine myocardium: relationship to a phophatidylcholine deacylation reacylation cycle and the depletion of membrane phospholipids. *Circ Res* 54, 312–322.
71. Moncada S. & Higgs A. (1993). The L-argine-nitric oxide pathway. *N Engl J Med* 329, 2002–2012.
72. Patel V., Yellow D., Singh K., Neild G. & Woolfson R. (1993). Inhibition of nitric oxide limits infarct size in the in situ rabbit heart. *Biochem Biophys Res Commun* 194, 234–238.
73. Depre C., Vanoverschelde J., Goudemant J., Mottet I. & Hue L. (1995). Protection against ischemic injury by nonvasoactive concentrations of nitric oxide synthase inhibitors in the perfused rabbit heart. *Circulation* 92:7, 1911–1918.
74. Naseem S., Kontos M., Rao P., Jesse R., Hess M. & Kukreja R. (1995). Sustained inhibition of nitric oxide by NG-nitro-L-arginine improves myocardial function following ischemia/reperfusion in isolated perfused rat heart. *J Moll Cell Cardio* 27, 419–426.
75. Noiri E., Peresleni T., Miller F. & Goligorsky M. (1996). In vivo targeting of inducible NO synthase with oligodeoxynucleotides protects rat kidney against ischemia. *J Clin Invest* 97:10, 2377–2383.
76. Hara H., Friedlander R., Gagliardini V., Ayata C., Fink K., Huang Z., Shimizu-Sasmata M., Yuan J. & Moskowitz. (1997). Inhibition of interleukin 1B converting enzyme family proteases reduces ischemic and excitotoxic neuronal damage. *Proc Natl Acad Sci USA* 94, 2007–2012.
77. Szabolcs M., Michler R., Yang X., Aji W., Roy D., Athan E., Sciacca R., Minanov O. & Cannon P. (1996). Apoptosis of cardiac myocytes during cardiac allograft ejection: relation to induction of nitric oxide synthase. *Circulation* 94:7, 1665–1673.
78. Shito M., Wakabayashi G., Ueda M., Shimazu M., Shirasugi N., Endo M., Mukai M. & Kitajima M. (1997). Interleukin 1 receptor blockade reduces tumor necrosis factor production, tissue injury, and mortality after hepatic ischemia-reperfusion in the rat. *Transplant* 63:1, 143–148.
79. Casey L, Balk R., & Bone R. (1993). Plasma cytokine and endotoxin levels correlate with survival in patients with the sepsis syndrome. *Ann Intern Med* 119, 771–778.
80. Pruitt J., Copeland E. & Moldawer L. (1995). Interleukin-1 and interleukin-1 antagonism in sepsis, systemic inflammatory response syndrone, and septic shock. *Shock* 3:4, 235–251.
81. Fisher C., Slotman G., Opal S., Pribble J., Bone R., Emmanuel G., Ng D., Bloedow D. & Catalano M. (1994b). Initial evaluation of human recombinant interleukin-l receptor antagonist in the treatment of sepsis syndrome: a randomized, open-label, placebocontrolled multicenter trial. The IL-1RA sepsis syndrome study group. *Crit Care Med* 22, 12–21.
82. Robinson, A., Farrar, G. H, Wiblin, C. N., *Methods in Molecular Medicine Humana Press*, Totowa, N.J., 1996.
83. Dudgeon, J. A, Cutting, W. A. M., Chapman, Hall, Immunization: Principles and Practice, London 1991.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for stimulating production of antibodies with catalytic activity comprising:
   a) administering to a test subject, an immunogenic amount of a covalently reactive antigen analog (CRAA);
   b) repeating step a) as necessary to ensure effective antibody production; and
   c) isolating and purifying said antibodies;
wherein said covalently reactive antigen analog contains an electrophilic center flanked by peptide residues derived from proteins associated with a peptide antigen to be targeted for cleavage.

2. A method of stimulating production of catalytic antibodies as claimed in claim 1, wherein an immunogenic amount of a transition state analog (TSA) is co-administered with said CRAA.

3. A method for passively immunizing a patient, comprising:
   a) administering to said patient a catalytic antibody specific for an antigen associated with a medical disorder diagnosed in said patient, said catalytic antibody being produced by the method of claim 1;
   b) repeating step a) as necessary to maintain immunity; and
   c) assessing said patient's sera for the presence of catalytic antibodies.

4. A method for actively immunizing a patient, against a microbial infection, comprising:
   a) complexing a covalently reactive antigen analog (CRAA) comprising an immunogenic microbial epitope from an infectious organism with an adjuvant, said CRAA-epitope-adjuvant complex comprising a vaccine;
   b) administering said vaccine to said patient in a dose in the range of 100–1000 micrograms/kg body weight;
   c) administering at least one booster injection, said at least one booster injections being administered at four week intervals; and
   d) assessing said patient's sera for the presence of catalytic antibodies against said microbial epitope.

* * * * *

UNITED STATES PATENT AND TRADEMARK OFFICE
CERTIFICATE OF CORRECTION

PATENT NO. : 6,855,528 B2
DATED : February 15, 2005
INVENTOR(S) : Sudhir Paul et al.

It is certified that error appears in the above-identified patent and that said Letters Patent is hereby corrected as shown below:

Column 1,
Line 9, please insert the following paragraph:
-- Pursuant to 35 U.S.C. §202(c) it is acknowledged that the U.S. Government has certain rights in the invention described herein, which was made in part with funds from the National Institute of Health, Grant Numbers HL 44126 and AI 31268. --

Signed and Sealed this

Seventeenth Day of May, 2005

JON W. DUDAS
*Director of the United States Patent and Trademark Office*

SEQUENCE LISTING

<160> NUMBER OF SEQ ID NOS: 10

<210> SEQ ID NO 1
<211> LENGTH: 16
<212> TYPE: PRT
<213> ORGANISM: Human Immunodeficiency Virus-1

<400> SEQUENCE: 1

Lys Gln Ile Ile Asn Met Trp Gln Glu Val Gly Lys Ala Met Tyr Ala
 1               5                   10                  15

<210> SEQ ID NO 2
<211> LENGTH: 15
<212> TYPE: PRT

-continued

<213> ORGANISM: Clostridium tetani

<400> SEQUENCE: 2

Gln Tyr Ile Lys Ala Asn Ser Lys Phe Ile Gly Ile Thr Glu Leu
1 5 10 15

<210> SEQ ID NO 3
<211> LENGTH: 9
<212> TYPE: PRT
<213> ORGANISM: Homo sapiens

<400> SEQUENCE: 3

Met Glu Glu Asp Gly Val Arg Lys Cys
1 5

<210> SEQ ID NO 4
<211> LENGTH: 6
<212> TYPE: PRT
<213> ORGANISM: Homo sapiens

<400> SEQUENCE: 4

Cys Glu Gly Pro Cys Arg
1 5

<210> SEQ ID NO 5
<211> LENGTH: 11
<212> TYPE: PRT
<213> ORGANISM: Homo sapiens

<400> SEQUENCE: 5

Lys Gln Ile Ile Asn Met Trp Gln Glu Val Gly
1 5 10

<210> SEQ ID NO 6
<211> LENGTH: 4
<212> TYPE: PRT
<213> ORGANISM: Homo sapiens

<400> SEQUENCE: 6

Ala Met Tyr Ala
1

<210> SEQ ID NO 7
<211> LENGTH: 7
<212> TYPE: PRT
<213> ORGANISM: Homo sapiens

<400> SEQUENCE: 7

Leu Ala Asn Gly Val Glu Leu
1 5

<210> SEQ ID NO 8
<211> LENGTH: 7
<212> TYPE: PRT
<213> ORGANISM: Homo sapiens

<400> SEQUENCE: 8

Asp Asn Gln Leu Val Val Pro
1 5

<210> SEQ ID NO 9
<211> LENGTH: 7
<212> TYPE: PRT
<213> ORGANISM: Homo sapiens

```
<400> SEQUENCE: 9

Pro Lys Lys Lys Met Glu Lys
1               5

<210> SEQ ID NO 10
<211> LENGTH: 7
<212> TYPE: PRT
<213> ORGANISM: Homo sapiens

<400> SEQUENCE: 10

Phe Val Phe Asn Lys Ile Glu
1               5
```